United States Patent

Aloup et al.

[11] Patent Number: 5,807,859
[45] Date of Patent: Sep. 15, 1998

[54] IMIDAZO (1,2-A)-INDENO (1,2-E) PYRAZIN-4-ONE DERIVATIVES AND PHARMACEUTICAL COMPOSITIONS CONTAINING SAME

[75] Inventors: Jean-Claude Aloup, Villeneuve Le Roi; Francois Audiau, Charenton Le Pont; Michel Barreau, Montgeron; Dominique Damour, Orly; Arielle Genevois-Borella, Thiais; Patrick Jimonet, Villepreux; Serge Mignani, Chatenay-Malabry; Yves Ribeill, Villemoisson Sur Orge, all of France

[73] Assignee: Rhone-Poulenc Rorer S.A., Antony Cedex, France

[21] Appl. No.: 716,311

[22] PCT Filed: Mar. 23, 1995

[86] PCT No.: PCT/FR95/00358

§ 371 Date: Sep. 27, 1996

§ 102(e) Date: Sep. 27, 1996

[87] PCT Pub. No.: WO95/26350

PCT Pub. Date: Oct. 5, 1995

[30] Foreign Application Priority Data

Mar. 28, 1994 [FR] France .................. 94 03582

[51] Int. Cl.[6] ............. A61K 31/495; A61K 31/535; C07D 241/36; C07D 403/00
[52] U.S. Cl. .............. 514/255; 514/233.2; 544/115; 544/295; 544/343
[58] Field of Search ............... 544/343, 295, 544/115; 514/255, 233.2

[56] References Cited

U.S. PATENT DOCUMENTS

| | | | |
|---|---|---|---|
| 4,354,027 | 10/1982 | Loev et al. | 544/346 |
| 4,400,382 | 8/1983 | Brown et al. | 424/250 |
| 4,507,300 | 3/1985 | Brown et al. | 514/280 |
| 4,668,678 | 5/1987 | Brown et al. | 514/250 |
| 5,153,196 | 10/1992 | McQuaid et al. | 514/250 |
| 5,196,421 | 3/1993 | McQuaid et al. | 514/250 |

FOREIGN PATENT DOCUMENTS

| | | |
|---|---|---|
| 2696466 | 4/1994 | France . |
| 2707645 | 1/1995 | France . |
| WO9306103 | 4/1993 | WIPO . |
| WO9400124 | 1/1994 | WIPO . |
| WO9418175 | 8/1994 | WIPO . |
| WO9502601 | 1/1995 | WIPO . |

OTHER PUBLICATIONS

Derwent Abstract of FR–A–2 696 466.
Derwent Abstract of FR–A–2 707 645.
McQuaid et al., "Synthesis and Excitatory Amino Acid Pharmacology of a Series of Heterocyclic–Fused Quinoxalinones and Quinazolinones", J. Med. Chem. 35(18):3319–3324 (1992).
Rashet et al., "A Facile Synthesis of Novel Triazoloquinoxalines and Triazinoquinozalinones [1]", J. Of Heterocyclic Chemistry, 27(3):691–694 (1990).

*Primary Examiner*—Mukund J. Shah
*Assistant Examiner*—Brenda Coleman
*Attorney, Agent, or Firm*—Finnegan, Henderson, Farabow, Garrett & Dunner, L.L.P.

[57] ABSTRACT

Pharmaceutical compositions containing, as the active principle, compounds of formula (I):

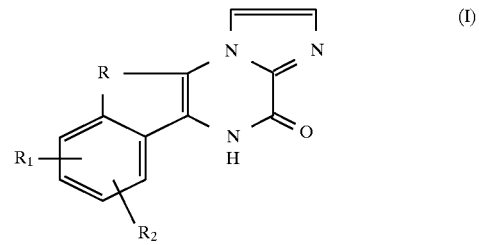

wherein R, $R_1$ and $R_2$ are as defined in the description, or salts thereof, the novel compounds of formula (I), and the preparation thereof. The compounds of formula (I) have valuable pharmacological properties and are alpha-amino-3-hydroxy-5-methyl-4-isoxazolepropionic acid (AMPA) receptor antagonists, this receptor also being known as the quisqualate receptor. Furthermore, the compounds of formula (I) are non-competitive N-methyl-D-aspartate (NDMA) receptor antagonists, and particularly NMDA receptor glycine modulation site ligands.

16 Claims, No Drawings

IMIDAZO (1,2-A)-INDENO (1,2-E) PYRAZIN-4-ONE DERIVATIVES AND PHARMACEUTICAL COMPOSITIONS CONTAINING SAME

This application is a 371 of PCT/FR95/00358 filed Mar. 23, 1995.

The present invention relates to pharmaceutical compositions containing, as active principle, at least one compound of formula:

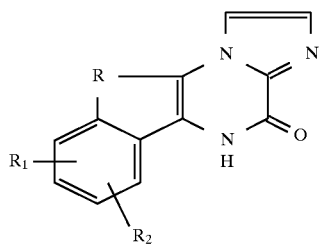

or the pharmaceutically acceptable salts thereof, the novel compounds of formula (I), the salts and the preparation thereof.

According to the invention, the pharmaceutical compositions contain at least one compound of formula (I) in which R represents a radical $C=R_3$, $C(R_4)R_5$ or $CH-R_6$, $R_1$ and $R_2$, which may be identical or different, represent hydrogen or halogen atoms or alkyl, alkoxy, amino, —N=CH—N(alk)alk', nitro, cyano, phenyl, imidazolyl, $SO_3H$, hydroxyl, polyfluoroalkoxy, —$COOR_7$, —NH—CO—$NR_8R_9$, —N(alk)—CO—$NR_8R_9$, —N(alk-Ar)—CO—$NR_8R_9$, —NH—CS—$NR_8R_9$, —N(alk)—CS—$NR_8R_9$, —NH—CO—$R_{18}$, —NH—CS—$R_{19}$, —NH—C(=$NR_{20}$)—$NR_7R_9$, —N(alk)—C(=$NR_{20}$)—$NR_7R_9$, —NH—$SO_2$—$NR_7R_9$, —N(alk)—$SO_2$—$NR_7R_9$, —CO—$NR_7R_9$, —NH—$SO_2$—$CF_3$, —NH—$SO_2$-alk, —$NR_9R_{11}$, —$S(O)_m$-alk-Ar or —$SO_2$—$NR_7R_9$ radicals, 2-oxo-1-imidazolidinyl radicals in which position -3 is optionally substituted with an alkyl radical, or 2-oxoperhydro-1-pyrimidinyl radicals in which position -3 is optionally substituted with an alkyl radical, $R_3$ represents a radical NO-alk, $CHR_{10}$, $NR_7$, $C(COOR_7)R_{16}$ or $C(CONR_7R_{15})R_{16}$, $R_4$ represents an alkyl, -alk-Het or -alk-Het" radical or a phenylalkyl radical in which the phenyl ring is optionally substituted with one or more substituents chosen from halogen atoms and alkyl, alkoxy, nitro, amino, hydroxyl, cyano, -alk-$NH_2$, —$COOR_7$ and -alk-$COOR_7$ radicals, $R_5$ represents a radical —$NR_{12}R_{13}$, —NH—CHO, —NH—$COOR_{17}$, —NH—$SO_2R_{19}$, —$COOR_7$, -alk-$COOR_7$, -alk-$CONR_7R_{15}$, -alk-$NR_7R_{15}$, -alk-OH, -alk-CN or -alk-Het", a phenylalkyl radical in which the phenyl ring is substituted with one or more substituents chosen from halogen atoms and alkyl, alkoxy, nitro, amino, hydroxyl, cyano, -alk-$NH_2$, —$COOR_7$ and -alk-$COOR_7$ radicals, a radical —NH—CO—Ar in which Ar is optionally substituted with one or more substituents chosen from halogen atoms and alkyl, alkoxy, nitro, amino, hydroxyl, cyano, -alk-$NH_2$, —$COOR_7$ and -alk-$COOR_7$ radicals, a radical —NH—CO-Het, —NH—CO-Het", —NH—CO-alk-Het, —NH—CO-alk-Het", —NH—CO-alk-$COOR_7$ or —NH—CO-alk-$NR_7R_{15}$, a radical —NH—CO-alk-Ar in which Ar is optionally substituted with one or more substituents chosen from halogen atoms and alkyl, alkoxy, nitro, amino, hydroxyl, cyano, -alk-$NH_2$, —$COOR_7$ and -alk-$COOR_7$ radicals, a radical —NH—CO—C(Ar)($CF_3$) $OCH_3$, a 1-pyrrolyl radical which is optionally substituted with a radical —$COOR_7$, a radical —NH—CO—NH-alk-Ar in which Ar is optionally substituted with one or more substituents chosen from halogen atoms and alkyl, alkoxy, nitro, amino, hydroxyl, cyano, -alk-$NH_2$, —$COOR_7$ and -alk-$COOR_7$ radicals, a radical —NH—CO—NH-Het, —NH—CO—NH-Het", —NH—CO—NH-alk-Het or —NH—CO—NH-alk-Het", a radical —NH—CO—NH—Ar in which Ar is optionally substituted with one or more substituents chosen from halogen atoms and alkyl, alkoxy, nitro, amino, hydroxyl, cyano, -alk-$NH_2$, —$COOR_7$ and -alk-$COOR_7$ radicals, or a radical —NH—COalk, —NH—COcycloalkyl, —NH—CO—NH-alk or —NH—CO—$NH_2$, $R_6$ represents a radical —NH—CHO, —COOalk, -alk-$COOR_7$ or -alk-CO—$NR_7R_{15}$, a phenylalkyl radical in which the phenyl ring is substituted with one or more substituents chosen from halogen atoms and alkyl, alkoxy, nitro, amino, acetylamino, hydroxyl, cyano, -alk-$NH_2$, —$COOR_7$ and -alk-$COOR_7$ radicals, a radical —$R_{14}$—$COOR_7$, —CO—$COOR_7$ or —NH—$COOR_{17}$, a radical —NH—CO—Ar in which Ar is substituted with one or more substituents chosen from halogen atoms and alkyl, alkoxy, nitro, amino, hydroxyl, cyano, -alk-$NH_2$, —$COOR_7$ and -alk-$COOR_7$ radicals, a radical —NH—CO-Het, —NH—CO-alk-Het, —NH—CO-Het", —NH—CO-alk-Het", —NH—CO-alk(2–6C)—$COOR_7$, —NH—CO-alk(2–6C)—$NH_2$, —NH—CO-alk-N(alk)$_2$ or —NH—CO-alk-NHalk, a radical —NH—CO-alk-Ar in which Ar is optionally substituted with one or more substituents chosen from halogen atoms and alkyl, alkoxy, nitro, amino, hydroxyl, cyano, -alk-$NH_2$, —$COOR_7$ and -alk-$COOR_7$ radicals, a radical —NH—CO—C(Ar)($CF_3$) $OCH_3$ or -alk-Het", a 1-pyrrolyl radical which is optionally substituted with a radical —$COOR_7$, a radical —NH—CO—NH-alk-Ar in which Ar is optionally substituted with one or more substituents chosen from halogen atoms and alkyl, alkoxy, nitro, amino, hydroxyl, cyano, -alk-$NH_2$, —$COOR_7$ and -alk-$COOR_7$ radicals, a radical —NH—CO—NH-alk-Het, —NH—CO—NH-alk-Het" or —NH—CO—NH-Het", or a radical —NH—CO—NH—Ar in which Ar is substituted with one or more substituents chosen from halogen atoms and alkyl, alkoxy, nitro, amino, hydroxyl, cyano, -alk-$NH_2$, —$COOR_7$ and -alk-$COOR_7$ radicals, $R_7$ represents a hydrogen atom or an alkyl radical, $R_8$ represents a hydrogen atom or an alkyl, -alk-$COOR_7$, -alk-Het", -alk-Het or -alk-$NR_9R_7$ radical, a phenylalkyl radical in which the phenyl ring is optionally substituted with one or more substituents chosen from halogen atoms and alkyl, alkoxy, nitro, amino, hydroxyl, -alk-$NH_2$, $COOR_7$, cyano and -alk-$COOR_7$ radicals, a phenyl radical which is optionally substituted with one or more substituents chosen from halogen atoms and alkyl, alkoxy, nitro, amino, hydroxyl, -alk-$NH_2$, —$COOR_7$, cyano and -alk-$COOR_7$ radicals, or a radical -Het or -Het", $R_9$ represents a hydrogen atom or an alkyl radical, $R_{10}$ represents a radical -alk-$COOR_7$, -Het" or -alk-Het", a phenyl radical which is substituted with one or more substituents chosen from halogen atoms and alkyl, alkoxy, nitro, amino, hydroxyl, -alk-$NH_2$, —$COOR_7$, cyano and -alk-$COOR_7$ radicals or a phenylalkyl radical in which the phenyl ring is substituted with one or more substituents chosen from halogen atoms and alkyl, alkoxy, nitro, amino, hydroxyl, -alk-$NH_2$, —$COOR_7$, cyano and -alk-$COOR_7$ radicals, $R_{11}$ represents an alkyl, -Het, -Het" or alkoxycarbonyl radical, $R_{12}$ represents a hydrogen atom or an alkyl, -alk-$COOR_7$, -alk-$NR_7R_{15}$, -alk-Het or -alk-Het" radical or a phenylalkyl radical in which the phenyl ring is optionally substituted with one or more substituents chosen from halogen atoms and alkyl, alkoxy, nitro, amino, hydroxyl, -alk-$NH_2$, carboxyl, alkoxycarbonyl, cyano and -alk-$COOR_7$ radicals, $R_{13}$ represents a hydrogen atom or an alkyl radical, $R_{14}$ represents a —CHOH— or —CHOH-alk(1–5C)— chain, $R_{15}$ represents a hydrogen atom or an alkyl radical, $R_{16}$ represents a hydrogen atom or an alkyl radical, $R_{17}$ represents an alkyl or phenylalkyl radical, $R_{18}$ represents a hydrogen atom or an alkyl (1–9C in a straight or branched chain) radical, an alkoxy, -alk-$COOR_7$, -alk-Het", -alk-Het or -alk-$NR_9R_7$ radical, a phenylalkyl radical in which the phenyl ring is optionally substituted with one or more substituents chosen from halogen atoms and alkyl, alkoxy, nitro, amino, hydroxyl, -alk-$NH_2$, —$COOR_7$, cyano and -alk-$COOR_7$ radicals, a phenyl radical which is optionally substituted with one or more substituents chosen from halogen atoms and alkyl, alkoxy, nitro, amino, hydroxyl, -alk-$NH_2$, $COOR_7$, cyano and -alk-$COOR_7$ radicals, or a radical Het or -Het", $R_{19}$ represents an alkyl or phenyl radical, $R_{20}$ represents a hydrogen atom or an alkyl radical, alk represents an alkyl or alkylene radical, alk' represents an alkyl radical, Ar represents a phenyl radical, m is equal to 0, 1 or 2, Het represents a saturated or unsaturated mono- or polycyclic heterocycle containing 4 to 9 carbon atoms and one or more hetero atoms (O, S, N), Het" represents a saturated or unsaturated mono- or polycyclic heterocycle containing 1 to 3 carbon atoms and one or more hetero atoms (O, S, N) which is optionally substituted with one or more alkyl, phenyl or phenylalkyl radicals or a saturated or unsaturated mono- or polycyclic heterocycle containing 4 to 9 carbon atoms and one or more hetero atoms (O, S, N) which is substituted with one or more alkyl, phenyl or phenylalkyl radicals, it being understood that when R, and $R_2$ represent hydrogen atoms and R represents a radical $CHR_6$, $R_6$ represents a radical -alk-Het" in which alk represents an alkyl (1C) radical, Het" cannot be a 2-imidazolyl radical.

Except where otherwise mentioned, in the preceding definitions and in those which follow, the alkyl, alkoxy and alkylene radicals and portions contain 1 to 6 carbon atoms in a straight or branched chain, the cycloalkyl radicals contain 3 to 6 carbon atoms and the halogen atoms are chosen from fluorine, chlorine, bromine and iodine.

Preferably, Het is chosen from pyrrolyl, pyridyl, pyrimidinyl, morpholinyl, pyrazinyl, pyrrolidinyl, piperazinyl, piperidyl, thienyl and furyl rings and Het" is chosen from pyrrolyl rings substituted with one or more alkyl, phenyl or phenylalkyl radicals, pyridyl rings substituted with one or more alkyl, phenyl or phenylalkyl radicals, pyrimidinyl rings substituted with one or more alkyl, phenyl or phenylalkyl radicals, imidazolyl rings optionally substituted with one or more alkyl, phenyl or phenylalkyl radicals, thiazolyl rings optionally substituted with one or more alkyl, phenyl or phenylalkyl radicals, thiazolinyl rings optionally substituted with one or more alkyl, phenyl or phenylalkyl radicals, pyrazinyl rings optionally substituted with one or more alkyl, phenyl or phenylalkyl radicals, tetrazolyl rings optionally substituted with one or more alkyl, phenyl or phenylalkyl radicals, triazolyl rings optionally substituted with one or more alkyl, phenyl or phenylalkyl radicals, oxazolyl rings optionally substituted with one or more alkyl, phenyl or phenylalkyl radicals, pyrrolidinyl rings substituted with one or more alkyl, phenyl or phenylalkyl radicals, azetidinyl rings optionally substituted with one or more alkyl, phenyl or phenylalkyl radicals, piperazinyl rings substituted with one or more alkyl, phenyl or phenylalkyl radicals, piperidyl rings substituted with one or more alkyl, phenyl or phenylalkyl radicals, thienyl rings substituted with one or more alkyl, phenyl or phenylalkyl radicals, oxazolinyl rings optionally substituted with one or more alkyl, phenyl or phenylalkyl radicals, furyl rings optionally substituted with one or more alkyl, phenyl or phenylalkyl radicals, or imidazolinyl rings optionally substituted with one or more alkyl, phenyl or phenylalkyl radicals. The substituents of these rings are preferably methyl, phenyl or benzyl radicals.

The polyfluoroalkoxy radicals are preferably trifluoromethoxy radicals.

The radicals $R_1$ are preferably in position -7 or -8.

The compounds of formula (I) for which $R_3$ represents a radical NO-alk, $C(COOR_7)R_{16}$, $C(CONR_7R_{15})R_{16}$ or $CHR_{10}$ have isomeric forms (E and Z). These isomers and the mixtures thereof form part of the invention.

The compounds of formula (I) for which R represents a radical CH—$R_6$, $R_6$ represents a radical —CO—$COOR_7$, have tautomeric forms (E and Z). These tautomeric forms also form part of the invention.

The enantiomers and diastereoisomers of the compounds of formula (I) for which R represents a radical $C(R_4)R_5$ or CH—$R_6$ also form part of the invention.

The present invention also relates to the compounds of formula (I) for which R, $R_1$ and $R_2$ are defined as above with the exception of those for which (a) $R_1$ and $R_2$ represent hydrogen atoms and R represents a radical $CHR_6$, $R_6$ represents a radical -alk-Het" in which alk represents an alkyl (1C) radical and Het" represents a 2-imidazolyl radical, (b) $R_1$ and $R_2$ represent hydrogen atoms and R represents a radical $CHR_6$ in which $R_6$ represents a radical —NHCHO or -alk-$COOR_7$ in which $R_7$ represents a hydrogen atom or a tert-butyl radical, (c) $R_1$ and $R_2$ represent hydrogen atoms and R represents a radical C=$R_3$ in which $R_3$ represents a radical $CHR_{10}$ and $R_{10}$ represents a 2-imidazolyl radical, and (d) $R_1$ represents a hydrogen atom, $R_2$ represents a chlorine atom in position -7, R represents a radical $CHR_6$ and $R_6$ represents a radical —NHCHO.

Among these compounds, those are preferred for which $R_1$ is in position -7 or -8.

The present invention also relates to the salts of these novel compounds, their isomers, their enantiomers and diastereoisomers and their tautomeric forms mentioned above.

The compounds of formula (I) for which R represents a radical C=$R_3$ and $R_3$ represents a radical NO-alk may be prepared by alkylation of a derivative of formula:

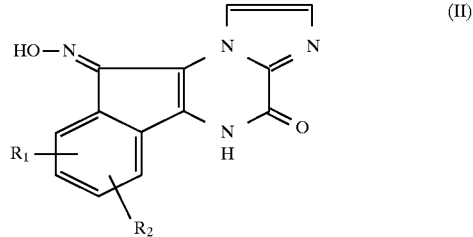

in which $R_1$ and $R_2$ have the same meanings as in formula (I).

This alkylation is preferably carried out using an alkyl halide, in the presence of a base such as an alkali metal amide (sodium amide), in ammonia, at a temperature in the region of −33° C.

The derivatives of formula (II) may be obtained by the action of an alkyl nitrite on a derivative of formula:

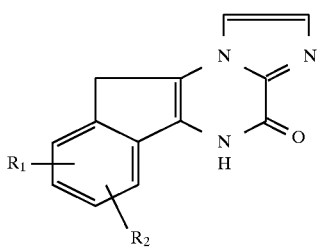

in which $R_1$ and $R_2$ have the same meanings as in formula (I).

This reaction is generally carried out in an inert solvent such as dimethyl sulphoxide, in the presence of an alkali metal hydride such as sodium hydride, at a temperature in the region of 20° C. Isoamyl nitrite is preferably used.

The derivatives of formula (III) may be obtained by dealkylation and desalification of a derivative of formula:

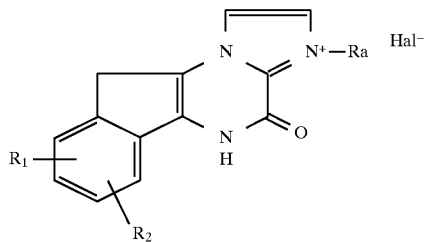

in which $R_1$ and $R_2$ have the same meanings as in formula (I), Ra represents an alkyl radical and Hal represents a halogen atom.

This reaction is preferably carried out, in the presence of imidazole, at a temperature between 100° and 200° C.

The derivatives of formula (IV) may be obtained by the action of a derivative of formula:

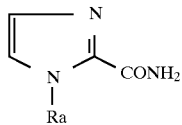

in which Ra has the same meanings as in formula (IV), on a haloindanone of formula:

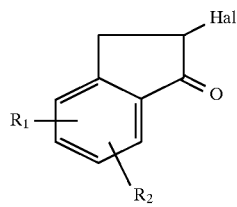

in which $R_1$ and $R_2$ have the same meanings as in formula (I) and Hal represents a halogen atom.

This reaction is generally carried out in an inert solvent such as dimethylformamide, at a temperature between 50° and 150° C. (preferably at 115° C.).

The derivatives of formula (V) may be obtained by application or adaptation of the method described by D. D. Davey, J. Org. Chem., 52, 4379 (1987).

The 2-haloindanones of formula (VI) may be obtained by application or adaptation of the method described by M. Olivier et al., Bull. Soc. Chim. France, 3092 (1973).

The derivatives of formula (III) may also be prepared by cyclization of a derivative of formula:

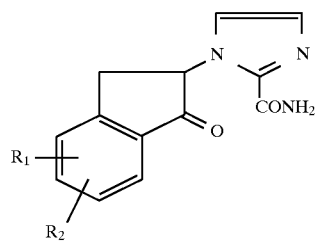

in which $R_1$ and $R_2$ have the same meanings as in formula (I).

This cyclization is generally carried out using an acid such as hydrochloric acid or acetic acid, in aqueous solution, at a temperature between 20° C. and the boiling point of the reaction medium.

The derivatives of formula (VII) may be obtained by the action of ammonia on a derivative of formula:

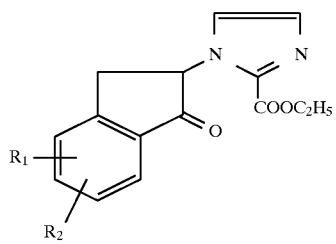

in which $R_1$ and $R_2$ have the same meanings as in formula (I).

This reaction is generally carried out in an inert solvent such as an alcohol, at a temperature between 20° C. and the boiling point of the reaction medium.

The derivatives of formula (VIII) may be obtained by condensation of ethyl imidazole-2-carboxylate on a derivative of formula (VI) in which $R_1$ and $R_2$ have the same meanings as in formula (I) and Hal represents a halogen atom and, preferably, a bromine atom.

This reaction is carried out in an inert solvent such as a lower aliphatic alcohol (methanol or ethanol for example), an aromatic hydrocarbon such as toluene, or dimethylformamide, or is carried out in the absence of solvent and optionally in the presence of sodium hydride, at a temperature between 20° C. and the boiling point of the reaction medium or the fusion of the reaction medium, or is carried out in acetone, in the presence of an alkali metal carbonate, at a temperature between 20° C. and the boiling point of the reaction medium.

Ethyl imidazole-2-carboxylate may be obtained according to the method described in U.S. Pat. No. 3,600,399.

The compounds of formula (I) for which R represents a radical C=$R_3$ and $R_3$ represents a radical $CHR_{10}$ may be prepared by the action of a derivative of formula (III), in which $R_1$ and $R_2$ have the same meanings as in formula (I), on a derivative of formula OHC—$R_{10}$ in which $R_{10}$ has the same meanings as in formula (I).

This reaction is generally carried out in an inert solvent such as dimethylformamide, 1,2-dimethoxyethane, an alcohol (methanol or ethanol for example) or a mixture of these solvents, in the presence of a base such as sodium hydroxide, potassium hydroxide or a strong organic base such as 1,8-diazabicyclo[5,4,0]undec-7-ene, at a temperature between 20° and 100° C., or is carried out in dimethyl sulphoxide, in the presence of an alkali metal hydride such as sodium hydride, at a temperature in the region of 20° C., or is carried out in the presence of tetrabutylammonium bromide and a base such as an alkali metal hydroxide (sodium hydroxide or potassium hydroxide for example), in dimethyl sulphoxide, at a temperature between 20° and 100° C., or is carried out in acetic acid or acetic anhydride, in the presence of ammonium acetate, at a temperature between 20° C. and the boiling point of the reaction medium.

The derivatives of formula OHC—$R_{10}$ are commercially available or may be obtained by application or adaptation of the methods described in the examples. They may also be obtained (a) by oxidation of the corresponding alcohols $HOH_2C$—$R_{10}$ (using $K_2Cr_2O_7$ in a sulphuric medium; $CrO_3$ in pyridine or $MnO_2$ in a chlorinated solvent (dichloromethane for example), at a temperature in the region of 20° C. or using dimethyl sulphoxide and ClCO—COCl by adaptation or application of the method described by D. Swern et al., J. Org. Chem., 44, 4148 (1979)); (b) by reduction of the corresponding carboxylic acids HOOC—$R_{10}$ (using lithium aluminium hydride or $AlH_3$, in an inert solvent such as tetrahydrofuran, at a temperature between 0° and 25° C.); (c) by reduction of the corresponding esters alkOOC-$R_{10}$ (using diisobutylaluminium hydride, in an inert solvent such as toluene, at a temperature between −70° C. and 25° C. or lithium aluminium hydride, in an inert solvent such as tetrahydrofuran, at a temperature between 0° and 25° C.). The derivatives OHC—$R_{10}$ for which $R_{10}$ represents a radical -alk-Het" may also be obtained by application or adaptation of the method described by G. T. Yound et al., J. Chem. Soc. Perkin Trans I, 1767 (1985).

The corresponding alcohols $HOH_2C$—$R_{10}$ for which $R_{10}$ represents a radical -alk-Het" or -alk-Ar in which Ar is substituted are commercially available or may be obtained from the corresponding organometallic compounds by application or adaptation of the methods described by N. S. Narasimhan et al., Tetrahedron Lett., 22 (29), 2797 (1981); L. Estel et al., J. Het. Chem., 26, 105 (1989); N. S. Narasimhan et al., Synthesis, 957 (1983); F. Marsais et al., J. Heterocyclic Chem., 25, 81 (1988); H. W. Gshwend et al., Organic Reactions, 26, I (1979) and V. S. Snieckus, Chem. Rev, 90, 879 (1990). Preferably, the organolithium reagent or the organomagnesium reagent of the corresponding heterocycle or of the corresponding substituted benzene is reacted with formaldehyde, ethylene oxide or a derivative Hal-alk-$CH_2$OP where P is a protecting group (methyl ether, tetrahydropyranyl ether, benzyl ether or triethylsilyl ether for example), Hal is a halogen atom and alk is an alkyl radical, followed by liberation of the alcohol function by application or adaptation of the methods described by W. Greene et al., Protecting Groups in Organic Synthesis, second edition, 1991, John Wiley and sons.

The corresponding alcohols $HOH_2C$—$R_{10}$ for which $R_{10}$ represents a radical -alk-Het" or -alk-Ar in which Ar is substituted may also be obtained by reduction of the corresponding carboxylic acids or of the corresponding esters, using lithium aluminium hydride, in an inert solvent such as tetrahydrofuran or diethyl ether, at the boiling point of the reaction medium.

The corresponding alcohols $HOH_2C$—$R_{10}$ for which $R_{10}$ represents a radical -alk-Het" may also be obtained by application or adaptation of the method described by J. Th. Meyer et al., Helv. Chem. Acta, 65, 1868 (1982) starting with derivatives Hal-alk(0–5C)-Het" which are themselves obtained by the action of a halogenating agent (halogenated phosphorus derivative or thionyl chloride) on a corresponding derivative $HOH_2C$-alk(0–5C)-Het", optionally in an inert solvent such as dichloromethane, at a temperature between 20° and 40° C.

The corresponding carboxylic acids HOOC—$R_{10}$ for which $R_{10}$ represents a radical -Het", -alk-Het" or -alk-Ar in which Ar is substituted are commercially available or may be obtained from the corresponding heterocycles or from the corresponding substituted benzene by application or adaptation of the methods described by L. Estel et al., J. Heterocyclic Chem., 26, 105 (1989); N. S. Narasimhan et al., Synthesis, 957 (1983); A. Turck et al., Synthesis, 881 (1988); A. J. Clarke et al., Tetrahedron Lett, 27, 2373 (1974); A. R. Katritzky et al., Org. Perp. Procedure Int., 20 (6), 585 (1988); N. Furukawa et al., Tetrahedron Lett., 28 (47), 5845 (1987); H. W. Gschwend et al., Organic Reactions, 26, 1 (1979) et V. Snieckus, Chem. Rev., 90, 879 (1990). Preferably, the organometallic derivative of the corresponding heterocycle or of the corresponding substituted benzene (organolithium reagent or organomagnesium reagent for example) is prepared and is reacted either with $CO_2$ or with a derivative Hal-alk-COOalk in which Hal represents a halogen atom and alk represents an alkyl radical, followed by hydrolysis of the ester.

The derivatives Hal-alk-CCOalk are commercially available or are prepared by the action of Hal-alk-Hal, in which Hal represents a halogen atom and alk represents an alkyl radical, on an alkali metal cyanide such as sodium cyanide or potassium cyanide in a water-lower aliphatic alcohol mixture, at a temperature between 0° C. and the boiling point of the reaction medium, followed by the action of an acid such as hydrochloric acid, in the presence of a straight- or branched-chain C1–C6 aliphatic alcohol, at a temperature between 0° C. and the boiling point of the reaction medium.

The derivatives Hal-alk-Hal are commercially available or may be obtained from the corresponding diols by application or adaptation of the methods described by C. Larock, "Comprehensive Organic Transformations", Ed. VHC, page 353 (1989).

The corresponding esters alkOOC-$R_{10}$ are commercially available or may be obtained from the acids by the action of an organic acid such as hydrochloric acid or sulphuric acid, in the alcohol which also serves as the esterifying agent, at the boiling point of the reaction medium.

The derivatives OHC—$R_{10}$ for which $R_{10}$ represents a radical -alkCOO$R_7$ are commercially available or may be obtained by reduction of the corresponding carboxylic acids by application or adaptation of the methods described by H. C. Brown et al., J. Am. Chem. Soc., 106, 8001 (1984) et J. Org. Chem., 52, 5400 (1987). The corresponding acids are commercially available or may be obtained by application or adaptation of the methods described by H. Hunsdiecker et al., Chem. Ber., 75, 256 (1942) and R. F. Naylor, J. Chem. Soc., 1108 (1947).

The compounds of formula (I) for which R represents a radical C=$R_3$ and $R_3$ represents a radical $NR_7$ may be prepared by the action of a derivative of formula:

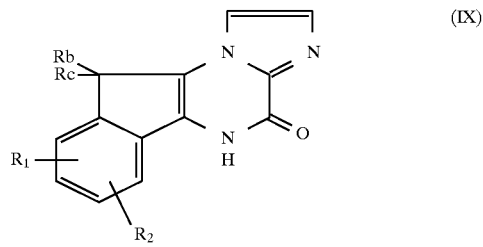

in which $R_1$ and $R_2$ have the same meanings as in formula (I), Rb represents a hydrogen atom, Rc represents a radical —$NHR_7$ and $R_7$ has the same meanings as in formula (I), on ethyl trifluoroacetate.

This reaction is generally carried out in an inert solvent such as dimethylformamide, at a temperature in the region of 60° C.

The derivatives of formula (IX) for which $R_1$ and $R_2$ have the same meanings as in formula (I), Rb represents a hydrogen atom and Rc represents a radical —$NHR_7$ and $R_7$ represents a hydrogen atom, may be obtained by hydrolysis of a derivative of formula (IX) for which $R_1$ and $R_2$ have the same meanings as in formula (I), Rb represents a hydrogen atom and Rc represents a radical —NH—COalk in which alk represents an alkyl radical.

This hydrolysis is generally carried out using an inorganic acid such as hydrochloric acid, in an aqueous medium, at the boiling point of the reaction medium.

The derivatives of formula (IX) for which $R_1$ and $R_2$ have the same meanings as in formula (I), Rb represents a hydrogen atom and Rc represents a radical —NH—COalk in which alk represents an alkyl radical, may be obtained by the action of a reducing agent on a derivative of formula (II) for which $R_1$ and $R_2$ have the same meanings as in formula (I), followed by a treatment with an anhydride (alk(1–5C)CO)$_2$O.

This reaction is generally carried out at a temperature between 50° and 100° C. Zinc is preferably used as reducing agent.

The derivatives of formula (IX), for which $R_1$ and $R_2$ have the same meanings as in formula (I), Rb represents a hydrogen atom, Rc represents a radical —$NHR_7$ and $R_7$ represents an alkyl radical, may be obtained by the action of a corresponding derivative of formula (IX), for which $R_1$ and $R_2$ have the same meanings as in formula (I), Rb represents a hydrogen atom, Rc represents a radical —$NHR_7$ and $R_7$ represents a hydrogen atom, on a derivative Hal-Rd in which Rd represents an alkyl radical and Hal represents a halogen atom.

This reaction is preferably carried out in an inert solvent such as dimethylformamide, tetrahydrofuran or dimethyl sulphoxide, in the presence of a base such as a tertiary amine (triethylamine for example) or an aromatic amine (pyridine for example) or an inorganic base such as an alkali metal hydroxide (sodium hydroxide or potassium hydroxide for example), at a temperature between 20° C. and the boiling point of the reaction medium.

The compounds of formula (I), for which R represents a radical C=$R_3$ and $R_3$ represents a radical C(COOR$_7$)R$_{16}$, may be prepared by dehydration of a derivative of formula (IX) in which $R_1$ and $R_2$ have the same meanings as in formula (I), Rb represents a hydrogen atom and Rc represents a radical —C(OH)(R$_{16}$)COOR$_7$ in which $R_7$ and $R_{16}$ have the same meanings as in formula (I).

This reaction is carried out in an inert solvent such as dimethylformamide, at a temperature in the region of 100° C., or in acetic anhydride in the presence of a catalytic amount of zinc chloride, at the boiling point of the reaction medium.

The derivatives of formula (IX), for which Rb represents a hydrogen atom and Rc represents a radical —C(OH)(R$_{16}$)COOR$_7$ in which $R_7$ and $R_{16}$ have the same meanings as in formula (I), may be obtained by condensation of a derivative of formula (III), for which $R_1$ and $R_2$ have the same meanings as in formula (I), on a derivative $R_{16}$—CO—COOR$_7$ for which $R_7$ and $R_{16}$ have the same meanings as in formula (I).

This condensation is generally carried out in an inert solvent such as dimethylformamide, in the presence of an alkali metal hydride such as sodium hydride, at a temperature in the region of 20° C.

The derivatives of formula $R_{16}$—CO—COOR$_7$ in which $R_7$ and $R_{16}$ have the same meanings as in formula (I) are commercially available or may be obtained by application or adaptation of the methods described by N. Rabjohn, Organic Reactions, V, 331 and H. H. Wasserman et al., J. Org. Chem, 50, 3573 (1985).

The compounds of formula (I), for which R represents a radical C=$R_3$ and $R_3$ represents a radical C(CONR$_7$R$_{15}$)R$_{16}$, may be prepared by the action of a corresponding compound of formula (I), for which R represents a radical C=$R_3$ and $R_3$ represents a radical C(COOR$_7$)R$_{16}$, on an amine HNR$_7$R$_{15}$ in which $R_7$ and $R_{15}$ have the same meanings as in formula (I).

When the acid is used, the process is performed in the presence of a coupling agent used in peptide chemistry such as a carbodiimide (for example N,N'-dicyclohexylcarbodiimide) or N,N'-carbonyldiimidazole, in an inert solvent such as an ether (tetrahydrofuran or dioxane for example), an amide (dimethylformamide) or a chlorinated solvent (methylene chloride, 1,2-dichloroethane or chloroform for example) at a temperature between 0° C. and the reflux temperature of the reaction mixture. When an ester is used, the process is then performed either in an organic medium, optionally in the presence of an acid acceptor such as a nitrogen-containing organic base (trialkylamine, pyridine, 1,8-diazabicyclo[5.4.0]undec-7-ene or 1,5-diazabicyclo[4.3.0]non-5-ene for example), in a solvent as mentioned above, or in a mixture of these solvents, at a temperature between 0° C. and the reflux temperature of the reaction mixture, or is performed in a two-phase aqueous-organic medium in the presence of an alkali metal or alkaline-earth metal base (sodium hydroxide or potassium hydroxide) or a carbonate or bicarbonate of an alkali metal or alkaline-earth metal, at a temperature between 0° C. and 40° C.

The compounds of formula (I), for which R represents a radical C=$R_3$ and $R_3$ represents a radical C(CONR$_7$R$_{15}$)R$_{16}$ in which $R_7$ and $R_{15}$ represent hydrogen atoms, may also be prepared by the action of a corresponding compound of formula (I), for which R represents a radical C=$R_3$ and $R_3$ represents a radical C(COOR$_7$)R$_{16}$ in which $R_7$ represents a hydrogen atom, on oxalyl chloride, followed by ammonium hydroxide.

The action of oxalyl chloride generally takes place in a halogenated solvent such as chloroform, at a temperature between 0° and 20° C.; the action of ammonium hydroxide takes place after addition of dimethylformamide to the reaction medium, at a temperature in the region of 20° C.

The compounds of formula (I), for which R represents a radical C(R$_4$)R$_5$ in which $R_5$ represents a radical -alk-COOR$_7$, —NH—COalk or —NR$_{12}$R$_{13}$ in which $R_{12}$ and $R_{13}$ represent hydrogen atoms, may be prepared by the action of a halide Hal-R$_4$, in which Hal represents a halogen atom and R$_4$ has the same meanings as in formula (I), on a derivative of formula (IX) in which $R_1$ and $R_2$ have the same meanings as in formula (I), Rb represents a hydrogen atom and Rc represents a radical -alk-COOR$_7$ or —NH—COalk in which alk represents an alkyl radical and $R_7$ has the same meanings as in formula (I), optionally followed by hydrolysis of the acylamino derivative.

This reaction is generally carried out in an inert solvent such as dimethyl sulphoxide, in the presence of an alkali metal hydride such as sodium hydride, at a temperature in the region of 20° C. The hydrolysis is generally carried out using an inorganic acid such as hydrochloric acid, in an aqueous medium, at the boiling point of the reaction medium.

The halides Hal-$R_4$ are commercially available or may be obtained from the corresponding alcohols by application or adaptation of the methods described by R. C. Larock, "Comprehensive Organic Transformations", Ed. VCH, page 353 (1989).

The compounds of formula (I), for which R represents a radical $C(R_4)R_5$ in which $R_5$ represents a radical —$NR_{12}R_{13}$, $R_{13}$ represents a hydrogen atom or an alkyl radical and $R_{12}$ represents an alkyl radical, a radical -alk-$COOR_7$, -alk-$NR_7R_{15}$, -alk-Het or -alk-Het" or a phenylalkyl radical in which the phenyl ring is optionally substituted, may be prepared by the action of a corresponding compound of formula (I), for which R represents a radical $C(R_4)R_5$, $R_5$ represents a radical —$NR_{12}R_{13}$, $R_{12}$ represents a hydrogen atom and $R_{13}$ represents a hydrogen atom or an alkyl radical, on a halide Hal-$R_{12}$ in which $R_{12}$ has the same meanings as above.

This reaction is generally carried out in an inert solvent such as dimethylformamide, in the presence of an alkali metal carbonate such as sodium carbonate or potassium carbonate or a trialkylamine such as triethylamine or pyridine, at a temperature between 0° C. and the boiling point of the reaction medium.

The halides Hal-$R_{12}$ are commercially available or those for which $R_{12}$ represents a radical -alk-$NR_7R_{15}$ may be prepared by the action of a dihalide Hal-alk-Hal, for which Hal represents a halogen atom and alk represents an alkyl radical, on an amine HN—$R_7R_{15}$ in which $R_7$ and $R_{15}$ have the same meanings as in formula (I), in an inert solvent such as dimethylformamide, in the presence of an acid acceptor such as a nitrogen-containing base, at a temperature between 0° and 25° C. Those for which $R_{12}$ represents a radical -alk-$COOR_7$ may be obtained by the action of a derivative Hal-alk-Hal, in which Hal represents a halogen atom and alk represents an alkyl radical, on an alkali metal cyanide (sodium cyanide or potassium cyanide), in a water-alcohol mixture, at a temperature between 0° C. and the boiling point of the reaction medium, followed by the action of a strong acid such as HCl, optionally in the presence of a lower aliphatic alcohol, at a temperature between 0° C. and the boiling point of the reaction medium.

The compounds of formula (I) for which R represents a radical $C(R_4)R_5$, in which $R_5$ represents a radical —$NR_{12}R_{13}$, $R_{12}$ has the same meanings as in formula (I) and $R_{13}$ represents an alkyl radical, may be prepared by the action of a corresponding compound of formula (I), for which R represents a radical $C(R_4)R_5$, $R_5$ represents a radical —$NR_{12}R_{13}$, $R_{12}$ has the same meanings as in formula (I) and $R_{13}$ represents a hydrogen atom, on a derivative of formula Hal-alk in which Hal represents a halogen atom and alk represents an alkyl radical.

This reaction is carried out in an inert solvent such as dimethylformamide, in the presence of an acid acceptor such as a nitrogen-containing organic base (pyridine or a trialkylamine, for instance triethylamine), at a temperature between 0° C. and the boiling point of the reaction medium.

The halides Hal-alk are commercially available or may be obtained from the corresponding alcohols by application or adaptation of the methods described by R. C. Larock, "Comprehensive Organic Transformations", Ed. VCH, page 345 and 353 (1989).

The compounds of formula (I) for which R represents a radical $C(R_4)R_5$, in which $R_5$ represents a radical —$COOR_7$, -alk-CN, -alk-Het", -alk-$COOR_7$ -alk-CO—$NR_7R_{15}$ or -alk-$NR_7R_{15}$ or a phenylalkyl radical in which the phenyl ring is substituted with one or more substituents chosen from halogen atoms and alkyl, alkoxy, nitro, amino, hydroxyl, cyano, -alk-$NH_2$, —$COOR_7$ and -alk-$COOR_7$ radicals, may be prepared by the action of a derivative of formula (IX), in which $R_1$ and $R_2$ have the same meanings as in formula (I), Rc represents an alkyl, -alk-Het or -alk-Het" radical or a phenylalkyl radical in which the phenyl ring is optionally substituted with one or more substituents chosen from halogen atoms and alkyl, alkoxy, nitro, amino, hydroxyl, cyano, -alk-$NH_2$, —$COOR_7$ and -alk-$COOR_7$ radicals in which alk, Het, Het" and $R_7$ have the same meanings as in formula (I) and Rb represents a hydrogen atom, on a halide HalRe in which Re represents a radical —$COOR_7$ in which $R_7$ represents an alkyl, -alk-CN, -alk-Het", -alk-$COOR_7$, -alk-CO—$NR_7R_{15}$ or -alk-$NR_7R_{15}$ radical or a phenylalkyl radical in which the phenyl ring is substituted with one or more substituents chosen from halogen atoms and alkyl, alkoxy, nitro, amino, hydroxyl, cyano, -alk-$NH_2$, —$COOR_7$ and -alk-$COOR_7$ radicals in which alk, Het", $R_{15}$ and $R_7$ have the same meanings as in formula (I), optionally followed by hydrolysis of the compound for which $R_5$ represents a radical —$COOR_7$ or -alk-$COOR_7$ in which $R_7$ represents an alkyl radical, to give the corresponding compound for which $R_7$ is a hydrogen atom.

This reaction is generally carried out in an inert solvent such as dioxane or dimethylformamide, in the presence of an alkali metal hydride such as sodium hydride or potassium hydride, at a temperature in the region of 20° C. The hydrolysis is preferably carried out using a base such as an alkali metal hydroxide (sodium hydroxide or potassium hydroxide for example), in a water-alcohol (ethanol for example) mixture, at a temperature of approximately 20° to 30° C.

The derivatives Hal-Re are commercially available or those for which Re represents a radical -alk-Het" or a phenylalkyl radical in which the phenyl is substituted may be prepared from the corresponding alcohols by adaptation of the methods described by R. C. Larock,, "Comprehensive Organic Transformations", Ed. VCH, page 353 (1989). Those for which Re represents a radical -alk-$NR_7R_{15}$ may be obtained by the action of Hal-alk-Hal, in which Hal represents a halogen atom and alk represents an alkyl radical, on an amine $HNR_7R_{15}$ in which $R_7$ and $R_{15}$ have the same meanings as in formula (I), in an inert solvent such as dimethylformamide, in the presence of an organic base (triethylamine or pyridine), at a temperature between 0° C. and the boiling point of the reaction medium. Those for which Re represents a radical -alk-CO—$NR_7R_{15}$ may be obtained by the action of an amine $HNR_7R_{15}$, in which $R_7$ and $R_{15}$ have the same meanings as in formula (I), on a derivative Hal-alk-CO-Hal in which Hal represents a halogen atom and alk represents an alkyl radical, in an inert solvent such as tetrahydrofuran or dimethylformamide, in the presence of a base such as a trialkylamine or pyridine, at a temperature between 0° C. and the boiling point of the reaction medium. The derivatives Hal-alk-CO-Hal are commercially available or may be obtained by halogenation of the corresponding acids using a halogenating agent such as thionyl chloride, in an inert solvent such as 1,2-dichloroethane, at a temperature in the region of 60° C. The corresponding acids Hal-alk-COOH may be obtained by the action of an alkali metal cyanide on a derivative Hal-alk-Hal in which Hal represents a halogen atom and alk represents an alkyl radical, in a water-alcohol mixture, at a temperature between 0° C. and the boiling point of the reaction medium, followed by the action of a strong acid such as hydrochloric acid, in an aqueous medium, at a temperature between 0° C. and the boiling point of the reaction medium. Those for which Re represents a radical —COOR, may be obtained by application or adaptation of the methods described in Houben-Weyl, vol. 8, page 102 (1952).

The derivatives of formula (IX) for which $R_1$ and $R_2$ have the same meanings as in formula (I), Rc represents an alkyl (2–6C), -alk-Het or -alk-Het" radical or a phenylalkyl radical in which the phenyl ring is optionally substituted with one or more substituents chosen from halogen atoms and alkyl, alkoxy, nitro, amino, hydroxyl, cyano, -alk-$NH_2$, —$COOR_7$ and -alk-$COOR_7$ radicals and Rb represents a hydrogen atom, may be obtained by hydrogenation of the derivatives of formula:

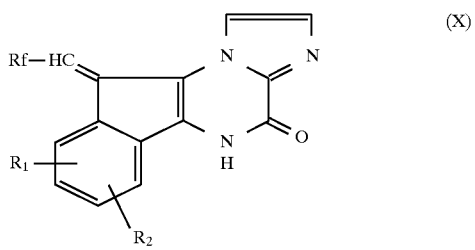

in which $R_1$ and $R_2$ have the same meanings as in formula (I) and Rf represents an alkyl (1–5C), -alk(1–5C)-Het, Het, -alk(1–5C)-Het" or Het" radical or a phenyalkyl radical in which the phenyl ring is optionally substituted with one or more substituents chosen from halogen atoms and alkyl, alkoxy, nitro, amino, hydroxyl, cyano, -alk-$NH_2$, —$COOR_1$ and -alk-$COOR_7$ radicals or a phenyl radical which is optionally substituted with one or more substituents chosen from halogen atoms and alkyl, alkoxy, nitro, amino, hydroxyl, cyano, -alk-$NH_2$, —$COOR_7$ and -alk-$COOR_7$ radicals in which alk, Het, Het" and $R_7$ have the same meanings as in formula (I).

This reaction is carried out using hydrogen at a pressure of 1 to 20 bar, in the presence of a hydrogenation catalyst such as palladium-on-charcoal, palladium hydroxide or palladium (N. Rico et al., Nouveau Journal de Chimie, 10, 1, 25 (1986)), in an inert solvent such as dimethylformamide, acetic acid, ethyl acetate, an alcohol (methanol or ethanol for example) or a mixture of these solvents, at a temperature between 20° and 60° C. or by adaptation of the method of L. M. Strawn et al., J. Med. Chem., 32, 2104 (1989) which consists in reacting the compound to be reduced with hydroxylamine sulphate and $H_2NOSO_3H$ in water, at a pH between 6 and 7, at a temperature of 10° C.

The derivatives of formula (X) may be obtained by the action of a derivative of formula (III), in which $R_1$ and $R_2$ have the same meanings as in formula (I) on a derivative OHC—Rf for which Rf has the same meanings as in formula (X).

This reaction is generally carried out in an inert solvent such as dimethylformamide, 1,2-dimethoxyethane, an alcohol (methanol or ethanol for example) or a mixture of these solvents, in the presence of a base such as sodium hydroxide, potassium hydroxide or a strong organic base such as 1,8-diazabicyclo[5.4.0]undec-7-ene, at a temperature between 20° and 100° C., or is carried out in dimethyl sulphoxide, in the presence of an alkali metal hydride such as sodium hydride, at a temperature in the region of 20° C., or is carried out in the presence of tetrabutylammonium bromide and a base such as an alkali metal hydroxide (sodium hydroxide or potassium hydroxide for example), in dimethyl sulphoxide, at a temperature between 20° C. and the boiling point of the reaction medium.

The derivatives OHC—Rf are commercially available or may be obtained by the methods described above for the preparation of the derivatives OHC—$R_{10}$.

The derivatives of formula (IX), for which $R_1$ and $R_2$ have the same meanings as in formula (I), Rc represents an alkyl (1C) radical and Rb represents a hydrogen atom, may be obtained by reduction of a derivative of formula (X) for which $R_1$ and $R_2$ have the same meanings as in formula (I) and Rf represents a hydroxyl or dialkylamino radical.

This reduction is carried out using hydrogen at a pressure of 1 to 20 bar, in the presence of a hydrogenation catalyst such as palladium-on-charcoal, palladium hydroxide or palladium (N. Rico et al., Nouveau Journal de Chimie, 10, 1, 25 (1986)), in an inert solvent such as dimethylformamide, acetic acid, ethyl acetate, an alcohol (methanol or ethanol for example) or a mixture of these solvents, at a temperature between 20° and 60° C. or by adaptation of the method of L. M. Strawn et al., J. Med. Chem., 32, 2104 (1989) which consists in reacting the compound to be reduced with hydroxylamine sulphate and $H_2NOSO_3H$ in water, at a pH between 6 and 7, at a temperature of 10° C.

The derivatives of formula (X) for which Rf represents a hydroxyl radical may be obtained by hydrolysis of the derivatives of formula (X) corresponding for which Rf represents a dialkylamino radical.

This reaction is preferably carried out using an acid such as hydrochloric acid in an aqueous medium, at a temperature between 20° and 40° C.

The derivatives of formula (X) for which Rf represents a dialkylamino radical may be obtained by the action of a derivative of formula (III) on a derivative HC(Rg)(Rh)Ri for which Ri and Rh represent a dialkylamino radical and Rg represents an alkoxy radical such as tert-butoxy, or alternatively Rg, Rh and Ri represent dialkylamino radicals.

This reaction is generally carried out in an inert solvent such as dimethylformamide, at a temperature between 20° and 40° C.

The derivatives HC(Rg)(Rh)Ri may be obtained by application or adaptation of the method described by H. Bredereck, Liebigs Ann. Chem., 762, 62 (1972).

The compounds of formula (I) for which R represents a radical $C(R_4)R_5$, in which $R_5$ represents either a radical -alk-Het" in which Het" represents a 1-imidazolyl radical, or $R_5$ represents a radical -alk-$NR_7R_{15}$, may also be prepared by the action of trimethylchlorosilane on a derivative of formula (IX) in which $R_1$ and $R_2$ have the same meanings as in formula (I), Rc represents an alkyl, -alk-Het or -alk-Het" radical or a phenylalkyl radical in which the phenyl ring is optionally substituted with one or more substituents chosen from halogen atoms and alkyl, alkoxy, nitro, amino, hydroxyl, cyano, -alk-$NH_2$, —$COOR_7$ and -alk-$COOR_7$ radicals in which alk, Het, Het" and $R_7$ have the same meanings as in formula (I) and Rb represents a hydrogen atom, followed by the action of a derivative Hal-alk-Hal in which Hal represents a halogen atom and alk represents an alkyl radical, and the action of imidazole or of an amine $HNR_7R_{15}$ in which $R_7$ and $R_{15}$ have the same meanings as in formula (I).

This reaction is generally carried out in an inert solvent such as dimethylformamide, in the presence of an alkali metal hydride such as sodium hydride or potassium hydride, at a temperature in the region of 20° C. The reaction of the amine and of imidazole is carried out in the same medium generally in the presence of sodium iodide, at a temperature in the region of 50° C.

The compounds of formula (I) for which R represents a radical $C(R_4)R_5$, in which $R_5$ represents a radical -alk-$COOR_7$ in which $R_7$ represents a hydrogen atom, may also be prepared by hydrolysis of a corresponding compound of formula (I) for which R represents a radical $C(R_4)R_5$ in which $R_5$ represents a radical -alk-CN.

This hydrolysis is generally carried out using an inorganic acid (HCl or HBr for example), in an aqueous medium, at a temperature between 30° C. and the boiling point of the reaction medium.

The compounds of formula (I) for which R represents a radical $C(R_4)R_5$, in which $R_5$ represents a radical -alk(2–6C) OH, may be prepared by the action of oxalyl chloride on a corresponding compound of formula (I) for which R represents a radical $C(R_4)R_5$ in which $R_5$ represents a radical -alk-$COOR_7$ and $R_7$ represents a hydrogen atom, followed by reduction.

This reaction is carried out in an inert solvent such as dioxane. The reduction is preferably carried out using sodium borohydride, in an inert solvent such as dimethylformamide, at a temperature between 10° and 20° C.

The compounds of formula (I) for which R represents a radical $C(R_4)R_5$, in which $R_5$ represents a radical -alk(1C) OH, may be prepared by the action of trimethylsilane chloride on a derivative of formula (IX) for which $R_1$ and $R_2$ have the same meanings as in formula (I), Rb represents a hydrogen atom and Rc represents an alkyl, -alk-Het or -alk-Het" radical or a phenylalkyl radical in which the phenyl ring is optionally substituted with one or more substituents chosen from halogen atoms and alkyl, alkoxy, nitro, amino, hydroxyl, cyano, -alk-$NH_2$, —$COOR_7$ and -alk-$COOR_7$ radicals for which alk, Het, Het" and $R_7$ have the same meanings as in formula (I), followed by the action of trioxane.

This reaction is generally carried out in an inert solvent such as dimethylformamide, in the presence of sodium hydride, followed by reaction with trioxane at a temperature between 0° and 25° C.

The compounds of formula (I) for which R represents a radical $C(R_4)R_5$, in which $R_5$ represents a radical —NH—CHO, or alternatively for which R represents a radical CH—$R_6$ and $R_6$ represents a radical —NH—CHO, may be prepared by the action of a derivative of formula (IX), in which $R_1$ and $R_2$ have the same meanings as in formula (I), Rb represents a hydrogen atom or an alkyl, -alk-Het or -alk-Het" radical or a phenylalkyl radical in which the phenyl ring is optionally substituted with one or more substituents chosen from halogen atoms and alkyl, alkoxy, nitro, amino, hydroxyl, cyano, -alk-$NH_2$, —$COOR_1$ and -alk-$COOR_7$ radicals and Rc represents an amino radical, on $CH_3COOCHO$.

This reaction is preferably carried out in an inert solvent such as formic acid, in the presence of sodium acetate, at a temperature in the region of 20° C.

The compounds of formula (I) for which R represents a radical $C(R_4)R_5$, in which $R_5$ represents a radical —NH—$COOR_{17}$, —NH—CO-Het, —NH—CO-Het", —NH—CO-alk-$COOR_7$ or —NH—CO-alk-$NR_7R_{15}$, a radical —NH—CO—Ar in which Ar is optionally substituted, a radical —NH—CO-alk-Ar in which Ar is optionally substituted, a radical —NH—CO—C(Ar) ($CF_3$)$OCH_3$, —NH—CO-alk-Het, —NH—CO-alk-Het", —NH—CO-alk, —NH—CO-cycloalkyl or —NH—$SO_2R_{19}$, or alternatively R represents a radical CH—$R_6$ and $R_6$ represents a radical —NH—$COOR_{17}$, a radical —NH—CO—Ar in which Ar is substituted, a radical —NH—CO-Het, —NH—CO-Het", —NH—CO-alk-Het, —NH—CO-alk-Het", —NH—CO-alk(2–6C)—$NH_2$, —NH—CO-alk-N(alk)$_2$, —NH—CO-alk-NH-alk or —NH—CO-alk(2–6C)—$COOR_7$, a radical —NH—CO-alk-Ar in which Ar is optionally substituted or a radical —NH—CO—C(Ar)($CF_3$)$OCH_3$ may be prepared by the action of a derivative of formula (IX), for which $R_1$ and $R_2$ have the same meanings as in formula (I), Rb represents a hydrogen atom or an alkyl, -alk-Het or -alk-Het" radical or a phenylalkyl radical in which the phenyl ring is optionally substituted with one or more substituents chosen from halogen atoms and alkyl, alkoxy, nitro, amino, hydroxyl, cyano, -alk-$NH_2$, —$COOR_7$ and -alk-$COOR_7$ radicals in which $R_7$, Het, Het" and alk have the same meanings as in formula (I) and Rc represents an amino radical, on a derivative Hal-Rj in which Hal represents a halogen atom and Rj represents a radical —$COOR_{17}$, —CO-Het, —CO-Het", —CO-alk-$COOR_7$ or —CO-alk-$NR_7R_{15}$, a radical —CO—Ar which is optionally substituted with one or more substituents chosen from halogen atoms and alkyl, alkoxy, nitro, amino, hydroxyl, cyano, -alk-$NH_2$, —$COOR_7$ and -alk-$COOR_7$ radicals, a radical —CO-alk-Ar in which Ar is optionally substituted with one or more substituents chosen from halogen atoms and alkyl, alkoxy, nitro, amino, hydroxyl, cyano, -alk-$NH_2$, —$COOR_7$ and -alk-$COOR_7$ radicals, a radical —CO—C(Ar)($CF_3$)$OCH_3$, —CO-alk-Het, —CO-alk-Het", —CO-alk, —COcycloalkyl, —$SO_2R_{19}$, —CO-alk(2–6C)—$NH_2$, —CO-alk-N(alk)$_2$, —CO-alk-NH-alk or —CO-alk(2–6C)—$COOR_7$ in which $R_7$, $R_{15}$, $R_{17}$, $R_{19}$, Het, Het", Ar and alk have the same meanings as in formula (I).

This reaction is generally carried out in an inert solvent such as dimethylformamide or dimethyl sulphoxide, in the presence of an acid acceptor such as a trialkylamine (triethylamine for example) or an alkali metal hydride (sodium hydride for example), at a temperature in the region of 20° C.

The derivatives Hal-Rj are commercially available or those for which Rj represents a radical —CO-Het, —CO-Het", —CO-alk-Het, —CO-alk-Het", —CO-cycloalkyl, —CO-alk-$COOR_7$ or —CO-alk-$NR_7R_{15}$, a radical —CO-alk-Ar in which Ar is optionally substituted with one or more substituents chosen from halogen atoms and alkyl, alkoxy, nitro, amino, hydroxyl, cyano, -alk-$NH_2$, —$COOR_7$ and -alk-$COOR_7$ radicals may be obtained from the corresponding carboxylic acids by the action of a phosphorus halide ($PCl_5$ or $POCl_3$ for example), preferably in the phosphorus halide, optionally in the presence of an inert solvent such as dichloromethane, at a temperature between 20° C. and the boiling point of the reaction medium.

The compounds of formula (I) for which R represents a radical $C(R_4)R_5$ or CH—$R_6$, in which $R_5$ and $R_6$ represent a radical —NH—$COOR_{17}$ and $R_{17}$ represents a tert-butyl radical, may also be prepared by the action of a derivative of formula (IX), for which $R_1$ and $R_2$ have the same meanings as in formula (I), Rb represents a hydrogen atom or an alkyl, -alk-Het or -alk-Het" radical or a phenylalkyl radical in which the phenyl ring is optionally substituted with one or more substituents chosen from halogen atoms and alkyl, alkoxy, nitro, amino, hydroxyl, cyano, -alk-$NH_2$, —$COOR_7$ and -alk-$COOR_7$ radicals in which $R_7$, Het, Het" and alk have the same meanings as in formula (I) and Rc represents an amino radical, on di-tert-butyl dicarbonate.

This reaction is generally carried out in an inert solvent such as dimethylformamide, at a temperature in the region of 60° C.

The compounds of formula (I) for which R either represents a radical $C(R_4)R_5$ or represents a radical CH—$R_6$, in which $R_5$ and $R_6$ represent either a radical —NH—CO—Ar in which Ar is substituted with a radical —$COOR_7$ and $R_7$ represents a hydrogen atom, or $R_5$ and $R_6$ represent a radical —NH—CO-alk-$COOR_7$ in which alk represents an alkyl radical containing 1 to 3 carbon atoms in a straight chain or a radical —$CH_2$—$C(CH_3)_2$—$CH_2$—, —$CH_2$—$CH_2$—C $(CH_3)_2$— or —$CH_2$—$C(CH_3)_2$— and $R_7$ represents a hydrogen atom, may also be prepared by the action of a derivative of formula (IX), for which $R_1$ and $R_2$ have the same meanings as in formula (I), Rb represents a hydrogen atom or an alkyl, -alk-Het or -alk-Het" radical or a phenylalkyl radical in which the phenyl ring is optionally substituted with one or more substituents chosen from halogen atoms and alkyl, alkoxy, nitro, amino, hydroxyl, cyano, -alk-$NH_2$, —$COOR_7$ and -alk-$COOR_7$ radicals in which $R_7$, Het, Het" and alk have the same meanings as in formula (I) and Rc represents an amino radical, on an anhydride of formulae:

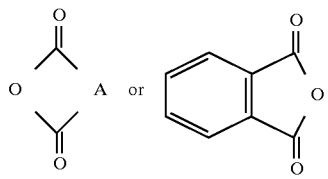

in which A represents an alkyl radical (1–3C in a straight chain) or a radical —$CH_2$—$C(CH_3)_2$—$CH_2$—, —$CH_2$—$CH_2$—$C(CH_3)_2$— or —$CH_2$—$C(CH_3)_2$—.

This reaction is generally carried out in an inert solvent such as acetic acid, at a temperature in the region of 20° C.

The compounds of formula (I) for which R represents a radical $C(R_4)R_5$, in which $R_5$ represents a radical —NH—CO-Het, —NH—CO-Het", —NH—CO-alk-$COOR_7$ or —NH—CO-alk-$NR_7R_{15}$, a radical —NH—CO—Ar in which Ar is optionally substituted, a radical —NH—CO-alk-Ar in which Ar is optionally substituted, a radical —NH—CO-alk-Het, —NH—CO-alk-Het", —NH—CO-alk or —NH—CO-cycloalkyl, may also be prepared by the action of a corresponding compound of formula (I) for which R represents a radical $C(R_4)R_5$, in which $R_5$ represents a radical —$NR_{12}R_{13}$, $R_{12}$ and $R_{13}$ are hydrogen atoms, on a derivative HOOC-Rk in which Rk represents a radical -Het, -Het", -alk-$COOR_7$ or -alk-$NR_7R_{15}$, a phenyl radical which is optionally substituted with one or more substituents chosen from halogen atoms and alkyl, alkoxy, nitro, amino, hydroxyl, cyano, -alk-$NH_2$, —$COOR_7$ and -alk-$COOR_7$ radicals, a phenylalkyl radical in which the phenyl is optionally substituted with one or more substituents chosen from halogen atoms and alkyl, alkoxy, nitro, amino, hydroxyl, cyano, -alk-$NH_2$, —$COOR_7$ and -alk-$COOR_7$ radicals, a radical -alk-Het, -alk-Het", -alkyl or -cycloalkyl in which $R_7$, $R_{15}$, Het, Het", Ar and alk have the same meanings as in formula (I).

This reaction is generally carried out in an inert solvent such as dimethylformamide, in the presence of hydroxybenzotriazole, 1-(3-dimethylaminopropyl)-3-ethylcarbodiimide and an organic base such as a trialkylamine (triethylamine for example), at a temperature between 0° and 5° C.

The acids HOOC-Rk are commercially available or those for which Rk represents Het may be obtained by the processes described above for the preparation of the acids HOOC-Het" starting with the corresponding heterocycles.

The compounds of formula (I) for which R represents a radical $C(R_4)R_5$, in which $R_5$ represents a 1-pyrrolyl radical which is optionally substituted with a radical —$COOR_7$, or alternatively for which R represents a radical CH—$R_6$, $R_6$ represents a 1-pyrrolyl radical which is optionally substituted with a radical —$COOR_7$, may be prepared by the action of a derivative of formula (IX), for which $R_1$ and $R_2$ have the same meanings as in formula (I), Rb represents a hydrogen atom or an alkyl, -alk-Het or -alk-Het" radical or a phenylalkyl radical in which the phenyl ring is optionally substituted with one or more substituents chosen from halogen atoms and alkyl, alkoxy, nitro, amino, hydroxyl, cyano, -alk-$NH_2$, —COOR739 and -alk-$COOR_7$ radicals and Rc represents an amino radical, on a derivative of formula:

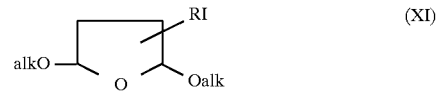

in which alk represents an alkyl radical, RI represents a hydrogen atom or a radical —$COOR_7$ and $R_7$ has the same meanings as in formula (I), optionally followed by hydrolysis of the ester, to give the compounds for which $R_7$ represents a hydrogen atom.

This reaction is generally carried out in an inert solvent such as acetic acid, at the boiling point of the reaction medium, optionally in the presence of an acid acceptor such as sodium acetate. The hydrolysis is generally carried out using an alkali metal hydroxide (sodium hydroxide or potassium hydroxide for example), in a lower aliphatic alcohol such as propanol, at the boiling point of the reaction medium.

The derivatives of formula (XI) may be obtained by application or adaptation of the methods described by J. Fakstorp et al., J. Am. Chem. Soc., 72, 869 (1950) and N. Clauson-Kaas et al., Acta Chem. Scan., 6, 551 (1952), STIBOR et al., Collect. Czech. Chem. Commun., 47 (12), 3261 (1992).

The compounds of formula (I) for which R represents a radical $C(R_4)R_5$, in which $R_5$ represents a radical —NH—CO—NH-alk-Ar in which Ar is optionally substituted, a radical —NH—CO—NH-Het, —NH—CO—NH-Het", —NH—CO—NH-alk-Het or —NH—CO—NH-alk-Het", a radical —NH—CO—NH—Ar in which Ar is optionally substituted, a radical —NH—CO—NH-alk or —NH—CO—$NH_2$, or alternatively for which R represents a radical CH—$R_6$, $R_6$ represents represents a radical —NH—CO—NH-alk-Ar in which Ar is optionally substituted, a radical —NH—CO—NH-Het", —NH—CO—NH-alk-Het or —NH—CO—NH-alk-Het" or a radical —NH—CO—NH—Ar in which Ar is substituted, may be prepared by the action of a derivative of formula (IX), for which $R_1$ and $R_2$ have the same meanings as in formula (I), Rb represents a hydrogen atom or an alkyl, -alk-Het or -alk-Het" radical or a phenylalkyl radical in which the phenyl ring is optionally substituted with one or more substituents chosen from halogen atoms and alkyl, alkoxy, nitro, amino, hydroxyl, cyano, -alk-$NH_2$, —$COOR_7$ and -alk-$COOR_7$ radicals and Rc represents an amino radical, on a derivative O=C=N-Rm in which Rm represents a trimethylsilyl, alkyl, -Het or -Het" radical, a phenylalkyl radical in which the phenyl is optionally substituted with one or more substituents chosen from halogen atoms and alkyl, alkoxy, nitro, amino, hydroxyl, cyano, -alk-$NH_2$, —$COOR_7$ and -alk-$COOR_7$ radicals, a radical -alk-Het or -alk-Het" or a phenyl radical which is optionally substituted with one or more substituents chosen from halogen atoms and alkyl, alkoxy, nitro, amino, hydroxyl, cyano, -alk-$NH_2$, —$COOR_7$ and -alk-$COOR_7$ radicals in which alk, Ar, Het, Het" and $R_7$ have the same meanings as in formula (I).

This reaction is generally carried out in an inert solvent such as dimethylformamide, tetrahydrofuran or dioxane, at a temperature between 20° C. and the boiling point of the reaction medium. For the compounds for which $R_5$ represents a radical —NH—CO—$NH_2$, this reaction is followed by hydrolysis of the silyl derivative previously obtained, using an aqueous solution, at a temperature between 20° and 50° C.

The derivatives O═C═N-Rm are commercially available or may be obtained by the action of phosgene on the corresponding primary amine, by adaptation of the methods described by R. L. Shriner et al., Organic Synth., II, 453; G. M. Dyon, Organic Synth., I, 165; R. J. Slocompie et al., J. Am. Chem. Soc., 72, 1888 (1950) and S. Patai, "The chemistry of cyanates and their thio derivatives", Ed. John Wiley and Sons, page 619 (1977). The corresponding primary amines are commercially available or those for which RI represents a radical Het or Het" or a phenyl radical which is optionally substituted, may be obtained by application or adaptation of the methods described by B. A. Tertov et al., Khim. Geterotsikl. Soedin, II, 1552 (1972) and R. C. Larock, "Comprehensive Organic Transformations", Ed. VCH, page 399, which consists in reacting the organolithium reagent or the organomagnesium reagent of the heterocycle or of the optionally substituted benzene in question with $PhN_3$, in the presence of acetic acid, $(PhO)_2PON_3$, $NH_2OCH_3$ or $N_3CH_2Si(CH_3)_3$. The organolithium reagents or the organomagnesium reagents may be obtained by application or adaptation of the methods described by D. L. Comins et al., J. Org. Chem., 52, 104 (1987); N. Furukana et al., Tetrahedron Lett., 28 (47), 5845 (1987); A. R. Katritzky et al., Org. Prep. Procedure Int., 20 (6), 585 (1988); A. J. Clarke et al., Tetrahedron Lett., 27, 2373 (1974) and A. W. Gschwen et al., Organic Reaction, 26, 1 (1979). The amines for which Rm represents a radical -alk-Het or -alk-Het" or a phenylalkyl radical in which the phenyl is optionally substituted, are commercially available or are obtained from the corresponding halides by the action of $NaN(SiCH_3)_3$ or the potassium salt of phthalimide, in an inert solvent such as dimethylformamide, in the presence of an organic base such as a trialkylamine or pyridine, at a temperature between 0° C. and the boiling point of the reaction medium, followed by hydrolysis either in an acidic medium (HCl or HBr for example), at a temperature between 20° C. and the boiling point of the reaction medium, or by the action of hydrazine, in an aliphatic alcohol, at the boiling point of the reaction medium. The amines $H_2N$-alk-Ar in which Ar is optionally substituted may also be obtained by application or adaptation of the methods described by J. K. King et al., J. Am. Chem. Soc., 114, 3028 (1992); B. M. Adger et al., Tetrahedron Lett., 25 (45), 5219 (1984) and R. Scarpati et al., Gazz. Chim. Ital., 97 (5), 654 (1967).

The compounds of formula (I) for which R represents a radical CH—$R_6$ and $R_6$ represents a radical —COOalk may be prepared by the action of an inorganic acid on a derivative of formula:

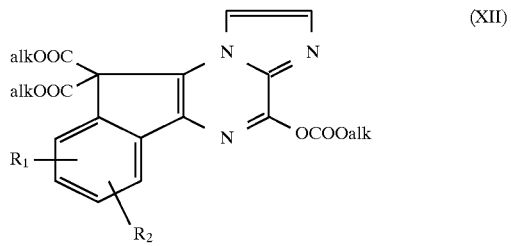

(XII)

in which $R_1$ and $R_2$ have the same meanings as in formula (I) and alk represents alkyl radicals.

This reaction is preferably carried out in an inert solvent such as tetrahydrofuran, at a temperature in the region of 20° C. Hydrochloric acid as a 1N aqueous solution is preferably used as inorganic acid.

The derivatives of formula (XII) may be obtained by the action of a derivative of formula (III) on a halide Hal-COOalk in which alk represents an alkyl radical.

This reaction is generally carried out in an inert solvent such as dioxane, in the presence of an alkali metal hydride such as sodium hydride, at a temperature between 20° C. and the boiling point of the reaction medium.

The compounds of formula (I) for which R represents a radical CH—$R_6$ and $R_6$ represents a radical -alk-COO$R_7$ may be prepared by reduction of a compound of formula (X) in which $R_1$ and $R_2$ have the same meanings as in formula (I) and Rf represents a radical -alk(1–5C)—COO$R_7$ or —COO$R_7$ in which alk has the same meanings as in formula (I) and $R_7$ represents an alkyl radical, optionally followed by saponification of the ester thus obtained.

This reduction is carried out using hydrogen at a pressure of 1 to 20 bar, in the presence of a hydrogenation catalyst such as palladium-on-charcoal, palladium hydroxide or palladium (N. Rico et al., Nouveau Journal de Chimie, 10, 1, 25 (1986)), in an inert solvent such as dimethylformamide, acetic acid, ethyl acetate, an alcohol (methanol or ethanol for example) or a mixture of these solvents, at a temperature between 20° and 60° C., or by adaptation of the method of L. M. Strawn et al., J. Med. Chem., 32, 2104 (1989) which consists in reacting the compound with hydroxylamine sulphate and $H_2NOSO_3H$ in water, at a pH between 6 and 7, at a temperature of 10° C. The saponification is carried out by any known method and preferably using an acid such as hydrochloric acid, in dimethyl sulphoxide, at a temperature of 20° to 30° C., or using trifluoroacetic acid at a temperature in the region of 20° to 30° C.

The derivatives of formula (X) for which $R_1$ and $R_2$ have the same meanings as in formula (I) and Rf represents a radical —COO$R_7$, in which $R_7$ has the same meanings as in formula (I), may be obtained by the action of a derivative of formula (III) on an alkyl glyoxylate, optionally followed by a saponification.

This reaction is carried out in an inert solvent such as dimethyl sulphoxide, in the presence of an alkali metal hydride (sodium hydride or potassium hydride for example), at a temperature in the region of 20° C. The saponification is carried out by any known method and preferably using an acid such as hydrochloric acid, in dimethyl sulphoxide, at a temperature of 20° to 30° C., or using trifluoroacetic acid at a temperature in the region of 20° to 30° C.

The derivatives of formula (X) for which $R_1$ and $R_2$ have the same meanings as in formula (I) and Rf represents a radical -alk-COO$R_7$ may be obtained in a similar manner to the process described above for the compounds of formula (X) for which Rf represents an alkyl radical, or alternatively by reduction of the derivatives of formula (X) for which Rf represents a carboxyl radical, using iron and hydrochloric acid, optionally in the presence of a lower aliphatic alcohol, at a temperature between 20° C. and the boiling point of the reaction medium.

The compounds of formula (I) for which R represents a radical $C(R_4)R_5$ or CH—$R_6$, $R_5$ and $R_6$ represent a radical -alk-CO—$NR_7R_{15}$, may also be prepared by the action of a corresponding compound of formula (I), for which R represents a radical $C(R_4)R_5$ or CH—$R_6$ and $R_5$ and $R_6$ represent a radical -alk-COO$R_7$, on an amine $HNR_7R_{15}$ in which $R_7$ and $R_{15}$ have the same meanings as in formula (I).

When the acid is used, the process is performed in the presence of a coupling agent used in peptide chemistry such as a carbodiimide (for example N,N'-dicyclohexylcarbodiimide) or N,N'-carbonyldiimidazole, in an inert solvent such as an ether (tetrahydrofuran or dioxane for example), an amide (dimethylformamide) or a chlorinated solvent (methylene chloride, 1,2-dichloroethane or chloroform for example), at a temperature between 0° C. and the reflux temperature of the reaction mixture. When an ester is used, the process is then performed either in an organic medium, optionally in the presence of an acid acceptor such as a nitrogen-containing organic base (trialkylamine, pyridine, 1,8-diazabicyclo[5.4.0]undec-7-ene or 1,5-diazabicyclo[4.3.0]-non-5-ene for example), in a solvent as mentioned above, or a mixture of these solvents, at a temperature between 0° C. and the reflux temperature of the reaction mixture, or the process is performed in a two-phase aqueous-organic medium in the presence of an alkali metal or alkaline-earth metal base (sodium hydroxide or potassium hydroxide) or of a carbonate or bicarbonate of an alkali metal or alkaline-earth metal, at a temperature between 0° and 40° C.

The compounds of formula (I) for which R represents a radical CH—$R_6$, $R_6$ represents a radical -alk(1C)—CO—N$R_7R_{15}$ and $R_1$ and $R_{15}$ represent hydrogen atoms, may be prepared by hydrogenation of a derivative of formula (X) in which $R_1$ and $R_2$ have the same meanings as in formula (I) and Rf represents a radical —CONH$_2$.

This reaction is generally carried out either using hydrogen, in an inert solvent such as dimethylformamide, in the presence of a hydrogenation catalyst such as palladium-on-charcoal or palladium, at a temperature in the region of 20° to 30° C., or is carried out by adaptation of the method of L. M. Strawn et al., J. Med. Chem., 32, 2104 (1989) which consists in reacting the compound with hydroxylamine sulphate and H$_2$NOSO$_3$H in water, at a pH between 6 and 7, at a temperature of 10° C.

The derivatives of formula (X) in which $R_1$ and $R_2$ have the same meanings as in formula (I) and Rf represents a radical —CONH$_2$ may be obtained by the action of ammonia on a corresponding derivative of formula (X) for which Rf represents a radical —COOalk, under the conditions described by D. T. Mowry et al., Organic Synth., IV, 486 or J. Kleinberg et al., Organic Synth., III, 516.

The compounds of formula (I) for which R represents a radical CH—$R_6$, $R_6$ represents a radical -alk-Het" or a phenylalkyl radical in which the phenyl ring is substituted, may be prepared by hydrogenation of a corresponding compound of formula (I) for which R represents a radical C=$R_3$, $R_3$ represents a radical CH—$R_{10}$ and $R_{10}$ represents a radical -Het", -alk(1–5C)-Het", a phenyl radical substituted with one or more substituents chosen from halogen atoms and alkyl, alkoxy, nitro, amino, hydroxyl, cyano, -alk-NH$_2$, —COOR$_7$ and -alk-COOR$_7$ radicals, or a phenylalkyl(1–5C) radical in which the phenyl ring is substituted with one or more substituents chosen from halogen atoms and alkyl, alkoxy, nitro, amino, hydroxyl, cyano, -alk-NH$_2$, —COOR$_7$ and -alk-COOR$_7$ radicals in which alk and R$_7$ have the same meanings as in formula (I).

This reduction is carried out using hydrogen at a pressure of 1 to 20 bar, in the presence of a hydrogenation catalyst such as palladium-on-charcoal, palladium hydroxide or palladium (N. Rico et al., Nouveau Journal de Chimie, 10, 1, 25 (1986)), in an inert solvent such as dimethylformamide, acetic acid, ethyl acetate, an alcohol (methanol or ethanol for example) or a mixture of these solvents, at a temperature between 20° and 60° C., or by adaptation of the method of L. M. Strawn et al., J. Med. Chem., 32, 2104 (1989) which consists in reacting the compound with hydroxylamine sulphate and H$_2$NOSO$_3$H in water, at a pH between 6 and 7, at a temperature of 10° C.

The compounds of formula (I) for which R represents a radical CH—$R_6$ and $R_6$ represent a radical —$R_{14}$—COOR$_7$, may be prepared by the action of a derivative of formula (III), in which $R_1$ and $R_2$ have the same meanings as in formula (I), on a derivative of formula OHC-alk(0–5C)—COOR, in which alk represents an alkyl radical and $R_7$ has the same meanings as in formula (I).

This reaction is preferably carried out in an inert solvent such as dimethyl sulphoxide, in the presence of an alkali metal hydride such as sodium hydride, at a temperature in the region of 20° C.

The derivatives of formula OHC-alk(0–5C)—COOR$_7$ may be prepared by application or adaptation of the method described by L. A. Carpino, J. Org. Chem., 29, 2820 (1964).

The compounds of formula (I) for which R represents a radical CH—$R_6$ and $R_6$ represents a radical —CO—COOR$_7$ may be prepared by oxidation of a corresponding compound of formula (I) for which R represents a radical CH—$R_6$, $R_6$ represents a radical —$R_{14}$—COOR$_7$ in which $R_7$ represents a hydrogen atom and $R_{14}$ represents a radical —CHOH—, optionally followed by an esterification.

This oxidation is preferably carried out using potassium permanganate in 3N sodium hydroxide solution, at a temperature in the region of −3° C. or using platinum-on-charcoal, in 2N sodium hydroxide solution, at a temperature of 70° C. The esterification is carried out by any known esterification method. The esterification is preferably performed using an alcohol, in the presence of an acid such as hydrochloric acid or sulphuric acid, at the boiling point of the reaction medium.

The compounds of formula (I) for which R represents a radical CH—$R_6$ and $R_6$ represents a radical —NH—CO—Ar in which Ar is substituted, a radical —NH—CO-Het, —NH—CO-Het", —NH—CO-alk-Het, —NH—CO-alk-Het", —NH—CO-alk(2–6C)—NH$_2$, —NH—CO-alk-N(alk)$_2$, —NH—CO-alk-NH-alk or —NH—CO-alk(2–6C)—COOR$_7$ or a radical —NH—CO-alk-Ar in which Ar is optionally substituted, may also be prepared by the action of a derivative of formula (IX), for which $R_1$ and $R_2$ have the same meanings as in formula (I), Rb represents a hydrogen atom and Rc represents an amino radical, on a derivative HOOC-Rn in which Rn represents a phenyl radical which is substituted with one or more substituents chosen from halogen atoms and alkyl, alkoxy, nitro, amino, hydroxyl, -alk-NH$_2$, —COOR$_7$ and -alk-COOR$_7$ radicals, a radical -Het, -Het", -alk-Het, -alk-Het", -alk(2–6C)—COOR$_7$, -alk(2–6C)—NH$_2$, -alk-N(alk)$_2$ or -alk-NH-alk or a phenylalkyl radical in which the phenyl is optionally substituted with one or more substituents chosen from halogen atoms and alkyl, alkoxy, nitro, amino, hydroxyl, -alk-NH$_2$, —COOR$_7$ and -alk-COOR$_7$ radicals in which alk, Het, Het", $R_7$, $R_{15}$ and Ar have the same meanings as in formula (I).

This reaction is generally carried out in an inert solvent such as dimethylformamide, in the presence of hydroxybenzotriazole, 1-(3-dimethylaminopropyl)-3-ethylcarbodiimide and an organic base such as a trialkylamine (triethylamine for example), at a temperature between 0° and 5° C.

The compounds of formula (I) for which $R_1$ represents a hydrogen atom and $R_2$ represents a nitro radical in position -8 may also be prepared by nitration of the corresponding compounds of formula (I) for which $R_1$ and $R_2$ are hydrogen atoms.

This nitration is preferably carried out using KNO$_3$, in a concentrated sulphuric medium, at a temperature between 0° and 25° C.

The compounds of formula (I) for which $R_1$ represents a hydrogen atom and $R_2$ represents an amino radical may also be prepared by reducing a corresponding compound of formula (I) for which $R_1$ represents a hydrogen atom and $R_2$ represents a nitro radical.

This reduction is carried out by any process for the reduction of a nitro group to an amino group.

Preferably, the reduction is carried out using hydrogen, at a pressure of 1 to 5 bar, in the presence of a hydrogenation catalyst such as palladium-on-charcoal, in an inert solvent such as dimethylformamide, acetic acid, ethyl acetate, an alcohol or a mixture of these solvents; or using $SnCl_2$, in a concentrated hydrochloric acid medium, at a temperature between 20° and 60° C.

The compounds of formula (I) for which $R_1$ represents a hydrogen atom and $R_2$ represents a radical —NH—CO—$NR_8R_9$ or —NH—CS—$NR_8R_9$ and $R_9$ represents a hydrogen atom, may also be prepared by the action of a corresponding compound of formula (I), for which $R_1$ represents a hydrogen atom and $R_2$ represents an amino radical, on a derivative Ro=C=N=Rp in which Ro represents an oxygen or sulphur atom and Rp represents a trimethylsilyl, alkyl, -alk-$COOR_7$, -alk-Het, -alk-Het" or -alk$NR_9R_7$ radical or a phenylalkyl radical in which the phenyl is optionally substituted with one or more substituents chosen from halogen atoms and alkyl, alkoxy, nitro, amino, hydroxyl, cyano, -alk-$NH_2$, —$COOR_7$ and -alk-$COOR_7$ radicals, a phenyl radical which is optionally substituted with one or more substituents chosen from halogen atoms and alkyl, alkoxy, nitro, amino, hydroxyl, cyano, -alk-$NH_2$, —$COOR_7$ and -alk-$COOR_7$ radicals, or a radical Het or Het", in which alk, Het, Het", $R_7$ and $R_9$ have the same meanings as in formula (I).

This reaction is generally carried out in an inert solvent such as dimethylformamide, tetrahydrofuran or dioxane, at a temperature between 20° C. and the boiling point of the reaction medium, followed by hydrolysis of the silyl derivative, to give the compound for which $R_8$ represents a hydrogen atom, by means of an aqueous solution, at a temperature between 20° and 50° C.

The derivatives Ro=C=N=Rp for which Ro represents a sulphur atom are commercially available or may be obtained by the action of thiophosgene on the corresponding primary amine, by application or adaptation of the methods described by R. L. Shriner et al., Organic Synth., II, 453; G. M. Dyon, Organic Synth., I, 165; R. J. Slocompie et al., J. Am. Chem. Soc., 72, 1888 (1950) and S. Patai, "The chemistry of cyanates and their thio derivatives", Ed. John Wiley and Sons, page 619 (1977).

The compounds of formula (I) for which $R_6$ represents a phenylalkyl radical in which the phenyl is substituted with an amino radical may also be prepared by hydrolysis of a corresponding compound of formula (I) for which $R_6$ represents a phenylalkyl radical in which the phenyl is substituted with an acetylamino radical.

This reaction is generally carried out using an alkali metal hydroxide (sodium hydroxide or potassium hydroxide for example) in an aqueous medium, at a temperature between 20° C. and the boiling point of the reaction medium.

The compounds of formula (I) for which $R_6$ represents a phenylalkyl radical in which the phenyl is substituted with an acetylamino radical may also be prepared by acetylation of a corresponding compound of formula (I) for which $R_6$ represents a phenylalkyl radical in which the phenyl is substituted with an amino radical.

This acetylation is preferably carried out using acetic anhydride, in acetic acid, at a temperature in the region of 80° C.

The compounds of formula (I) containing a carboxyl radical may also be prepared by hydrolysis of the corresponding compounds of formula (I) containing an alkoxycarbonyl radical.

This reaction is generally carried out using an alkali metal hydroxide (sodium hydroxide or potassium hydroxide for example) in an aqueous medium, at a temperature between 20° C. and the boiling point of the reaction medium.

It is understood by those skilled in the art that, in order to carry out the processes according to the invention which are described above, it may be necessary to introduce protecting groups for the amino, hydroxyl and carboxyl functions in order to avoid side reactions. These groups are those which it is possible to remove without affecting the rest of the molecule.

Examples of protecting groups for the amino function which may be mentioned are tert-butyl carbamate or methyl carbamate, which may be regenerated using iodotrimethylsilane. Examples of protecting groups for the hydroxyl function which may be mentioned are triethylsilyl and benzyl. Examples of protecting groups for the carboxyl functions which may be mentioned are esters (methoxymethyl ester, tetrahydropyranyl ester and benzyl ester for example), oxazoles and 2-alkyl-1,3-oxazolines. Other protecting groups which may be used are described in W. Greene et al., Protecting Groups in Organic Synthesis, second edition, 1991, John Wiley & Sons.

The compounds of formula (I) may be purified by the usual known methods, for example by crystallization, chromatography or extraction.

The enantiomers of the compounds of formula (I) for which R represents a radical $C(R_4)R_5$ or CH—$R_6$ may be obtained by resolution of the racemates, for example by chromatography on a chiral column according to W. H. Pirckle et al., Asymmetric Synthesis, vol. 1, Academic Press (1983) or by synthesis starting with chiral precursors.

The diastereoisomers of the compounds of formula (I) for which R represents a radical $C(R_4)R_5$ or CH—$R_6$ containing one or more chiral carbons and the various E and Z isomers of the compounds of formula (I) may be separated by the usual known methods, for example by crystallization or chromatography.

The compounds of formula (I) containing a basic residue may optionally be converted into addition salts with an inorganic or organic acid by the action of such an acid in an organic solvent such as an alcohol, a ketone, an ether or a chlorinated solvent.

The compounds of formula (I) containing an acidic residue may optionally be converted into metal salts or into addition salts with nitrogen-containing bases according to methods which are known per se. These salts may be obtained by the action of a metal base (an alkali metal or alkaline-earth metal base for example), ammonia, an amine or an amine salt on a compound of formula (I), in a solvent. The salt formed is separated out by the usual methods.

These salts also form part of the invention.

Examples of pharmaceutically acceptable salts which may be mentioned are the addition salts with inorganic or organic acids (such as acetate, propionate, succinate, benzoate, fumarate, maleate, oxalate, methanesulphonate, isethionate, theophyllineacetate, salicylate, methylenebis-β-oxynaphthoate, hydrochloride, sulphate, nitrate and phosphate), salts with alkali metals (sodium, potassium or lithium) or with alkaline-earth metals (calcium or magnesium), the ammonium salt, salts of nitrogen-containing bases (ethanolamine, trimethylamine, methylamine, benzylamine, N-benzyl-β-phenethylamine, choline, arginine, leucine, lysine or N-methylglucamine).

The compounds of formula (I) exhibit advantageous pharmacological properties. These compounds are antagonists of the α-amino-3-hydroxy-5-methyl-4-isoxazolepropionic acid (AMPA) receptor, also known as the quisqualate receptor.

Moreover, the compounds of formula (I) are non-competitive antagonists of the N-methyl-D-aspartate (NMDA) receptor and, more particularly, they are ligands for the glycine regulatory sites of the NMDA receptor.

They are thus useful compounds for treating or preventing all ischaemias (such as focal or global ischaemia) following cerebrovascular accidents, a cardiac arrest, arterial hypotension, a cardiac or pulmonary surgical intervention or severe hypoglycaemia. They are also useful in the treatment of the effects due to anoxia, whether perinatal or following drowning or cerebrospinal lesions. These compounds may also be used for treating or preventing the development of neurodegenerative diseases, Huntington's chorea, Alzheimer's disease, amyotrophic lateral sclerosis, olivopontocerebellar atrophy and Parkinson's disease. These compounds may also be used with respect to epilepsy-causing and/or convulsive manifestations, for the treatment of cerebral or spinal trauma, trauma associated with degeneration of the inner ear (R. Pujol et al., Neuroreport, 3, 299–302 (1992)) or of the retina (J. L. Monsinger et al., Exp. Neurol., 113, 10–17 (1991)), of anxiety (Kehne et al., Eur. J. Pharmacol., 193, 283 (1991)), of depression (Trullas et al., Eur. J. Pharmacol., 185, 1 (1990)), of schizophrenia (Reynolds, Tips, 13, 116 (1992)), of Tourette's syndrome, or of hepatic encephalopathy, as analgesics (Dickenson et al., Neurosc. Letters, 121, 263 (1991)), as anti-inflammatory agents (Sluta et al., Neurosci. Letters, 149, 99–102 (1993)) as anti-anorectic agents (Sorrels et al., Brain Res., 572, 265 (1992)), as anti-migraine and anti-emetic agents and for treating poisoning by neurotoxins or by other NMDA-receptor agonist substances, as well as for treating neurological disorders associated with viral diseases such as AIDS (Lipton et al., Neuron, 7, 111 (1991)), rabies, measles and tetanus (Bagetta et al., Br. J. Pharmacol., 101, 776 (1990)). These compounds are also useful for the prevention of the withdrawal symptoms associated with drugs and alcohol and for inhibition of the addiction to and the dependency on opiates. They may also be used in the treatment of deficiencies associated with mitochondrial anomalies such as mitochondrial myopathy, Leber's syndrome, Wernicke's encephalopathy, Rett's syndrome, homocysteinaemia, hyperprolinaemia, hydroxybutyric aminoaciduria, saturnine encephalopathy (chronic lead poisoning), and sulphite oxidase deficiency.

The affinity of the compounds of formula (I) towards the AMPA receptor was determined by studying the antagonism of the specific binding of [$^3$H]-AMPA to rat cerebral cortex membranes (Honore et al., Neuroscience Letters, 54, 27 (1985)). [$^3$H]-AMPA is incubated in the presence of 0.2 mg of proteins at 4° C. for 30 minutes in 10 MM KH$_2$PO$_4$ buffer, 100 mM KSCN, pH 7.5. The non-specific binding is determined in the presence of 1 mM L-glutamate. The bound radioactivity is separated by filtration on PHARMACIA filters (Printed Filtermate A). The inhibitory activity of these products is less than or equal to 100 $\mu$M.

The affinity of the compounds of formula (I) for the glycine site bound to the NMDA receptor was determined by studying the antagonism of the specific binding of [$^3$H]-DCKA to rat cerebral cortex membranes according to the method described by T. Canton et al., J. Pharm. Pharmacol., 44, 812 (1992). [$^3$H]-DCKA (20 nM) is incubated in the presence of 0.1 mg of proteins at 4° C. for 30 minutes in 50 mM HEPES buffer, pH 7.5. The non-specific binding is determined in the presence of 1 mM glycine. The bound radioactivity is separated by filtration on Whatman GF/B filters. The inhibitory activity of these products is less than or equal to 100 $\mu$M.

The compounds of formula (I) exhibit low toxicity. Their LD$_{50}$ is greater than 50 mg/kg via the IP route in mice.

Particularly advantageous compounds are those for which (a) R represents a radical C=R$_3$ in which R$_3$ represents a radical NO-alk, CHR$_{10}$ or NR$_7$, R$_1$ represents a hydrogen or halogen atom or a radical NH—CO—NR$_8$R$_9$ and R$_2$ represents a hydrogen atom, (b) R represents a radical C(R$_4$)R$_5$, R$_4$ represents an alkyl radical or a phenylalkyl radical in which the phenyl ring is optionally substituted with one or more substituents chosen from halogen atoms and alkyl, alkoxy, nitro, amino, hydroxyl, cyano, -alk-NH$_2$, —COOR$_7$ and -alk-COOR$_7$ radicals, R$_5$ represents a radical —NR$_{12}$R$_{13}$, —NH—COOR$_{17}$, -alk-COOR$_7$, -alk-CONR$_7$R$_{15}$, -alk-NR$_7$R$_{15}$, -alk-OH, -alk-CN or -alk-Het", a phenylalkyl radical in which the phenyl ring is substituted with one or more substituents chosen from halogen atoms and alkyl, alkoxy, nitro, amino, hydroxyl, cyano, -alk-NH$_2$, —COOR$_7$ and -alk-COOR$_7$ radicals, a radical —NH—CO—Ar in which Ar is optionally substituted with one or more substituents chosen from halogen atoms and alkyl, alkoxy, nitro, amino, hydroxyl, cyano, -alk-NH$_2$, —COOR$_7$ and -alk-COOR$_7$ radicals, a radical —NH—CO-alk-COOR$_7$, a 1-pyrrolyl radical which is optionally substituted with a radical —COOR$_7$ or a radical —NH—COalk, and (c) R represents a radical CH—R, in which R$_6$ represents —NH—CHO, —COOalk, -alk-COOR$_7$, phenylalkyl in which the phenyl ring is substituted with one or more substituents chosen from halogen atoms and alkyl, alkoxy, nitro, amino, acetylamino, hydroxyl, cyano, -alk-NH$_2$, —COOR$_7$ and -alk-COOR$_7$ radicals, —R$_{14}$—COOR$_7$, —NH—COOR$_{17}$, —NH—CO-Het, —NH—CO-Het", —NH—CO-alk(2–6C)—COOR$_7$, —NH—CO-alk-N(alk)$_2$, —NH—CO-alk-Ar in which Ar is optionally substituted with one or more substituents chosen from halogen atoms and alkyl, alkoxy, nitro, amino, hydroxyl, cyano, -alk-NH$_2$, —COOR$_7$ and -alk-COOR$_7$ radicals, —NH—CO—C(Ar)(CF$_3$)OCH$_3$, -alk-Het" or 1-pyrrolyl which is optionally substituted with a radical —COOR$_7$. The substituent R, is preferably in position -7 or -8.

Among these compounds, the following compounds are especially advantageous:

ethyl 5H,10H-imidazo[1,2-a]indeno[1,2-e]pyrazin-4-one-10-carboxylate, 10-imino-5H,10H-imidazo[1,2-a]indeno[1,2-e]pyrazin-4-one, 10-(2-carboxybenzyl)-5H,10H-imidazo[1,2-a]indeno-[1,2-e]pyrazin-4-one, 10-(4-carboxybenzyl)-5H,10H-imidazo[1,2-a]indeno-[1,2-e)pyrazin-4-one, 10-(3-carboxybenzylidene)-5H,10H-imidazo[1,2-a]-indeno[1,2-e]pyrazin-4-one, 10-(3-carboxybenzyl)-5H,10H-imidazo[1,2-a]indeno-[1,2-e]pyrazin-4-one, 10-(4-acetylaminobenzyl)-5H,10H-imidazo[1,2-a]indeno-(1,2-e]pyrazin-4-one, 10-(4-aminobenzyl)-5H,10H-imidazo[1,2-a]indeno-[1,2-e]pyrazin-4-one, 10-[(1-methylimidazol-2-yl)methylene]-5H,10H-imidazo-[1,2-a]indeno[1,2-e]pyrazin-4-one, 10-[(1-methylimidazol-2-yl)methyl]-5H,10H-imidazo-[1,2-a]indeno[1,2-e]pyrazin-4-one, 10-(tert-butoxycarbonylmethyl)-5H,10H-imidazo-[1,2-a]indeno[1,2-e]pyrazin-4-one, 10-(carboxymethyl)-5H,10H-imidazo[1,2-a]indeno-[1,2-e]pyrazin-4-one, 10-(carboxymethylene)-5H,10H-imidazo[1,2-a]indeno-[1,2-e]pyrazin-4-one, 5-(4-hydroxyimidazo[1,2-a]indeno[1,2-e]pyrazin-10-ylidene)pentanoic acid, 10-(1-carboxy-1-hydroxymethyl)-8-(3-methylureido)-5H,10H-imidazo[1,2-a]indeno(1,2-e)pyrazin-4-one, 10-nicotinoylamino-5H,10H-imidazo[1,2-a]indeno-[1,2-e]pyrazin-4-one,
methyl 3-[10-(4,5-dihydro-4-oxo-10H-imidazo[1,2-a]indeno[1,2-e]pyrazinyl)aminocarbonyl]propionate,
10-(3-diethylaminopropionamido)-5H,10H-imidazo-[1,2-a]indeno[1,2-e]pyrazin-4-one,
10-formamido-5H,10H-imidazo[1,2-a]indeno[1,2-e]pyrazin-4-one,
(10R)-10[(R)-α-methoxy-α-trifluoromethylphenyl-acetamido]-5H,10H-imidazo[1,2-a]indeno[1,2-e]pyrazin-4-one,
(10S)-10[(R)-α-methoxy-α-trifluoromethylphenyl-acetamido]-5H,10H-imidazo[1,2-a]indeno[1,2-e]pyrazin-4-one,
10-(4-phenylbutyramido)-5H,10H-imidazo[1,2-a]-indeno[1,2-e]pyrazin-4-one,
10-phenylacetamido-5H,10H-imidazo[1,2-a]indeno-[1,2-e]pyrazin-4-one,
tert-butyl N-[10-(4,5-dihydro-4-oxo-10H-imidazo-[1,2-a]indeno[1,2-e]pyrazinyl)]carbamate,
10-(1-pyrrolyl)-5H,10H-imidazo[1,2-a]indeno-[1,2-e]pyrazin-4-one,
methyl 1-[10-(4,5-dihydro-4-oxo-10H-imidazo-[1,2-a]indeno[1,2-e]pyrazinyl)]pyrrole-2-carboxylate,
10-methoxyimino-5H,10H-imidazo[1,2-a]indeno-[1,2-e]pyrazin-4-one,
10-acetamido-10-methyl-5H,10H-imidazo[1,2-a]-indeno[1,2-e]pyrazin-4-one,
10-amino-10-methyl-5H,10H-imidazo[1,2-a]-indeno[1,2-e]pyrazin-4-one,
10-(4-imidazolylmethyl)-5H,10H-imidazo[1,2-a]-indeno[1,2-e]pyrazin-4-one,
10-[3-(imidazol-1-yl)propyl]-10-methyl-5H,10H-imidazo[1,2-a]indeno[1,2-e]pyrazin-4-one,
10-[4-(imidazol-1-yl)butyl]-10-methyl-5H,10H-imidazo[1,2-a]indeno[1,2-e]pyrazin-4-one,
10-amino-10-methyl-8-(3-methylureido)-5H,10H-imidazo[1,2-a]indeno[1,2-e]pyrazin-4-one,
10-(carboxymethylene)-8-(3-methylureido)-5H,10H-imidazo[1,2-a]indeno[1,2-e]pyrazin-4-one,
10-amino-10-methyl-8-(3-n-propylureido)-5H,10H-imidazo[1,2-a]indeno[1,2-e]pyrazin-4-one,
10-amino-10-benzyl-7-chloro-5H,10H-imidazo-[1,2-a]indeno[1,2-e]pyrazin-4-one,
10-(3-aminobenzyl)-5H,10H-imidazo[1,2-a]-indeno[1,2-e]pyrazin-4-one,
10-(3-aminobenzylidene)-5H,10H-imidazo[1,2-a]indeno-[1,2-e]pyrazin-4-one,
10-(3-acetylaminobenzyl)-5H,10H-imidazo[1,2-a]-indeno[1,2-e]pyrazin-4-one,
10-(3-methoxycarbonylbenzylidene)-5H,10H-imidazo-[1,2-a]indeno[1,2-e]pyrazin-4-one,
10-amino-10-phenethyl-5H,10H-imidazo[1,2-a]indeno-[1,2-e]pyrazin-4-one,
10-amino-10-(3-phenylpropyl)-5H,10H-imidazo-[1,2-a]indeno[1,2-e]pyrazin-4-one,
10-acetamido-10-(4-phenylbutyl)-5H,10H-imidazo-[1,2-a]indeno[1,2-e]pyrazin-4-one,
5-(10-methyl-4,5-dihydro-4-oxo-10H-imidazo-[1,2-a]indeno[1,2-e]pyrazin-10-yl)valeric acid,
10-(3-dimethylaminopropyl)-10-methyl-5H,10H-imidazo[1,2-a]indeno[1,2-e]pyrazin-4-one,
4-(10-methyl-4,5-dihydro-4-oxo-10H-imidazo-[1,2-a]indeno[1,2-e]pyrazin-10-yl)butyronitrile,
4-(10-methyl-4,5-dihydro-4-oxo-10H-imidazo-[1,2-a]indeno[1,2-e]pyrazin-10-yl)butyric acid,
10-hydroxymethyl-10-methyl-5H,10H-imidazo-[1,2-a]indeno[1,2-e]pyrazin-4-one,
4-(10-methyl-4,5-dihydro-4-oxo-10H-imidazo-[1,2-a]indeno[1,2-e]pyrazin-10-yl)butyramide,
(10-methyl-4,5-dihydro-4-oxo-10H-imidazo-[1,2-a]indeno[1,2-e]pyrazin-10-yl)acetic acid,
3-(10-methyl-4,5-dihydro-4-oxo-10H-imidazo-[1,2-a]indeno[1,2-e]pyrazin-10-yl)propionitrile,
3-(10-methyl-4,5-dihydro-4-oxo-10H-imidazo-[1,2-a]indeno[1,2-e]pyrazin-10-yl)propionic acid,
10-(4-hydroxybutyl)-10-methyl-5H,10H-imidazo-[1,2-a]indeno[1,2-e]pyrazin-4-one,
10-methyl-10-[(1-methylimidazol-2-yl)methyl]-5H,10H-imidazo[1,2-a]indeno[1,2-e]pyrazin-4-one,
10-[(1-methylimidazol-5-yl)methylene]-5H,10H-imidazo[1,2-a]indeno[1,2-e]pyrazin-4-one,
10-[(1-methylimidazol-5-yl)methyl]-5H,10H-imidazo[1,2-a]indeno[1,2-e]pyrazin-4-one,
8-[3-(3-fluorophenyl)ureido]-10-(carboxymethyl)-5H,10H-imidazo[1,2-a]indeno[1,2-e]pyrazin-4-one,
[8-(3-methylureido)-4,5-dihydro-4-oxo-10H-imidazo[1,2-a]indeno[1,2-e]pyrazin-10-yl]acetic acid,
(+)-(8-(3-methylureido)-4,5-dihydro-4-oxo-10H-imidazo[1,2-a]indeno[1,2-e]pyrazin-10-yl)acetic acid,
(−)-[8-(3-methylureido)-4,5-dihydro-4-oxo-10H-imidazo[1,2-a]indeno[1,2-e]pyrazin-10-yl]acetic acid,
(4,5-dihydro-4-oxo-10H-imidazo[1,2-a]indeno-[1,2-e]pyrazin-10-yl)glycolic acid,
10-methyl-10-(1-pyrrolyl)-5H,10H-imidazo[1,2-a]-indeno[1,2-e]pyrazin-4-one,
3-[10-(10-methyl-4-oxo-4,5-dihydro-10H-imidazo-[1,2-a]indeno[1,2-e]pyrazinyl)aminocarbonyl]-2,2-dimethylpropionic acid,
4-[10-(10-methyl-4-oxo-4,5-dihydro-10H-imidazo-[1,2-a]indeno[1,2-e]pyrazinyl)aminocarbonyl]-3,3-dimethylbutyric acid,
1-[10-(4-oxo-4,5-dihydro-10H-imidazo[1,2-a]indeno-[1,2-e]pyrazinyl)]pyrrole-2-carboxylic acid,
3-[10-(4-oxo-4,5-dihydro-10H-imidazo[1,2-a]indeno-[1,2-e]pyrazinyl)aminocarbonyl]propionic acid,
10-amino-10-ethyl-5H, 10H-imidazo[1,2-a]indeno-[1,2-e]pyrazin-4-one,
10-amino-10-benzyl-5H,10H-imidazo[1,2-a]indeno-[1,2-e]pyrazin-4-one,
10-amino-10-propyl-5H,10H-imidazo[1,2-a]indeno-[1,2-e]pyrazin-4-one,
3-[10-(10-methyl-4-oxo-4,5-dihydro-10H-imidazo-[1,2-a]indeno[1,2-e]pyrazinyl)aminocarbonyl]propionic acid,
tert-butyl N-[10-(10-methyl-4-oxo-4,5-dihydro-10H-imidazo[1,2-a]indeno[1,2-e]pyrazinyl)]carbamate,
4-[10-(10-methyl-4-oxo-4,5-dihydro-10H-imidazo-[1,2-a]indeno[1,2-e]pyrazinyl)aminocarbonyl]butyric acid,
10-amino-10-isopropyl-5H,10H-imidazo[1,2-a]indeno-[1,2-e]pyrazin-4-one,
10-amino-10-butyl-5H,10H-imidazo[1,2-a]indeno-[1,2-e]pyrazin-4-one,
10-methyl-10-methylamino-5H,10H-imidazo[1,2-a]-indeno[1,2-e]pyrazin-4-one,
10-carboxymethylene-7-chloro-5H-imidazo[1,2-a)-indeno[1,2-e]pyrazin-4-one,
10-amino-10-methyl-8-(3-methylureido)-5H,10H-imidazo[1,2-a]indeno[1,2-e]pyrazin-4-one and its enantiomers,
10-(1,3-dimethyl-1H-pyrazole-4-methylene)-5H,10H-imidazo[1,2-a]indeno[1,2-e]pyrazin-4-one, and their salts.

Particularly advantageous compounds with respect to the AMPA receptor are the following compounds:
ethyl 5H,10H-imidazo[1,2-a]indeno-[1,2-e]pyrazin-4-one-10-carboxylate, 10-imino-5H,10H-imidazo[1,2-a]indeno[1,2-e]pyrazin-4-one,
10-(2-carboxybenzyl)-5H,10H-imidazo[1,2-a]indeno-[1,2-e]pyrazin-4-one,
10-(4-carboxybenzyl)-5H,10H-imidazo[1,2-a]indeno-[1,2-e]pyrazin-4-one,
10-(3-carboxybenzylidene)-5H,10H-imidazo[1,2-a]-indeno[1,2-e]pyrazin-4-one,
10-(3-carboxybenzyl)-5H,10H-imidazo[1,2-a]indeno-[1,2-e]pyrazin-4-one,
10-(4-aminobenzyl)-5H,10H-imidazo[1,2-a]indeno-[1,2-e]pyrazin-4-one,
10-[(1-methylimidazol-2-yl)methylene]-5H,10H-imidazo[1,2-a]indeno[1,2-e]pyrazin-4-one,
10-(carboxymethyl)-5H,10H-imidazo[1,2-a]indeno-[1,2-e]pyrazin-4-one,
10-(carboxymethylene)-5H,10H-imidazo[1,2-a]indeno-[1,2-e]pyrazin-4-one,
5-(4-hydroxyimidazo[1,2-a]indeno[1,2-e]pyrazin-10-ylidene]pentanoic acid,
10-(1-carboxy-1-hydroxymethyl)-8-(3-methylureido)-5H,10H-imidazo[1,2-a]indeno[1,2-e]pyrazin-4-one,
10-nicotinoylamino-5H,10H-imidazo[1,2-a]indeno[1,2-e]pyrazin-4-one,
methyl 3-[10-(4,5-dihydro-4-oxo-10H-imidazo-[1,2-a]indeno[1,2-e]pyrazinyl)aminocarbonyl]propionate,
10-(3-diethylaminopropionamido)-5H,10H-imidazo-[1,2-a]indeno[1,2-e]pyrazin-4-one,
10-formamido-5H,10H-imidazo[1,2-a]indeno[1,2-e]-pyrazin-4-one,
(10R)-10[(R)-α-methoxy-α-trifluoromethylphenylacetamido]-5H,10H-imidazo[1,2-a]-indeno[1,2-e]pyrazin-4-one,
(10S)-10[(R)-α-methoxy-α-trifluoromethylphenyl-acetamido]-5H,10H-imidazo[1,2-a]indeno[1,2-e]pyrazin-4-one,
10-phenylacetamido-5H,10H-imidazo[1,2-a]indeno-[1,2-e]pyrazin-4-one,
tert-butyl N-[10-(4,5-dihydro-4-oxo-10H-imidazo-[1,2-a]indeno[1,2-e]pyrazinyl)]carbamate,
10-(1-pyrrolyl)-5H,10H-imidazo[1,2-a]indeno[1,2-e]-pyrazin-4-one,
methyl 1-[10-(4,5-dihydro-4-oxo-10H-imidazo-[1,2-a]indeno[1,2-e]pyrazinyl)]pyrrole-2-carboxylate,
10-methoxyimino-5H,10H-imidazo[1,2-a)indeno-[1,2-e]pyrazin-4-one,
10-acetamido-10-methyl-5H,10H-imidazo[1,2-a]-indeno[1,2-e]pyrazin-4-one,
10-amino-10-methyl-5H,10H-imidazo[1,2-a]indeno-[1,2-e]pyrazin-4-one,
10-(4-imidazolylmethyl)-5H,10H-imidazo[1,2-a]-indeno[1,2-e]pyrazin-4-one,
10-amino-10-methyl-8-(3-methylureido)-5H,10H-imidazo[1,2-a]indeno[1,2-e]pyrazin-4-one,
10-(carboxymethylene)-8-(3-methylureido)-5H,10H-imidazo[1,2-a]indeno[1,2-e]pyrazin-4-one,
10-amino-10-methyl-8-(3-n-propylureido)-5H,10H-imidazo[1,2-a]indeno[1,2-e]pyrazin-4-one,
10-(3-aminobenzyl)-5H,10H-imidazo[1,2-a]indeno-[1,2-e]pyrazin-4-one,
10-(3-aminobenzylidene)-5H-imidazo[1,2-a]indeno-(1,2-e]pyrazin-4-one,
10-(3-acetylaminobenzyl)-5H,10H-imidazo[1,2-a]-indeno[1,2-e]pyrazin-4-one,
10-(3-methoxycarbonylbenzylidene)-5H-imidazo[1,2-a]-indeno[1,2-e]pyrazin-4-one,
10-amino-10-(3-phenylpropyl)-5H,10H-imidazo[1,2-a]-indeno[1,2-e]pyrazin-4-one,
5-(10-methyl-4,5-dihydro-4-oxo-10H-imidazo[1,2-a]-indeno[1,2-e]pyrazin-10-yl)valeric acid,
4-(10-methyl-4,5-dihydro-4-oxo-10H-imidazo[1,2-a]-indeno-[1,2-e]pyrazin-10-yl)butyronitrile,
4-(10-methyl-4,5-dihydro-4-oxo-10H-imidazo[1,2-a]-indeno[1,2-e]pyrazin-10-yl)butyric acid,
10-hydroxymethyl-10-methyl-5H,10H-imidazo[1,2-a]-indeno[1,2-e]pyrazin-4-one,
(10-methyl-4,5-dihydro-4-oxo-10H-imidazo[1,2-a]-indeno[1,2-e]pyrazin-10-yl)acetic acid,
3-(10-methyl-4,5-dihydro-4-oxo-10H-imidazo[1,2-a]-indeno[1,2-e]pyrazin-10-yl)propionitrile,
3-(10-methyl-4,5-dihydro-4-oxo-10H-imidazo[1,2-a]-indeno[1,2-e]pyrazin-10-yl)propionic acid,
10-methyl-10-[(1-methylimidazol-2-yl)methyl]-5H,10H-imidazo[1,2-a]indeno[1,2-e]pyrazin-4-one,
10-[(1-methylimidazol-5-yl)methylene]-5H,10H-imidazo[1,2-a]indeno[1,2-e]pyrazin-4-one,
10-[(1-methylimidazol-5-yl)methyl]-5H,10H-imidazo[1,2-a]indeno[1,2-e]pyrazin-4-one,
8-[3-(3-fluorophenyl)ureido]-10-(carboxymethyl)-5H,10H-imidazo[1,2-a]indeno[1,2-e]pyrazin-4-one,
[8-(3-methylureido)-4,5-dihydro-4-oxo-10H-imidazo-[1,2-a]indeno[1,2-e]pyrazin-10-yl]acetic acid,
(+)-[8-(3-methylureido)-4,5-dihydro-4-oxo-10H-imidazo[1,2-a]indeno[1,2-e]pyrazin-10-yl]acetic acid,
(−)-[8-(3-methylureido)-4,5-dihydro-4-oxo-10H-imidazo[1,2-a]indeno[1,2-e]pyrazin-10-yl]acetic acid,
(4,5-dihydro-4-oxo-10H-imidazo[1,2-a]indeno-[1,2-e]pyrazin-10-yl)glycolic acid,
10-methyl-10-(1-pyrrolyl)-5H,10H-imidazo-[1,2-a]indeno[1,2-e]pyrazin-4-one,
1-[10-(4-oxo-4,5-dihydro-10H-imidazo[1,2-a]-indeno[1,2-e]pyrazinyl)]pyrrole-2-carboxylic acid,
3-[10-(4-oxo-4,5-dihydro-10H-imidazo-[1,2-a]indeno[1,2-e]pyrazinyl)aminocarbonyl]propionic acid,
10-amino-10-ethyl-5H,10H-imidazo[1,2-a]indeno[1,2-e]-pyrazin-4-one,
10-amino-10-benzyl-5H,10H-imidazo[1,2-a]indeno-[1,2-e]pyrazin-4-one,
10-amino-10-propyl-5H,10H-imidazo[1,2-a]indeno-[1,2-e]-pyrazin-4-one,
3-[10-(10-methyl-4-oxo-4,5-dihydro-10H-imidazo-[1,2-a]indeno[1,2-e]pyrazinyl)aminocarbonyl]propionic acid,
tert-butyl N-[10-(10-methyl-4-oxo-4,5-dihydro-10H-imidazo[1,2-a]indeno[1,2-e]pyrazinyl)]carbamate,
4-[10-(10-methyl-4-oxo-4,5-dihydro-10H-imidazo-[1,2-a]indeno[1,2-e]pyrazinyl)aminocarbonyl]butyric acid,
10-amino-10-isopropyl-5H,10H-imidazo[1,2-a]indeno-[1,2-e]pyrazin-4-one,
10-amino-10-butyl-5H,10H-imidazo[1,2-a]indeno-[1,2-e]pyrazin-4-one,
10-methyl-10-methylamino-5H,10H-imidazo[1,2-a]-indeno[1,2-e]pyrazin-4-one,
10-amino-10-methyl-8-(3-methylureido)-5H,10H-imidazo[1,2-a]indeno[1,2-e]pyrazin-4-one and its enantiomers,
10-(1,3-dimethyl-1H-pyrazole-4-methylene)-5H,10H-imidazo[1,2-a]indeno[1,2-e]pyrazin-4-one, and their salts.

Particularly advantageous compounds with respect to the glycine regulatory site of the NMDA receptor are the following compounds:
ethyl 5H,10H-imidazo[1,2-a]indeno[1,2-e]pyrazin-4-one-10-carboxylate,
10-imino-5H,10H-imidazo[1,2-a]indeno[1,2-e]pyrazin-4-one,
10-(2-carboxybenzyl)-5H,10H-imidazo[1,2-a]indeno-[1,2-e]pyrazin-4-one, 10-(4-carboxybenzyl)-5H,10H-imidazo[1,2-a]indeno-[1,2-e]pyrazin-4-one,
10-(3-carboxybenzylidene)-5H,10H-imidazo-[1,2-a]indeno [1,2-e]pyrazin-4-one,
10-(3-carboxybenzyl)-5H,10H-imidazo[1,2-a]indeno-[1,2-e]pyrazin-4-one,
10-(4-acetylaminobenzyl)-5H,10H-imidazo[1,2-a]-indeno [1,2-e]pyrazin-4-one,
10-(4-aminobenzyl)-5H,10H-imidazo[1,2-a]indeno-[1,2-e]pyrazin-4-one,
10-[(1-methylimidazol-2-yl)methyl]-5H,10H-imidazo-[1,2-a]indeno[1,2-e]pyrazin-4-one,
10-(tert-butoxycarbonylmethyl)-5H,10H-imidazo-[1,2-a]indeno[1,2-e]pyrazin-4-one,
10-(carboxymethyl)-5H,10H-imidazo[1,2-a]indeno-[1,2-e]pyrazin-4-one,
10-(carboxymethylene)-5H,10H-imidazo[1,2-a]indeno-[1,2-e]pyrazin-4-one,
10-nicotinoylamino-5H,10H-imidazo[1,2-a]indeno-[1,2-e]pyrazin-4-one,
10-formamido-5H,10H-imidazo[1,2-a]indeno[1,2-e]-pyrazin-4-one,
(10R)-10[(R)-α-methoxy-α-trifluoromethylphenyl-acetamido]-5H,10H-imidazo[1,2-a]indeno[1,2-e]pyrazin-4-one,
(10S)-10[(R)-α-methoxy-α-trifluoromethylphenyl-acetamido]-5H,10H-imidazo[1,2-a]indeno[1,2-e]pyrazin-4-one,
10-(4-phenylbutyramido)-5H,10H-imidazo[1,2-a]indeno-[1,2-e]pyrazin-4-one,
10-phenylacetamido-5H,10H-imidazo[1,2-a]indeno-[1,2-e]pyrazin-4-one,
tert-butyl N-[10-(4,5-dihydro-4-oxo-10H-imidazo-[1,2-a]indeno[1,2-e]pyrazinyl)]carbamate,
10-(1-pyrrolyl)-5H,10H-imidazo[1,2-a]indeno[1,2-e]-pyrazin-4-one,
10-amino-10-methyl-5H,10H-imidazo-[1,2-a]indeno[1,2-e]pyrazin-4-one,
10-(4-imidazolylmethyl)-5H,10H-imidazo[1,2-a]indeno-[1,2-e]pyrazin-4-one,
10-[4-(imidazole-1-yl)butyl]-10-methyl-5H,10H-imidazo [1,2-a]indeno[1,2-e]pyrazin-4-one,
10-amino-10-benzyl-7-chloro-5H,10H-imidazo[1,2-a]-indeno[1,2-e]pyrazin-4-one,
10-(3-acetylaminobenzyl)-5H,10H-imidazo[1,2-a]indeno-[1,2-e]pyrazin-4-one,
10-amino-10-phenethyl-5H,10H-imidazo[1,2-a]indeno-[1,2-e]pyrazin-4-one,
10-amino-10-(3-phenylpropyl)-5H,10H-imidazo[1,2-a]-indeno[1,2-e]pyrazin-4-one,
10-amino-10-(4-phenylbutyl)-5H,10H-imidazo[1,2-a]-indeno[1,2-e]pyrazin-4-one,
5-(10-methyl-4,5-dihydro-4-oxo-10H-imidazo[1,2-a]-indeno[1,2-e]pyrazin-10-yl)valeric acid,
10-(3-dimethylaminopropyl)-10-methyl-5H,10H-imidazo-[1,2-a]indeno[1,2-e]pyrazin-4-one,
4-(10-methyl-4,5-dihydro-4-oxo-10H-imidazo[1,2-a]-indeno[1,2-e]pyrazin-10-yl)butyronitrile,
10-hydroxymethyl-10-methyl-5H,10H-imidazo[1,2-a]-indeno[1,2-e]pyrazin-4-one,
4-(10-methyl-4,5-dihydro-4-oxo-10H-imidazo[1,2-a]-indeno[1,2-e]pyrazin-10-yl)butyramide,
3-(10-methyl-4,5-dihydro-4-oxo-10H-imidazo[1,2-a]-indeno[1,2-e]pyrazin-10-yl)propionitrile,
3-(10-methyl-4,5-dihydro-4-oxo-10H-imidazo[1,2-a]-indeno[1,2-e]pyrazin-10-yl)propionic acid,
10-(4-hydroxybutyl)-10-methyl-5H,10H-imidazo[1,2-a]-indeno[1,2-e]pyrazin-4-one,
10-methyl-10-[(1-methylimidazol-2-yl)methyl]-5H,10H-imidazo[1,2-a]indeno[1,2-e]pyrazin-4-one,
10-[(1-methylimidazol-5-yl)methyl]-5H,10H-imidazo-[1,2-a]indeno[1,2-e]pyrazin-4-one,
8-[3-(3-fluorophenyl)ureido]-10-(carboxymethyl)-5H,10H-imidazo[1,2-a]indeno[1,2-e]pyrazin-4-one,
[8-(3-methylureido)-4,5-dihydro-4-oxo-10H-imidazo-[1,2-a]indeno[1,2-e]pyrazin-10-yl]acetic acid,
(4,5-dihydro-4-oxo-10H-imidazo[1,2-a]indeno-[1,2-e]pyrazin-10-yl)glycolic acid,
10-methyl-10-(1-pyrrolyl)-5H,10H-imidazo[1,2-a]-indeno[1,2-e]pyrazin-4-one,
1-[10-(4-oxo-4,5-dihydro-10H-imidazo[1,2-a]indeno-[1,2-e]pyrazinyl)]pyrrole-2-carboxylic acid,
3-[10-(4-oxo-4,5-dihydro-10H-imidazo[1,2-a]indeno-[1,2-e]pyrazinyl)aminocarbonyl]propionic acid,
10-amino-10-benzyl-5H,10H-imidazo[1,2-a]indeno-[1,2-e]pyrazin-4-one,
10-amino-10-propyl-5H,10H-imidazo[1,2-a]indeno-[1,2-e]pyrazin-4-one,
tert-butyl N-[10-(10-methyl-4-oxo-4,5-dihydro-10H-imidazo[1,2-a]indeno[1,2-e]pyrazinyl)]carbamate,
4-[10-(10-methyl-4-oxo-4,5-dihydro-10H-imidazo[1,2-a]-indeno[1,2-e]-pyrazinyl)aminocarbonyl]butyric acid,
10-amino-10-isopropyl-5H,10H-imidazo[1,2-a]indeno-[1,2-e]pyrazin-4-one,
10-amino-10-butyl-5H,10H-imidazo[1,2-a]indeno-[1,2-e]pyrazin-4-one,
10-methyl-10-methylamino-5H,10H-imidazo[1,2-a]indeno-[1,2-e]pyrazin-4-one,
10-carboxymethylene-7-chloro-5H,10H-imidazo[1,2-a]indeno-[1,2-e]pyrazin-4-one, and their salts.

The examples which follow illustrate the invention.

EXAMPLE 1

To a solution of 0.22 g of ethyl 4-ethoxycarbonyloxy-10H-imidazo[1,2-a]indeno[1,2-e]-pyrazine-10,10-dicarboxylate in 20 ml of tetrahydrofuran are added 5.5 ml of 1N hydrochloric acid at a temperature in the region of 20° C. After reacting overnight at the same temperature, the tetrahydrofuran is evaporated off under reduced pressure (15 mmHg; 2 kPa) and the aqueous solution thus obtained is diluted with 5 ml of distilled water. The addition of 10 ml of ethyl acetate causes formation of a cream-coloured precipitate which is filtered off, washed and dried to give 0.15 g of ethyl 5H,10H-imidazo[1,2-a]indeno[1,2-e]pyrazin-4-one-10-carboxylate hydrochloride in the form of a cream-coloured solid (NMR spectrum: [200 MHz; $(CD_3)_2SO-d_6$; δ in ppm]: 1.23 (t, J=7.5 Hz, 3H: —$CH_3$ ethyl); from 4.00 to 4.40 (mt, 2H: —$OCH_2$-ethyl); 5.41 (s, 1H: —C$\underline{H}$— 10); 7.43 and 7.51 (2 broad t, J=8 Hz, 1H each: —$\underline{H}$ 7 and —$\underline{H}$ 8); 7.75 and 7.97 (2 broad d, J=8 Hz, 1H each: —$\underline{H}$ 6 and —$\underline{H}$ 9); 7.82 and 8.14 (2s, 1H each: —$\underline{H}$ of the imidazole); 12.95 (mult., 1H: —CON$\underline{H}$—)).

Ethyl 4-ethoxycarbonyloxy-10H-imidazo[1,2-a]-indeno[1,2-e]pyrazine-10,10-dicarboxylate may be obtained in the following way: to a suspension of 3.35 g of 5H,10H-imidazo[1,2-a)indeno[1,2-e]pyrazin-4-one in 200 ml of anhydrous dioxane are added 1.3 g of 80% sodium hydride. The reaction medium is maintained at reflux for 3 hours and is then brought to a temperature in the region of 20° C. and treated with 8.6 ml of ethyl chloroformate. After reacting overnight at the same temperature, 25 ml of distilled water are added slowly and the dioxane is evaporated off under reduced pressure (15 mmHg; 2 kPa). The organic phase is extracted with ethyl acetate, washed with water, dried and concentrated to dryness under reduced pressure. The residue obtained is purified by flash chromatography on a column of silica using a mixture of dichloromethane and methanol (99/1 by volume) as eluent. 1.2 g of expected product are thus obtained in the form of a purple solid melting at 182° C.

5H,10H-Imidazo[1,2-a)indeno[1,2-e]pyrazin-4-one may be prepared in the following way: a solution of 4.8 g of 3-methyl-4-oxo-5H,10H-imidazo[1,2-a]indeno-[1,2-e] pyrazinium bromide in 30 g of imidazole is heated at 160° C. for 24 hours, cooled to 100° C. and then poured onto a stirred mixture of 75 g of ice and 75 g of distilled water. The insoluble product is filtered off, washed twice with 20 ml in total of distilled water and then dried under reduced pressure (10 mmHg; 1.3 kPa) at 50° C. The product thus obtained (4 g) is dissolved in 80 ml of dimethylformamide and, after addition of 20 g of silica, the solution is concentrated to dryness under reduced pressure (15 mmHg; 2 kPa) at 100° C. The mixture is introduced onto a column 4.2 cm in diameter containing 240 g of silica, and is then eluted with a dichloromethane/methanol mixture (97/3 by volume), collecting 60 ml fractions. Fractions 10 to 70 are combined, 1.5 g of decolorizing charcoal are added and the mixture is filtered and concentrated to dryness under reduced pressure (15 mmHg; 2 kPa) at 55° C. The product obtained (1.7 g) is dissolved in 350 ml of boiling methanol and, after addition of 0.1 g of decolorizing charcoal, the solution is filtered while hot, concentrated under reduced pressure (15 mmHg; 2 kPa) at 40° C. in order to bring its volume to about 30 ml, and is then stored at 5° C. for 60 hours. The crystals are isolated by filtration, washed twice with 20 ml in total of chilled methanol and dried under reduced pressure (1 mmHg; 0.13 kPa) at 60° C. 1.1 g of 5H,10H-imidazo[1,2-a]indeno[1,2-e]pyrazin-4-one, are thus obtained, decomposing without melting at 350° C. [Rf=0.77, thin layer chromatography on silica gel, solvent: dichloromethane/ methanol (8/2 by volume)].

3-Methyl-4-oxo-5H,10H-imidazo[1,2-a]indeno-[1,2-e] pyrazinium bromide may be prepared in the following way: a solution of 5 g of 1-methyl-1H-imidazole-2-carboxamide and 12 g of 85% 2-bromoindanone in 100 ml of anhydrous dimethylformamide is stirred at 115° C. for 28 hours and is then cooled to a temperature in the region of 20° C. The insoluble product is isolated by filtration, washed twice with 20 ml in total of chilled dimethylformamide and dried under reduced pressure (10 mmHg; 1.3 kPa). 4.8 g of 3-methyl-4-oxo-5H,10H-imidazo[1,2-a]indeno[1,2-e]pyrazinium bromide are thus obtained. [NMR spectrum: (200 MHz; DMSO-d$_6$; δ in ppm): 4.13 (s, 2H: —C$\underline{H}_2$ at 10); 4.34 (s, 3H: N$^+$—C$\underline{H}_3$); 7.47 (mt, 2H: —$\underline{H}$ 7 and —$\underline{H}$ 8); 7.68 and 7.96 (2d, J=7.5 Hz, 1H each: —$\underline{H}$ 6 and —$\underline{H}$ 9); 8.32 and 8.45 (2d, J=1 Hz, 1H each: $\underline{H}$ of the imidazole); 13.60 (mult., 1H: N$\underline{H}$)].

1-Methyl-1H-imidazole-2-carboxamide may be prepared according to the process described by D. D. Davey, J. Org. Chem., 52, 4379 (1987).

EXAMPLE 2

To a suspension of 0.5 g of 10-amino-5H,10H-imidazo [1,2-a]indeno[1,2-e]pyrazin-4-one in 15 ml of dimethylformamide is added 0.6 ml of ethyl trifluoroacetate at a temperature in the region of 20° C. The reaction medium is heated at 60° C. for 5 hours and is then cooled and concentrated to dryness under reduced pressure (15 mmHg; 2 kPa). The residue is taken up in dichloromethane and the insoluble product is filtered off, washed and dried. After purification by flash chromatography using a mixture of ethyl acetate and methanol (90/10 by volume) as eluent, 0.06 g of 10-imino-5H,10H-imidazo[1,2-a]indeno[1,2-e]pyrazin-4-one is obtained in the form of a reddish powder, the melting point of which is greater than 260° C. (NMR spectrum: [200 MHz; (CD$_3$)$_2$SO-d$_6$; δ in ppm]: from 7.20 to 7.50 (mt, 2H: —$\underline{H}$ 7 and —$\underline{H}$ 8); 7.57 and 8.33 (2s, 1H each: —$\underline{H}$ of the imidazole); 7.65 and 7.86 (2 broad d, J=8 Hz, 1H each: —$\underline{H}$ 6 and —$\underline{H}$ 9); from 11.10 to 12.10 (broad mult., 1H: —CON$\underline{H}$—)).

10-Amino-5H,10H-imidazo[1,2-a]indeno-[1,2-e]pyrazin-4-one may be prepared in the following way: a solution of 12.9 g of 10-acetamido-5H,10H-imidazo-[1,2-a]indeno[1,2-e]pyrazin-4-one in 650 ml of aqueous 2N hydrochloric acid solution is heated to boiling for 2 hours, cooled and then concentrated to dryness under reduced pressure (15 mmHg; 2 kPa) at 80° C. 4 g (out of the 14.8 g obtained in total) are dissolved in 250 ml of distilled water and the solution is stirred for 16 hours at a temperature in the region of 20° C. The crystals formed are isolated by filtration, washed successively with 25 ml of distilled water and 25 ml of methanol and then air-dried at a temperature in the region of 20° C. The product obtained (3.5 g) is stirred in suspension for 10 minutes in 100 ml of boiling methanol and, after cooling and storing for 1 hour at 5° C., is isolated by filtration, washed with 20 ml of chilled methanol and then dried under reduced pressure (1 mmHg; 0.13 kPa) at 100° C. 2.1 g of 10-amino-5H,10H-imidazo[1,2-a]indeno-[1,2-e] pyrazin-4-one hydrochloride are thus obtained, decomposing without melting at about 240° C. (NMR spectrum: (200 MHz; DMSO-d$_6$; δ in ppm): 5.70 (broad s, 1H: C$\underline{H}$—N+—Cl—); 7.48 and 7.58 (2t, J=7.5 Hz, 1H each: —$\underline{H}$7 and —$\underline{H}$8); 7.72 and 8.76 (2s, 1H each: —$\underline{H}$ of the imidazole); 7.98 and 8.09 (2d, J=7.5 Hz, 1H each: —$\underline{H}$ 6 and —$\underline{H}$ 9); 9.47 (mult., 3H: N$^+\underline{H}$3Cl—); 12.80 (mult., 1H: —N$\underline{H}$—)).

10-Acetamido-5H,10H-imidazo[1,2-a]indeno-[1,2-e] pyrazin-4-one may be prepared in the following way: a suspension of 5.25 g of 10-(E-hydroxyimino)-5H,10H-imidazo[1,2-a]indeno[1,2-e]pyrazin-4-one and 2.9 g of zinc powder in 100 ml of acetic acid is heated for 2 hours at a temperature between 80° C. and 90° C. After addition of 100 ml of acetic acid, the mixture is filtered and the filtrate is concentrated to dryness under reduced pressure (10 mmHg; 2 kPa) at 65° C. The product obtained (3.8 g) is suspended in 100 ml of distilled water, filtered, washed with 10 ml of distilled water and with 10 ml of acetone and then dried under reduced pressure (15 mmHg; 2 kPa) at 20° C. The product obtained (2 g) is dissolved in 60 ml of boiling dimethylformamide and, after addition of 0.1 g of decolorizing charcoal, the solution is filtered while hot. The filter is washed with 10 ml of boiling dimethylformamide, and the combined filtrate and washing are stored for 4 hours at a temperature in the region of 20° C. The crystals formed are isolated by filtration, washed successively with 10 ml of dimethylformamide, 10 ml of distilled water and 10 ml of acetone, and dried to dryness under reduced pressure (1 mmHg; 0.13 kPa) at 100° C. 0.43 g of 10-acetamido-5H, 10H-imidazo[1,2-a]indeno[1,2-e]pyrazin-4-one is thus obtained, decomposing without melting at 330° C. (NMR spectrum: (200 MHz; DMSO-d$_6$; δ in ppm): 2.00 (s, 3H: —CO—C$\underline{H}_3$); 6.13 (d, J=8.5 Hz, 1H: C$\underline{H}$—N); 7.35 and 7.48 (2t, J=7.5 Hz, 1H each: —$\underline{H}$7 and —$\underline{H}$8); 7.48 and 7.85 (2d, J=7.5 Hz, 1H each: —$\underline{H}$ 6 and —$\underline{H}$ 9); 7.58 and 7.65 (2 broad s, 1H each: —$\underline{H}$ of the imidazole); 8.58 (d, J=8.5 Hz, 1H: —N$\underline{H}$—COCH$_3$); 12.50 (mult., 1H: —N$\underline{H}$—)).

10-(E—Hydroxyimino)-5H,10H-imidazo[1,2-a]-indeno [1,2-e]pyrazin-4-one may be prepared in the following way:

0.4 g of 80% sodium hydride is added to a suspension of 1.1 g of 5H,10H-imidazo[1,2-a]indeno-[1,2-e]pyrazin-4-one in 10 ml of anhydrous dimethyl sulphoxide. After stirring for 10 minutes at a temperature in the region of 20° C., a solution of 0.7 g of isoamyl nitrite in 2 ml of anhydrous dimethyl sulphoxide is added dropwise over 5 minutes, then the mixture is stirred for 1 hour at the same temperature. 10 ml of distilled water are added slowly and the mixture is then poured onto 120 g of water and ice, acidified with 1 ml of acetic acid and then centrifuged. After removal of the supernatant solution, the solid is suspended in 25 ml of distilled water, filtered off, washed with 10 ml of acetone and dried under reduced pressure (15 mmHg; 2 kPa) at 20° C. The product obtained (1.5 g) is dissolved in 100 ml of boiling dimethylformamide and, after addition of 0.1 g of decolorizing charcoal, the solution is filtered while hot, cooled, poured into 800 ml of distilled water and centrifuged. The solid is suspended in 20 ml of distilled water, filtered off,,washed with 20 ml of acetone and dried under reduced pressure (15 mmHg; 2 kPa) at 20° C. The product obtained (0.9 g) is dissolved in 75 ml of dimethyl sulphoxide at 20° C. and, after addition of 0.1 g of decolorizing charcoal, the solution is filtered. The filter is washed twice with 20 ml in total of dimethyl sulphoxide, then the filtrate and washing are combined, 75 ml of distilled water are added and the mixture is centrifuged. The solid is suspended in 25 ml of distilled water, filtered off, washed twice with 50 ml in total of acetone and then dried under reduced pressure (1 mmHg; 0.13 kPa) at 60° C. 0.63 g of 10-(E-hydroxyimino)-5H,10H-imidazo[1,2-a]indeno[1,2-e]pyrazin-4-one is thus obtained, decomposing without melting above 300° C. (NMR spectrum: (200 MHz; DMSO-$d_6$; δ in ppm): 7.40 and 7.48 (2t, J=7 Hz, 2H: —$\underline{H}$7 and —$\underline{H}$8); 7.60 and 8.00 (2 broad s, 1H each: —$\underline{H}$ of the imidazole); 7.82 and 8.20 (2d, J=7 Hz, 1H each: —$\underline{H}$6 and —$\underline{H}$9); 12.70 and 13.00 (2 mult., 1H each: —N$\underline{H}$—and —O$\underline{H}$)).

EXAMPLE 3

A suspension of 8 g of 10-(2-carboxybenzylidene)-5H,10H-imidazo[1,2-a]indeno-[1,2-e]pyrazin-4-one in 350 ml of dimethylformamide and 50 ml of methanol is hydrogenated in the presence of 1 g of 10% palladium-on-charcoal for 20 hours at 10 bar and at a temperature in the region of 20° C. The reaction mixture is filtered on clarcel and the filtrate is evaporated under reduced pressure. The beige-coloured residue obtained is triturated with 200 ml of boiling methanol, filtered and dried at 100° C. under vacuum (1 mmHg; 0.13 kPa); 2.2 g of 10-(2-carboxy-benzyl)-5H,10H-imidazo[1,2-a]indeno-[1,2-e]pyrazin-4-one are obtained in the form of an off-white solid melting above 260° C. (Analysis, % calculated C: 70.58, H: 4.23, N: 11.76, O: 13.43, % found C: 70.6, H: 4.3, N: 12.1).

10-(2—Carboxybenzylidene)-5H,10H-imidazo-[1,2-a]indeno[1,2-e]pyrazin-4-one may be prepared in the following way: under cover of nitrogen, 2.56 g of 80% sodium hydride are added portionwise and with stirring to a solution, cooled to 19° C., of 8 g of 5H,10H-imidazo[1,2-a]indeno[1,2-e]pyrazin-4-one in 120 ml of dimethyl sulphoxide. The stirring is continued for 35 minutes and a solution of 6.47 g of 2-methoxycarbonylbenzaldehyde in 20 ml of dimethyl sulphoxide is added dropwise. The stirring is continued for 5 hours. The reaction mixture is then poured onto a mixture of water and ice (300 ml) and neutralized with 7 ml of acetic acid. The suspension obtained is filtered and the solid thus isolated is triturated with 150 ml of acetone, filtered and air-dried to give 13 g of 10-(2-carboxybenzylidene)-5H,10H-imidazo[1,2-a]-indeno[1,2-e]pyrazin-4-one melting above 260° C., in the form of a green solid which is used without further purification in the subsequent syntheses (mass spectrum m/z 355 (M$^+$), 310 (M$^+$—COOH), 222 ($C_{15}H_{10}O_2$), 194 (222-CO), 133 ($C_6H_3N_3O$), 105 (PhCO)).

EXAMPLE 4

12.2 g of a mixture of 10-(4-methoxycarbonylbenzylidene)-5H,10H-imidazo[1,2-a]indeno[1,2-e]pyrazin-4-one and 10-(4-carboxybenzylidene)-5H,10H-imidazo-(1,2-a]indeno(1,2-e]pyrazin-4-one suspended in 350 ml of dimethylformamide and 50 ml of methanol are hydrogenated in the presence of 1.5 g of 10% palladium-on-charcoal for 20 hours at 10 bar and at a temperature in the region of 20° C. The reaction mixture is filtered on paper and 300 ml of dimethyl sulphoxide are added in order to dissolve the white solid remaining on the filter. The filtrate is evaporated under reduced pressure and the light-yellow solid obtained is triturated with 200 ml of dimethylformamide, filtered and dried to give 14 g of a mixture of 10-(4-carboxy-benzyl)-5H,10H-imidazo[1,2-a]indeno[1,2-e]pyrazin-4-one and 10-(4-methoxycarbonylbenzyl)-5H,10H-imidazo-[1,2-a]indeno[1,2-e]pyrazin-4-one. This mixture is triturated with 200 ml of dimethylformamide and filtration gives two fractions:

1) the insoluble fraction is triturated with 50 ml of 0.1N sodium hydroxide, filtered and the solid obtained is chromatographed on a column of silica (80 g), eluting with a mixture of dichloromethane and methanol (2/1 by volume); after trituration with 50 ml of ethyl ether, filtration and drying at 80° C. under vacuum (2 mmHg; 0.26 kPa), 0.7 g of 10-(4-methoxycarbonylbenzyl)-5H,10H-imidazo[1,2-a]indeno-[1,2-e]pyrazin-4-one is obtained in the form of a light-yellow solid melting above 260° C. (Analysis, % calculated C: 71.15, H: 4.61, N: 11.31, O: 12.92, % found C: 70.7, H: 4.2, N: 11.4).

2) the soluble fraction is acidified with 4 ml of acetic acid and the precipitate formed is filtered off, triturated twice with dimethylformamide (200 ml and 75 ml), filtered and dissolved in 140 ml of hot dimethylformamide; on addition of 100 ml of methanol an insoluble part precipitates, this part being separated off by filtration, and the soluble part is concentrated under reduced pressure. The solid obtained is triturated with 150 ml of acetone, filtered and dried at 80° C. under vacuum (2 mmHg; 0.26 kPa). 0.65 g of 10-(4-carboxybenzyl)-5H,10H-imidazo[1,2-a]indeno-[1,2-e]pyrazin-4-one is obtained in the form of a beige-coloured solid melting above 260° C. (Analysis, % calculated C: 70.58, H: 4.23, N: 11.76, O: 13.43, % found C: 70.3, H: 4.5, N: 12.2, O: 13.4).

The starting mixture of acid and ester was prepared as follows: the process is performed as in Example 3 but starting with 6.47 g of 4-methoxycarbonyl-benzaldehyde and by modifying the reaction treatment: 7 ml of acetic acid, and then 140 ml of water and 200 ml of methanol are added dropwise to the reaction mixture, between 21° and 26° C. The suspension obtained is filtered and dried to give 12.2 g of a mixture of 10-(4-carboxybenzylidene)-5H,10H-imidazo[1,2-a]indeno-[1,2-e]pyrazin-4-one and 10-(4-methoxycarbonyl-benzylidene)-5H,10H-imidazo[1,2-a]indeno[1,2-e]pyrazin-4-one in the form of an orange-coloured solid melting above 260° C., which mixture is used without further purification in the subsequent syntheses (mass spectrum m/z 356 (MH$^+$) and 370 (MH$^+$)).

EXAMPLE 5

The process is performed as in Example 3 for the preparation of 10-(2-carboxybenzylidene)-5H,10H-imidazo[1,2- a]indeno[1,2-e]pyrazin-4-one but starting with 5 g of 5H,10H-imidazo[1,2-a]indeno[1,2-e]pyrazin-4-one, 100 ml of dimethyl sulphoxide, 4.04 g of 3-methoxycarbonylbenzaldehyde and 1.6 g of 80% sodium hydride. After treatment of the reaction mixture with 100 ml of water and 10 ml of acetic acid, the suspension obtained is filtered; the insoluble product is washed with water, air-dried and then triturated with 80 ml of dimethylformamide, filtered off and dried. The yellow solid obtained (1 g) is suspended in 100 ml of water and, after addition of 25 ml of 0.1N sodium hydroxide, the solution is filtered and acidified with 2.5 ml of 1N hydrochloric acid. The precipitate formed is washed with water, triturated with 50 ml of methanol and dried at 60° C. under vacuum (1 mmHg; 0.13 kPa). 0.8 g of 10-(3-carboxybenzylidene)-5H,10H-imidazo[1,2-a]indeno[1,2-e]pyrazin-4-one is obtained in the form of a yellow solid melting above 260° C., which product is converted into the disodium salt of formula $C_{21}H_{11}N_3O_3Na_2$ (Analysis, % calculated C 63.17, H: 2.78, N: 10.52, O: 12.02, Na : 11.51, % found C: 62.9, H: 2.6, N: 10.2).

EXAMPLE 6

The process is performed as in Example 3 but starting with 6.9 g of 10-(3-carboxybenzylidene)-5H,10H-imidazo[1,2-a]indeno[1,2-e]pyrazin-4-one, 50 ml of methanol, 250 ml of dimethylformamide and 0.7 g of 10% palladium-on-charcoal. After evaporation of the solvents and trituration of the solid obtained with 100 ml of methanol, 5.1 g of 10-(3-carboxybenzyl)-5H,10H-imidazo[1,2-a]indeno[1,2-e]pyrazin-4-one are obtained in the form of an off-white solid melting above 260° C., which product is converted into the sodium salt of formula $C_{21}H_{14}N_3O_3Na$ (Analysis, % calculated C 66.49, H: 3.72, N: 11.08, O: 12.65, Na : 6.06, % found C: 66.6, H: 3.7, N: 10.9).

EXAMPLE 7

The process is performed as in Example 3 but starting with 4.7 g of 10-(4-acetylaminobenzylidene)-5H,10H-imidazo[1,2-a]indeno[1,2-e]pyrazin-4-one, 250 ml of dimethylformamide, 50 ml of methanol and 0.6 g of 10% palladium-on-charcoal for 26 hours. 1.2 g of 10-(4-acetylaminobenzyl)-5H,10H-imidazo[1,2-a]indeno-[1,2-e]pyrazin-4-one are obtained in the form of a cream-white solid melting above 260° C. (Analysis, % calculated C: 71.34, H: 4.90, N: 15.13, O: 8.64, % found C: 71.3, H: 4.7, N: 15.3, O: 8.3).

10-(4-Acetylaminobenzylidene)-5H,10H-imidazo-[1,2-a]indeno[1,2-e]pyrazin-4-one may be prepared in the following way: the process is performed as in Example 3 for the preparation of 10-(2-carboxy-benzylidene)-5H,10H-imidazo[1,2-a]indeno[1,2-e]pyrazin-4-one but starting with 4 g of 5H,10H-imidazo[1,2-a]-indeno[1,2-e]pyrazin-4-one, 70 ml of dimethyl sulphoxide, 3.2 g of 4-acetylaminobenzaldehyde and 1.6 g of 60% sodium hydride. After treatment of the reaction mixture with 70 ml of water, 3 ml of acetic acid and 100 ml of methanol, the suspension is filtered; the insoluble product is triturated with 100 ml of dimethylformamide, filtered off and air-dried to give 4.7 g of 10-(4-acetylaminobenzylidene)-5H,10H-imidazo[1,2-a]indeno[1,2-e]pyrazin-4-one in the form of a yellow solid melting above 260° C., which product is used without further purification in the subsequent syntheses (mass spectrum m/z 369 (MH$^+$)).

EXAMPLE 8

A mixture of 0.1 g of 10-(4-acetylamino-benzyl)-5H,10H-imidazo[1,2-a]indeno[1,2-e]pyrazin-4-one, 5 ml of 1N sodium hydroxide and 5 ml of water is heated at 98° C. for 16 hours. After cooling to a temperature in the region of 20° C., the reaction mixture is acidified with 1 ml of acetic acid, filtered and the precipitate formed is washed with 1 ml of methanol and air-dried. 90 mg of 10-(4-aminobenzyl)-5H,10H-imidazo-[1,2-a]indeno[1,2-e]pyrazin-4-one are obtained in the form of a yellow solid melting above 260° C. (NMR spectrum: [200 MHz; $(CD_3)_2SO-d_6$; δ in ppm]: 3.19 and 3.42 (2dd, J=15 and 7 Hz and J=15 and 5 Hz respectively, 1H each: Ar—C$\underline{H}_2$); 4.41 (dd, J=7 and 5 Hz, 1H: —$\underline{H}_{10}$); 4.80 (broad mult., 1H: —N$\underline{H}_2$); 6.22 and 6.40 (2d, J=7.5 Hz, 2H each: aromatic —$\underline{H}$); 7.32 (m, 2H: —$\underline{H}_7$ and —$\underline{H}_8$); 7.45 and 7.75 (2 broad d, J=7.5 Hz, 1H each: —$\underline{H}_6$ and —$\underline{H}_9$); 7.64 and 8.13 (2 broad s, 1H each: —$\underline{H}$ of the imidazole); 12.23 (broad s, 1H: —CO—N$\underline{H}$—)).

EXAMPLE 9

The process is performed as in Example 3 for the preparation of 10-(2-carboxybenzylidene)-5H,10H-imidazo[1,2-a]indeno[1,2-e]pyrazin-4-one but starting with 4.46 g of 5H,10H-imidazo[1,2-a]indeno[1,2-e]-pyrazin-4-one, 80 ml of dimethyl sulphoxide, 2.6 g of 1-methyl-2-formylimidazole and 1.44 g of 80% sodium hydride. After treatment of the reaction mixture with 80 ml of water and 3 ml of acetic acid, the suspension is filtered and the red solid obtained is washed with methanol and air-dried to give 5 g of 10-[(1-methylimidazol-2-yl)methylene]-5H,10H-imidazo-[1,2-a]indeno[1,2-e]pyrazin-4-one. The dihydrochloride is formed by adding 3 ml of 3N hydrochloric acid solution in-ethyl ether to a suspension of 1.5 g of crude base in 50 ml of methanol. The yellow precipitate formed is filtered off and dried at 60° C. under vacuum (1 mmHg; 0.13 kPa). 1.75 g of 10-[(1-methylimidazol-2-yl)methylene]-5H,10H-imidazo[1,2-a]indeno[1,2-e]-pyrazin-4-one dihydrochloride are obtained, melting above 260° C. (Analysis, % calculated C: 55.68, H: 3.89, ° Cl: 18.26, N: 18.04, O: 4.12, % found C: 55.8, H: 3.9, N: 17.9).

1-Methyl-2-formylimidazole may be prepared according to the process described by P. Fournari et al., Bull. Soc. Chim. Fr., (6), 2438 (1968).

EXAMPLE 10

The process is performed as in Example 3 but starting with 3.5 g of 10-[(1-methylimidazol-2-yl)-methylene-5H,10H-imidazo[1,2-a]indeno[1,2-e]pyrazin-4-one, 200 ml of dimethylformamide, 50 ml of methanol and 0.35 g of 10% palladium-on-charcoal. After evaporation of the solvents, the crude product is dissolved in 30 ml of methanol, and 100 ml of ethyl ether and 8 ml of 3.2N hydrochloric acid in ethyl ether are added. The precipitate formed is filtered off, triturated with 30 ml of ethanol and filtered off. The solid obtained is dissolved under hot conditions in a mixture of 75 ml of ethanol and 75 ml of methanol and, after addition of 0.5 g of activated charcoal, the solution is filtered and concentrated to one-third the volume; the solid obtained is filtered off and dried at 20° C. under vacuum (1 mmHg; 0.13 kPa). 2.3 g of 10-[(1-methylimidazol-2-yl)methyl]-5H,10H-imidazo[1,2-a]indeno[1,2-e]pyrazin-4-one dihydrochloride are obtained in the form of a brown solid melting above 260° C. (Analysis, % calculated C 55.40, H: 4.39, ° Cl : 18.17, N: 17.94, O: 4.10, % found C: 55.1, H: 4.0, N: 17.7).

EXAMPLE 11

The process is performed as in Example 3 for the preparation of 10-(2-carboxybenzylidene)-5H,10H-imidazo[1,2-a]indeno[1,2-e]pyrazin-4-one but starting with 3 g of 5H,10H-imidazo[1,2-a]indeno[1,2-e]pyrazin-4-one, 60 ml of dimethyl sulphoxide, 2.6 g of tert-butyl glyoxylate and 0.96 g of 80% sodium hydride. After treatment of the reaction mixture with acetic acid (3 ml) and then water (60 ml), the suspension obtained is filtered. The insoluble product is washed with water (3×50 ml), with acetone (3×30 ml), air-dried and dissolved at 80° C. in 50 ml of dimethylformamide. The solution is filtered and, after addition of 50 ml of methanol, is left overnight at a temperature in the region of 5° C. The crystals formed are filtered off and the solid obtained (1.4 g) is dissolved in dimethylformamide and bound to 4 g of silica by evaporation of the solvent on a rotary evaporator. The evaporation residue is washed with a mixture of dichloromethane and methanol (95/5 by volume) and then with 300 ml of dimethylformamide. The dimethylformamide extract is evaporated under reduced pressure and the grey solid obtained is triturated with a mixture of water (5 ml) and methanol (20 ml), filtered, washed with acetone and air-dried. 0.8 g of 10-(1-tert-butoxy-carbonyl-1-hydroxymethyl)-5H,10H-imidazo[1,2-a]-indeno[1,2-e] pyrazin-4-one is obtained in the form of a light-grey solid melting above 260° C. (NMR spectrum: (200 MHz; DMSO-$d_6$; δ in ppm): 0.80 [s, 9H: —O—C(C$\underline{H}_3$)$_3$]; 5.55 (d, J=6.5 Hz, 1H: —CO—C$\underline{H}$—O—); 5.58 (s, 1H: —C$\underline{H}$— 10); 6.34 (d, J=6.5 Hz, 1H: —O$\underline{H}$); 7.16 and 7.93 (2 broad d, J=8 Hz, 1H each: —$\underline{H}$ 6 and —$\underline{H}$ 9); 7.32 and 7.48 (2 broad t, J=8 Hz, 1H each: —$\underline{H}$ 7 and —$\underline{H}$ 8); 7.72 and 8.67 (2s, 1H each: —$\underline{H}$ of the imidazole); 9.73 (mult., 1H: —O$\underline{H}$); 12.68 (broad s, 1H: —CON$\underline{H}$—)).

tert-Butyl glyoxalate may be prepared according to the process described by L. A. Carpino, J. Org. Chem., 29, 2820 (1964).

EXAMPLE 12

5.85 g of 10-(1-tert-butoxycarbonyl-1-hydroxymethyl)-5H,10H-imidazo[1,2-a]indeno[1,2-e]pyrazin-4-one are heated to 90°–100° C. in 300 ml of dimethylformamide, filtered immediately and 150 ml of methanol and 200 ml of water are added to the filtrate, which is left overnight at a temperature in the region of 5° C. The crystals formed are filtered off, washed with 20 ml of water and dried at 80° C. under vacuum (2 mmHg; 0.26 kPa) to give 3.4 g of 10-(tert-butoxycarbonylmethylene)-5H,10H-imidazo[1,2-a]indeno[1,2-e]pyrazin-4-one in the form of a red solid melting above 260° C. (Analysis, % calculated C: 68.05, H: 5.11, N: 12.53, O: 14.31, % found C: 68.0, H: 5.6, N: 12.5, O: 14.3).

EXAMPLE 13

The process is performed as in Example 3 but starting with 1.78 g of 10-(tert-butoxycarbonyl-methylene)-5H,10H-imidazo[l,2-a]indeno[1,2-e]pyrazin-4-one, 280 ml of dimethylformamide, 20 ml of methanol and 0.18 g of 10% palladium-on-charcoal. After evaporation of the solvents, the beige-coloured solid obtained is purified by chromatography on a column of silica (180 g partially deactivated with 2% water), eluting with a dichloromethane/methanol mixture (95/5 by volume). A white solid is obtained, which is triturated with 10 ml of methyl tert-butyl ether, filtered off and dried at 80° C. under vacuum (2 mmHg; 0.26 kPa) to give 0.35 g of 10-(tert-butoxycarbonylmethyl-5H,10H-imidazo[1,2-a]-indeno[1,2-e]pyrazin-4-one (Analysis, % calculated C 67.64, H: 5.68, N: 12.45, O: 14.23, % found C: 67.2, H: 6.0, N: 12.4, O: 14.5).

EXAMPLE 14

A mixture of 1 g of 10-(tert-butoxycarbonyl-methyl)-5H,10H-imidazo[l,2-a]indeno[1,2-e]pyrazin-4-one, 5 ml of dimethyl sulphoxide and 25 ml of 3N hydrochloric acid in ethyl ether is stirred, under cover of argon, for 107 hours at a temperature in the region of 20° C. After concentration under reduced pressure, the residue is crystallized from 30 ml of acetone. The solid obtained is treated with 50 ml of water and 7 ml of saturated sodium hydrogen carbonate solution; three extractions with dichloromethane (3×50 ml) are performed on this mixture, the aqueous phase is filtered and the aqueous solution is acidified with 8 ml of 1N hydrochloric acid. The precipitate formed is filtered off, washed with water and dried at 80° C. under vacuum (1 mmHg; 0.13 kPa) to give 0.35 g of 10-(carboxymethyl)-5H,10H-imidazo[1,2-a]indeno[1,2-e]-pyrazin-4-one in the form of a greenish solid melting above 260° C. (Analysis, % calculated C: 64.05, H: 3.94, N: 14.94, O: 17.06, % found C: 63.7, H: 3.2, N: 14.9).

EXAMPLE 15

2.4 g of 10-(1-carboxy-1-hydroxymethyl)-5H,10H-imidazo[1,2-a]indeno[1,2-e]pyrazin-4-one, 20 ml of acetic anhydride and 20 mg of zinc chloride are heated to reflux for 4 hours, under cover of argon. The reaction mixture is treated with 25 ml of water and the precipitate formed is filtered off, washed with 25 ml of water and then with 2×25 ml of acetone and dried at 80° C. under vacuum (1 mmHg; 0.13 kPa) to give 0.52 g of 10-(carboxymethylene)-5H,10H-imidazo[1,2-a]indeno-[1,2-e]pyrazin-4-one in the form of an orange-yellow solid, which product is converted into the sodium salt of formula $C_{15}H_8N_3O_3Na$ (Analysis, % calculated C: 59.81, H: 2.68, N: 13.95, O: 15.93, Na : 7.63, % found C 59.5, H: 2.1, N: 13.6).

10-(1-Carboxy-1-hydroxymethyl)-5H,10H-imidazo[1,2-a]indeno[1,2-e]pyrazin-4-one may be prepared in the following way: the process is performed as in Example 3 but starting with 6.7 g of 5H,10H-imidazo[1,2-a]indeno[1,2-e] pyrazin-4-one, 140 ml of dimethylformamide, 4.15 g of glyoxylic acid and 4.95 g of 80% sodium hydride. After treatment of the reaction mixture with 11 ml of acetic acid, the suspension is heated at 80° C. for two hours. The suspension is then filtered and the solid obtained is washed with acetone (3×75 ml), with methanol (75 ml), again with acetone (2×75 ml) and then dissolved in 500 ml of water. The aqueous phase is extracted with ethyl acetate (2×100 ml) and the aqueous solution is filtered and acidified with 45 ml of 1N hydrochloric acid. The precipitate formed is filtered off, washed with 50 ml of water and then with acetone (3×75 ml) and dried at 70° C. under vacuum (1 mmHg; 0.13 kPa). 5.7 g of 10-(1-carboxy-1-hydroxymethyl)-5H,10H-imidazo[1,2-a]indeno-[1,2-e]pyrazin-4-one are obtained in the form of a pale yellow solid melting above 260° C. (NMR spectrum: [200 MHz; $(CD_3)_2SO-d_6$ with a few drops of $CD_3COOD-d_4$; δ in ppm]: 4.60 (d, J=3.5 Hz, 1H: —$\underline{H}_{10}$); 5.09 (d, J=3.5 Hz, 1H: C$\underline{H}$—O—); from 7.30 to 7.45 (m, 2H: —$\underline{H}_7$ and —$\underline{H}_8$); 7.45 and 7.85 (2 broad d, J=7.5 Hz, 1H each: —$\underline{H}_6$ and —$\underline{H}_9$); 7.57 and 8.23 (2 broad s, 1H each: —$\underline{H}$ of the imidazole), in $(CD_3)_2SO-d_6$ 2 additional signals are observed: 5.60 (mult., 1H: —O$\underline{H}$); 12.35 (broad s, 1H: —CO—N$\underline{H}$—)).

EXAMPLE 16

A solution of 19.95 g of 10-(carboxymethyl-ene)-5H,10H-imidazo[1,2-a]indeno[1,2-e]pyrazin-4-one in 720 ml of 1N sodium hydroxide and 200 ml of water is hydrogenated at 1.7 bar and at a temperature in the region of 23° C. for 22 hours in the presence of 2 g of 10% palladium-on-charcoal. The reaction mixture is filtered and the filtrate is acidified with 95 ml of 1N hydrochloric acid. The precipitate formed is filtered off, washed with water (200 ml), then with acetone (5×200 ml) and dried at 80° C. under vacuum (1 mmHg; 0.13 kPa). 17.65 g of 10-(carboxymethyl)-5H,10H-imidazo[1,2-a]indeno[1,2-e]pyrazin-4-one are obtained in the form of a light-grey solid, which product is converted into the sodium salt of formula $C_{15}H_{10}N_3O_3Na$ (Analysis, % calculated C: 59.41, H: 3.32, N: 13.86, O: 15.83, Na: 7.58, % found C: 59.3, H: 2.9, N: 13.7).

EXAMPLE 17

The process is performed as in Example 3 for the preparation of 10-(2-carboxybenzylidene)-5H,10H-imidazo[1,2-a]indeno[1,2-e]pyrazin-4-one but starting with 3.3 g of 5H,10H-imidazo[1,2-a]indeno[1,2-e]-pyrazin-4-one, 66 ml of dimethyl sulphoxide, 2.35 g of ethyl 5-oxopentanoate and 1.06 g of sodium hydride. After treatment of the reaction mixture with water (66 ml) and with acetic acid (6.6 ml), the suspension obtained is filtered, the insoluble product is washed with water (50 ml), with methanol (25 ml) and then with ethyl ether (2×25 ml) and dried at 60° C. under reduced pressure. The solid obtained is suspended in a mixture of 70 ml of ethanol and 6 ml of 10N sodium hydroxide, filtered off, washed with ethanol and purified by dissolution in 15 ml of water and precipitation with 15 ml of 1N hydrochloric acid. The precipitate is filtered off, washed with water (2×10 ml), triturated at the reflux of methanol (200 ml), filtered off and dried. 0.4 g of 5-(4-hydroxyimidazo[1,2-a]indeno-[1,2-e]pyrazin-10-ylidene]pentanoic acid is obtained, which product is converted into the disodium salt of formula $C_{18}H_{13}N_3O_3Na_2$ (Analysis, % calculated C: 59.18, H: 3.59, N: 11.50, O: 13.14, Na: 12.59, % found C 58.8, H: 3.4, N: 11.5).

Ethyl 5-oxopentanoate may be prepared according to the process described by O. P. Vig et al., J. Indian Chem. Soc., 49, 163 (1972).

EXAMPLE 18

The process is performed as in Example 15 for the preparation of 10-(1-carboxy-1-hydroxymethyl)-5H, 10H-imidazo[1,2-a]indeno[1,2-e]pyrazin-4-one but starting with 2 g of 8-(3-methylureido)-5H,10H-imidazo[1,2-a]indeno[1,2-e]pyrazin-4-one, 32 ml of dimethyl sulphoxide, 0.93 g of glyoxylic acid monohydrate and 1.11 g of sodium hydride. After treatment of the reaction mixture with acetic acid (2.4 ml), the suspension is filtered and 100 ml of acetone are added to the filtrate. The greyish precipitate formed is filtered off, triturated with ethanol (2×50 ml), filtered off and dried at 60° C. under vacuum (1 mmHg; 0.13 kPa). The solid obtained (2.29 g) is treated with 24 ml of water and 12 ml of 1N hydrochloric acid. A brown precipitate forms which is filtered off, washed with water (2×5 ml), then with acetone (2×5 ml) and dried at 60° C. under vacuum (1 mmHg; 0.13 kPa). 1 g of 10-(1-carboxy-1-hydroxymethyl)-8-(3-methylureido)-5H,10H-imidazo[1,2-a]indeno[1,2-e]pyrazin-4-one is obtained in the form of a dark yellow solid melting above 260° C. (Analysis, % calculated C: 55.28, H: 4.09, N: 18.96, O: 21.66, % found C: 55.1, H: 3.6, N: 18.9).

8-(3-Methylureido)-5H,10H-imidazo[1,2-a]-indeno[1,2-e]pyrazin-4-one may be prepared in the following way: to 1.5 g of 8-amino-5H,10H-imidazo[1,2-a]indeno[1,2-e]pyrazin-4-one hydrochloride suspended in 50 ml of dimethylformamide are added 2.3 ml of triethylamine followed, after dissolution, by 0.65 ml of methyl isocyanate dissolved in 10 ml of dimethylformamide. The reaction is continued for 15 hours at a temperature in the region of 20° C. A further 0.65 ml of methyl isocyanate dissolved in 10 ml of dimethylformamide is added and the stirring is continued for a further 4 hours at the same temperature. The insoluble product is then filtered off, washed with water and recrystallized from dimethylformamide and then from dimethyl sulphoxide. After washing with water and with acetone, the product is dried under reduced pressure (1 mmHg; 0.13 kPa) at 100° C. 0.3 g of 8-(3-methylureido)-5H,10H-imidazo-[1,2-a]indeno[1,2-e]pyrazin-4-one is thus obtained in the form of a beige-coloured solid, the melting point of which is greater than 260° C. (Analysis, $C_{35}H_{13}N_5O_2.1.26H_2O$ % calculated C: 61.01; H: 4.44; N: 23.72; % found C: 61.4; H: 4.8; N: 24.1).

8-Amino-5H,10H-imidazo[1,2-a]indeno[1,2-e]-pyrazin-4-one may be prepared in the following way: a mixture of 9.7 g of 5H,10H-8-nitroimidazo[1,2-a]indeno-[1,2-e]pyrazin-4-one, 370 ml of 0.1N aqueous sodium hydroxide and 0.3 g of 10% palladium-on-charcoal is hydrogenated at a temperature in the region of 20° C. and at a pressure of 1.2 bar for 23 hours. The suspension is acidified with 80 ml of 1N hydrochloric acid and is then filtered. The solid obtained is taken up in 600 ml of boiling water. Animal black is added and the mixture is filtered while hot on Cellite. The filtrate crystallizes after cooling in a bath of ice. The crystals are isolated by filtration and washed twice with 50 ml of ethyl ether. 4.7 g of 5H,10H-8-amino-imidazo[1,2-a]indeno[1,2-e]pyrazin-4-one monohydro-chloride are thus obtained in the form of a beige-coloured solid melting above 260° C. [NMR spectrum: (300 MHz; DMSO-$d_6$; δ in ppm): 4.02 (s, 2H: —C$\underline{H}_2$— at 10); 7.00 (broad d, J=8 Hz, 1H: —$\underline{H}$7); 7.20 (broad s, 1H: —$\underline{H}$9); 7.74 (d, J=8 Hz, 1H: —$\underline{H}_6$); 7.77 and 8.07 (2 broad s, 1H each: —$\underline{H}$ of the imidazole); 12.65 (mult., 1H: —CO—N$\underline{H}$—)].

5H,10H-8—Nitroimidazo[1,2-a]indeno[1,2-e]-pyrazin-4-one may be prepared in the following way: 1 g of potassium nitrate is added over 10 minutes, at a temperature in the region of 5° C., to a solution of 2.6 g of 5H,10H-imidazo[1,2-a]indeno[1,2-e]pyrazin-4-one hydrochloride in 20 ml of concentrated sulphuric acid (d=1.83). The mixture is stirred for 30 minutes at the same temperature and for 3 hours at 25° C., then is poured onto 150 ml of ice-water. The crystals formed are isolated by filtration, washed with distilled water and then with acetone and dried under reduced pressure (1 mmHg; 0.13 kPa) at 80° C. 2.1 g of 8-nitro-5H,10H-imidazo[1,2-a]indeno[1,2-e]pyrazin-4-one are thus obtained, decomposing without melting above 300° C. [NMR spectrum: (200 MHz; DMSO-$d_6$; δ in ppm): 4.23 (s, 2H: —C$\underline{H}$2— at 10); 7.68 and 8.12 (2 broad s, 1H each: —$\underline{H}$ of the imidazole); 8.07 (dd, J=8.5 Hz, 1H: —$\underline{H}$6); 8.38 (dd, J=8.5 and 1.5 Hz, 1H: —$\underline{H}$7; 8.50 (d, J=1.5 Hz, 1H: —$\underline{H}$9); 12.64 (mult., 1H: —CON$\underline{H}$—)].

EXAMPLE 19

To a suspension of 0.6 g of 10-amino-5H,10H-imidazo[1,2-a]indeno[1,2-e]pyrazin-4-one hydrochloride in 30 ml of anhydrous dimethylformamide are added successively, at a temperature in the region of 20° C., 0.6 g of triethylamine and 0.42 g of nicotinoyl chloride hydrochloride. The mixture is stirred for 2 hours at the same temperature, the insoluble product formed is removed by filtration and the filtrate is concentrated to dryness under reduced pressure (15 mmHg; 2 kPa) at 80° C. The product obtained (1.04 g) is suspended for 10 minutes in 20 ml of boiling isopropanol and, after cooling and storing at 5° C. for 1 hour, is isolated by filtration, washed with 1 ml of chilled isopropanol and dried under reduced pressure (1 mmHg; 0.13 kPa) at 60° C. The product obtained (0.43 g) is suspended in 5 ml of methanol, isolated by filtration, washed with 2 ml of methanol and dried under reduced pressure (1 mmHg; 0.13 kPa) at 100° C. 0.24 g of 10-nicotinoylamino-5H,10H-imidazo[1,2-a]indeno[1,2-e]pyrazin-4-one are thus obtained, decomposing without melting above 260° C. (NMR spectrum: [200 MHz; $(CD_3)_2SO-d_6$; δ in ppm]: 6.42 (d, J=8.5 Hz, 1H: —C$\underline{H}$ 10); 7.40 and 7.51 (2 broad t, J=8 Hz, 1H each: —$\underline{H}$7 and —$\underline{H}$8); 7.58 and 7.92 (2 broad d, J=8 Hz, 1H each: —$\underline{H}$6 and —$\underline{H}$9); 7.62 and 7.74 (2s, 1H each: —$\underline{H}$ of the imidazole); 7.62 (dd, J=8.5 and 5 Hz, 1H: —$\underline{H}$ at 5 of the pyridine); 8.33 (broad d, J=8.5 Hz, 1H: —$\underline{H}$ at 4 of the pyridine); 8.79 (broad d, J=5 Hz, 1H: —$\underline{H}$ at 6 of the pyridine); 9.11 (mt, 1H: —$\underline{H}$ at 2 of the pyridine); 9.38 (d, J=8.5 Hz, 1H: —N$\underline{H}$CO— at 10); 12.63 (broad s, 1H: —CON$\underline{H}$ of the ring)).

EXAMPLE 20

To a suspension of 1.4 g of 10-amino-5H,10H-imidazo[1,2-a]indeno[1,2-e]pyrazin-4-one hydrochloride in 40 ml of anhydrous dimethylformamide are added successively over 5 minutes, at a temperature in the region of 5° C., 1.7 g of 3-carbomethoxypropionyl chloride and, over 5 minutes, a solution of 1.1 g of triethylamine in 3 ml of anhydrous dimethylformamide. The mixture is stirred for 30 minutes at the same temperature and then for 2 hours at a temperature in the region of 20° C. The insoluble product formed is isolated by filtration and washed with 10 ml of dimethylformamide, then the combined filtrate and washing are concentrated to dryness under reduced pressure (2 mmHg; 0.26 kPa) at 60° C. The product obtained (3 g) is suspended in 30 ml of methanol, isolated by filtration, washed with 5 ml of methanol and air-dried. Out of 0.4 g of product obtained in total, 0.3 g is suspended for 10 minutes in 3 ml of boiling methanol and, after cooling to 20° C., is isolated by filtration, washed with 0.5 ml of methanol and dried under reduced pressure (1 mmHg; 0.13 kPa) at 100° C. 0.25 g of methyl 3-[10-(4,5-dihydro-4-oxo-10H-imidazo[1,2-a]indeno[1,2-e]pyrazinyl)aminocarbonyl]-propionate is thus obtained, decomposing without melting above 260° C. (NMR spectrum: [300 MHz; $(CD_3)_2SO-d_6$; δ in ppm]: from 2.50 to 2.70 (mt, 4H: —CO—C$\underline{H}$—C$\underline{H}_2$—CO—); 3.64 (s, 3H: —COOC$\underline{H}_3$); 6.18 (d, J=8.5 Hz, 1H: —C$\underline{H}$— 10); 7.38 and 7.48 (2 broad t, J=7.5 Hz, 1H each: —$\underline{H}$ 7 and —$\underline{H}$ 8); 7.50 and 7.87 (2 broad d, J=7.5 Hz, 1H each: —$\underline{H}$ 6 and —$\underline{H}$ 9); 7.60 (s, 2H: —$\underline{H}$ of the imidazole); 8.65 (d, J=8.5 Hz, 1H: —N$\underline{H}$CO— at 10); 12.51 (broad s, 1H: —CON$\underline{H}$— of the ring)).

EXAMPLE 21

To a suspension of 2.75 g of 10-amino-5H,10H-imidazo[1,2-a]indeno[1,2-e]pyrazin-4-one hydrochloride in 80 ml of anhydrous dimethylformamide are added, at a temperature in the region of 5° C., 8 g of 3-(diethyl-amino)propionyl chloride hydrochloride and, over 10 minutes, a solution of 4 g of triethylamine in 10 ml of anhydrous dimethylformamide. The mixture is stirred for 30 minutes at the same temperature and then for 16 hours at a temperature in the region of 20° C. The insoluble product formed is isolated by filtration and washed with 10 ml of dimethylformamide, then the combined filtrate and washing are concentrated to dryness under reduced pressure (2 mmHg; 0.26 kPa) at 60° C. The product obtained (12 g) is chromatographed on 120 g of neutral silica gel (0.020–0.045 mm) contained in a column 2.6 cm in diameter, eluting under pressure with a chloroform/methanol/28% aqueous ammonia mixture (82/15/3 by volume) and collecting 50 ml fractions. Fractions 13 to 35 are combined and concentrated to dryness under reduced pressure (15 mmHg; 2 kPa) at 40° C. The product obtained (1.44 g) is chromatographed on 500 g of neutral silica gel (0.020–0.045 mm) contained in a column 5.4 cm in diameter, eluting with a chloroform/methanol/28% aqueous ammonia mixture (82/15/3 by volume) and collecting 30 ml fractions. Fractions 5 to 35 are combined and concentrated to dryness under reduced pressure (15 mmHg; 2 kPa) at 40° C. Out of 1.15 g of product obtained in total, 0.88 g is chromatographed on 90 g of neutral silica gel (0.020–0.045 mm) contained in a column 3 cm in diameter, eluting with a chloroform/methanol/28% aqueous ammonia mixture (70/26/4 by volume) and collecting 30 ml fractions. Fractions 7 and 8 are combined and concentrated to dryness under reduced pressure (15 mmHg; 2 kPa) at 40° C. The product obtained (0.28 g) is suspended in 10 ml of ethyl ether, isolated by filtration, washed with 1 ml of ethyl ether and dried under reduced pressure (1 mmHg; 0.13 kPa) at 100° C. 0.22 g of 10-(3-diethylaminopropionamido)-5H,10H-imidazo[1,2-a]indeno[1,2-e]pyrazin-4-one is thus obtained, decomposing without melting at about 260° C. (NMR spectrum: [300 MHz; $(CD_3)_2SO-d_6$; δ in ppm]: 0.90 (t, J=7.5 Hz, 3H: —C$\underline{H}_3$); from 2.20 to 2.55 [mt, 6H: —C$\underline{H}_2$—N(C$\underline{H}_2$)$_2$]; 2.70 uncoupled ab, $J_{ab}$=14 Hz, 2H: —CO—C$\underline{H}_2$—); 6.17 (d, J=8.5 Hz, 1H: —C$\underline{H}$ 10); 7.34 and 7.45 (2 broad t, J=8 Hz, 1H each: —$\underline{H}$ 7 and —$\underline{H}$ 8); 7.47 and 7.84 (2 broad d, J=8 Hz, 1H each: —$\underline{H}$ 6 and —$\underline{H}$ 9); 7.55 and 7.68 (2s, 1H each: —$\underline{H}$ of the imidazole); 8.60 (d, J=8.5 Hz, 1H: —N$\underline{H}$CO— at 10); 12.45 (broad s, 1H: —CON$\underline{H}$— of the ring)).

EXAMPLE 22

A mixture of 21.4 g of acetic anhydride and 11.5 g of formic acid is heated for 2 hours at a temperature between 50° C. and 60° C., and cooled to 20° C. 0.9 g of anhydrous sodium acetate is then added followed, after dissolution, by 2.75 g of 10-amino-5H,10H-imidazo[1,2-a]indeno[1,2-e]pyrazin-4-one hydrochloride. The mixture is stirred for 1 hour at 20° C. and concentrated to dryness under reduced pressure (15 mmHg; 2 kPa) at 50° C. The product obtained (4.3 g) is dissolved in 50 ml of dimethylformamide and, after addition of decolorizing charcoal, the solution is filtered. 200 ml of distilled water are then added to the filtrate and the mixture is stored for 1 hour at a temperature in the region of 5° C. The insoluble product formed is isolated by filtration, washed with 10 ml of distilled water and dried under reduced pressure (1 mmHg; 0.13 kPa) at 100° C. 1.2 g of 10-formamido-5H,10H-imidazo[1,2-a]indeno[1,2-e]pyrazin-4-one are thus obtained, melting at 280° C. (decomposition) (NMR spectrum: [200 MHz; $(CD_3)_2SO-d_6$; δ in ppm]: 6.22 (d, J=8.5 Hz, 1H: —C$\underline{H}$— 10); 7.36 and 7.45 (2 broad t, J=8 Hz, 2H: —$\underline{H}$ 7 and —$\underline{H}$ 8); 7.51 and 7.87 (2 broad d, J=8 Hz, 2H: —$\underline{H}$ 6 and —$\underline{H}$ 9); 7.58 and 7.64 (2s, 1H each: —$\underline{H}$ of the imidazole); 8.44 (s, 1H: —C$\underline{H}$=O); 8.78 (d, J=8.5 Hz, 1H: —CON$\underline{H}$ at 10); 12.50 (broad s, 1H: —CON$\underline{H}$— of the ring)).

EXAMPLE 23

To a suspension of 0.55 g of 10-amino-5H,10H-imidazo[1,2-a]indeno[1,2-e]pyrazin-4-one hydrochloride in 15 ml of anhydrous dimethylformamide are added successively, at a temperature in the region of 5° C., 1 g of R(−)-α-methoxy-α-trifluoromethylphenylacetyl chloride and, over 5 minutes, a solution of 0.4 g of triethylamine in 1.5 ml of anhydrous dimethylformamide. After stirring for 30 minutes at the same temperature, the insoluble product formed is isolated by filtration and washed twice with 3 ml in total of dimethylformamide, then the combined filtrate and washing are concentrated to dryness under reduced pressure (2 mmHg; 0.26 kPa) at 60° C. The product obtained (2 g) is suspended in 25 ml of methanol and, after addition of 25 ml of distilled water and stirring for 30 minutes, the insoluble product is isolated by filtration, washed twice with 10 ml in total of distilled water and dried under reduced pressure (1 mmHg; 0.13 kPa) at 100° C. 0.44 g of a 50/50 mixture of the following 2 diastereoisomers is thus obtained: (10R)-10[(R)-α-methoxy-α-trifluoromethylphenylacetamido]-5H,10H-imidazo[1,2-a]indeno[1,2-e]pyrazin-4-one and (10S)-10[(R)-α-methoxy-α-trifluoromethylphenylacetamido]-5H,10H-imidazo[1,2-a]indeno[1,2-e]pyrazin-4-one (NMR spectrum: [200 MHz; $(CD_3)_2SO\text{-}d_6$; δ in ppm]: 50/50 mixture of two diastereoisomers: 3.39 and 3.43 (2s, 3H: —OC$\underline{H}_3$); 6.19 and 6.20 (2d, J=8.5 Hz, 1H: —C$\underline{H}$— 10); from 7.10 to 7.70 and 7.84 [mt and d respectively (J=8 Hz), 10H and 1H: —$\underline{H}$ 6 —$\underline{H}$ 7 —$\underline{H}$ 8 and —$\underline{H}$9 aromatic —$\underline{H}$ of the phenyl and —$\underline{H}$ of the imidazole]; 9.14 and 9.19 (2d, J=8.5 Hz, 1H: —N$\underline{H}$CO— at 10); 12.45 and 12.47 (2 broad s, 1H: —CON$\underline{H}$— of the ring)).

EXAMPLE 24

To a suspension of 0.55 g of 10-amino-5H,10H-imidazo[1,2-a]indeno[1,2-e]pyrazin-4-one hydrochloride in 30 ml of anhydrous dimethylformamide are added successively, at a temperature in the region of 5° C., 0.73 g of 4-phenylbutyryl chloride and, over 5 minutes, a solution of 0.4 g of triethylamine in 2 ml of anhydrous dimethylformamide. After stirring for 1 hour 30 minutes at the same temperature and then for 1 hour at 20° C., the insoluble product formed is isolated by filtration and washed twice with 3 ml in total of dimethylformamide. The filtrate and washing are combined, 80 ml of distilled water are added and the insoluble product formed is isolated by filtration, washed twice with 2 ml in total of distilled water and with 3 ml of acetone and then air-dried. The product obtained (0.27 g) is suspended for 5 minutes in 3 ml of boiling methanol and, after cooling and storing for 1 hour at 5° C., the solid formed is isolated by filtration, washed with 0.5 ml of methanol and dried under reduced pressure (5 mmHg; 0.65 kPa) at 60° C. 0.15 g of 10-(4-phenylbutyramido)-5H,10H-imidazo-[1,2-a]indeno[1,2-e]pyrazin-4-one is thus obtained, decomposing without melting above 260° C. (NMR spectrum: [200 MHz; $(CD_3)_2SO\text{-}d_6$; δ in ppm]: 2.92 (mt, 2H: —C$\underline{H}_2$—); 2.28 (t, J=7.5 Hz, 2H: —C$\underline{H}_2$—Ar); 2.62 (t, J=7.5 Hz, 2H: —CO—C$\underline{H}_2$—); 6.18 (d, J=8.5 Hz, 1H: —C$\underline{H}$— 10); from 7.10 to 7.55 (mt, 7H: —$\underline{H}$ of the phenyl —$\underline{H}$7 and —$\underline{H}$ 8); 7.50 and 7.87 (2 broad d, J=8 Hz, 1H each: —$\underline{H}$ 6 and —$\underline{H}$ 9); 7.55 and 7.60 (2s, 1H each; —$\underline{H}$ of the imidazole); 8.53 (d, J=8.5 Hz, 1H: —N$\underline{H}$CO— at 10); 12.47 (broad s, 1H: —CON$\underline{H}$— of the ring)).

EXAMPLE 25

To a suspension of 0.55 g of 10-amino-5H,10H-imidazo[1,2-a]indeno[1,2-e]pyrazin-4-one hydrochloride in 30 ml of anhydrous dimethylformamide are added successively, at a temperature in the region of 5° C., 0.63 g of phenylacetyl chloride and, over 5 minutes, a solution of 0.4 g of triethylamine in 2 ml of anhydrous dimethylformamide. After stirring for 1 hour at the same temperature and then for 30 minutes at 20° C., the insoluble product formed is isolated by filtration and washed twice with 3 ml in total of dimethylformamide. The filtrate and the washing are combined, 80 ml of distilled water are added and the insoluble product formed is isolated by filtration, washed twice with 2 ml in total of distilled water and then air-dried. The product obtained (0.27 g) is suspended for 5 minutes in 3 ml of boiling methanol and, after cooling and storing for 1 hour at 5° C., the solid formed is isolated by filtration, washed twice with 1 ml in total of methanol and dried under reduced pressure (5 mmHg; 0.65 kPa) at 60° C. 0.16 g of 10-phenylacetamido-5H,10H-imidazo[1,2-a]indeno[1,2-e]-pyrazin-4-one is thus obtained, decomposing without melting above 260° C. (NMR spectrum: [300 MHz; $(CD_3)_2SO\text{-}d_6$; δ in ppm): 3.56 (s, 2H: Ar—C$\underline{H}_2$—CO—); 6.12 (d, J=8.5 Hz, 1H: —C$\underline{H}$— 10); from 7.25 to 7.60 (mt, 7H: —$\underline{H}$ of the phenyl —$\underline{H}$ 7 and —$\underline{H}$ 8); 7.38 and 7.48 (2s, 1H each: —$\underline{H}$ of the imidazole); 7.45 and 7.86 (2 broad d, J=8 Hz, 1H each: —$\underline{H}$ 6 and —$\underline{H}$ 9); 8.83 (d, J=8.5 Hz, 1H: —N$\underline{H}$CO— at 10); 12.50 (broad s, 1H: —CON$\underline{H}$— of the ring)).

EXAMPLE 26

To a suspension of 1.62 g of 10-amino-5H,10H-imidazo[1,2-a]indeno[1,2-e]pyrazin-4-one hydrochloride in 45 ml of anhydrous dimethylformamide are added successively, at a temperature in the region of 5° C., 1.98 g of di-tert-butyl dicarbonate and, over 5 minutes, a solution of 0.87 g of triethylamine in 3 ml of anhydrous dimethylformamide. After stirring for 30 minutes at the same temperature and then for 16 hours at 20° C., the insoluble product formed is isolated by filtration, suspended in 10 ml of distilled water, isolated again by filtration, washed 3 times with 15 ml in total of distilled water and dried under reduced pressure (1 mmHg; 0.13 kPa) at 100° C. 0.64 g of tert-butyl N-[10-(4,5-dihydro-4-oxo-1OH-imidazo[1,2-a)-indeno[1,2-e]pyrazinyl)carbamate is thus obtained, decomposing without melting at 240° C. (NMR spectrum: [300 MHz; $(CD_3)_2SO\text{-}d_6$; δ in ppm]: 1.40 [s, 9H: —C(C$\underline{H}_3$)$_3$]; 5.83 (d, J=9 Hz, 1H: —C$\underline{H}$— 10); 7.35 and 7.45 (2 broad t, J=8 Hz, 1H each: —$\underline{H}$ 7 and —$\underline{H}$ 8); 7.51 and 7.83 (2 broad d, J=8 Hz, 1H each: —$\underline{H}$ 6 and —$\underline{H}$ 9); from 7.55 to 7.65 (mt, 3H: —$\underline{H}$ of the imidazole and —N$\underline{H}$CO— at 10); 12.48 (broad s, 1H: —CON$\underline{H}$— of the ring)).

EXAMPLE 27

To a suspension of 1.4 g of 10-amino-5H,10H-imidazo[1,2-a]indeno[1,2-e]pyrazin-4-one hydrochloride in 25 ml of acetic acid are added 0.41 g of anhydrous sodium acetate and 0.66 g of 2,5-dimethoxytetrahydrofuran. The mixture is stirred at boiling for 1 hour 30 minutes and, after cooling to 20° C., the solid formed is isolated by filtration, washed twice with 30 ml in total of distilled water and air-dried. The product obtained (2.45 g) is chromatographed on 25 g of neutral silica gel (0.06–0.20 mm) contained in a column 2.4 cm in diameter, eluting with a dichloromethane/methanol mixture (90/10 by volume) and collecting an 18 ml fraction and a 540 ml fraction. After addition of decolorizing charcoal, the latter fraction is filtered and the filtrate is concentrated to dryness under reduced pressure (15 mmHg; 2 kPa) at 40° C. The product obtained is suspended for 10 minutes in 5 ml of methanol and then isolated by filtration, washed with 1 ml of methanol and dried under reduced pressure (1 mmHg; 0.13 kPa) at 100° C. 0.6 g of 10-(1-pyrrolyl)-5H,10H-imidazo[1,2-a]indeno[1,2-e]pyrazin-4-one is thus obtained, decomposing without melting above 260° C. (NMR spectrum: [200 MHz; $(CD_3)_2SO\text{-}d_6$; δ in ppm]: 6.12 (t, J=2 Hz, 2H: —$\underline{H}$ 3 and —$\underline{H}$ 4 of the pyrrole); 6.61 (s, 1H: —C$\underline{H}$— 10); 6.91 (t, J=2 Hz, 2H: —$\underline{H}$ 2 and —$\underline{H}$ 5 of the pyrrole); 7.08 and 7.34 (2 broad s, 1H each: —$\underline{H}$ of the imidazole); from 7.30 to 7.55 and 7.93 [mt and d respectively (J=7.5 Hz), 3H and 1H: —$\underline{H}$ 6, —$\underline{H}$ 7, —$\underline{H}$ 8 and —$\underline{H}$ 9]; 12.60 (broad s, 1H: —CON$\underline{H}$—)).

EXAMPLE 28

To a suspension of 1.3 g of 10-amino-5H,10H-imidazo[1,2-a]indeno[1,2-e]pyrazin-4-one hydrochloride in 25 ml of acetic acid are added 0.39 g of anhydrous sodium acetate and 1 g of methyl 2,5-dimethoxytetrahydrofuran-2-carboxylate. The mixture is stirred for 1 hour at boiling and for 16 hours at a temperature in the region of 20° C. The solid formed is removed by filtration and the filtrate is concentrated to dryness under reduced pressure (15 mmHg; 2 kPa) at 40° C. The product obtained (1.63 g) is suspended in 10 ml of 1N hydrochloric acid, isolated by filtration, washed with 2.5 ml of 1N hydrochloric acid and with 2.5 ml of methanol and then dried under reduced pressure (1 mmHg; 0.13 kPa) at 100° C. 1.1 g of methyl 1-[10-(4,5-dihydro-4-oxo-10H-imidazo[1,2-a]indeno[1,2-e]pyrazinyl)]-pyrrole-2-carboxylate are thus obtained, melting at 245° C. (decomposition) (NMR spectrum: [200 MHz; $(CD_3)_2SO-d_6$; δ in ppm]: 3.91 (s, 3H: —COOC$\underline{H}_3$); 6.10 (dd, J=3 and 2 Hz, 1H: —$\underline{H}$ 4 of the pyrrole), 6.85 (dd, J=2 and 1.5 Hz, 1H: —$\underline{H}$ 3 of the pyrrole), 7.09 (dd, J=3 and 1.5 Hz, 1H: —$\underline{H}$ 5 of the pyrrole); 7.19 (s, 1H: —C$\underline{H}$— 10); 7.29 and 7.56 (2s, 1H each: —$\underline{H}$ of the imidazole); from 7.20 to 7.60 and 7.97 [mt and d respectively (J=7.5 Hz), 3H and 1H: —$\underline{H}$ 6, —$\underline{H}$ 7, —$\underline{H}$ 8 and —$\underline{H}$ 9]; 12.78 (broad s, 1H: —CON$\underline{H}$—)).

EXAMPLE 29

0.1 g of sodium is dissolved in 3 ml of liquid ammonia at −33° C., followed by portionwise addition of 0.3 g of 10-hydroxyimino-5H,10H-imidazo[1,2-a]indeno[1,2-e]pyrazin-4-one. After stirring for 30 minutes, 0.3 g of methyl iodide is added dropwise and the stirring is continued for 4 hours at the same temperature and then for 16 hours while allowing the temperature to return gradually to 20° C. The solid obtained is suspended in a solution of 0.25 g of ammonium chloride in 20 ml of distilled water and, after stirring for 15 minutes, it is filtered and washed with distilled water. The solid obtained is suspended in 50 ml of boiling ethanol, filtered at 20° C., washed twice with 10 ml in total of ethyl ether and dried under reduced pressure (1 mmHg; 0.13 kPa) at 100° C. 0.2 g of 10-methoxyimino-5H,10H-imidazo[1,2-a]indeno[1,2-e]pyrazin-4-one is thus obtained as a 95/5 mixture of the E and Z forms, subliming at 310° C. (NMR spectrum: [200 MHz; $(CD_3)_2SO-d_6$; δ in ppm]: 4.22 (s, 3H: =NOC$\underline{H}_3$); 7.37 and 7.50 (2 broad t, J=8 Hz, 1H each: —$\underline{H}$ 7 and —$\underline{H}$ 8); 7.57 and 8.01 (2s, 1H each: —$\underline{H}$ of the imidazole); 7.76 and 8.00 (2 broad d, J=8 Hz, 1H each: —$\underline{H}$ 6 and —$\underline{H}$ 9); from 12.50 to 13.00 (broad mult., 1H: —CON$\underline{H}$—)).

EXAMPLE 30

To a suspension of 3.54 g of 10-acetamido-5H,10H-imidazo[1,2-a]indeno[1,2-e]pyrazin-4-one in 80 ml of anhydrous dimethyl sulphoxide, maintained at 20° C. under a nitrogen atmosphere, is added 0.86 g of 80% sodium hydride and the mixture is stirred for 20 minutes. A solution of 1.7 g of methyl iodide in 8 ml of anhydrous dimethyl sulphoxide is then added dropwise over 5 minutes at the same temperature, the mixture is stirred for 1 hour and 40 ml of distilled water are added slowly. After stirring for 16 hours, the mixture is poured onto a mixture of 200 g of ice and 560 ml of distilled water, then the pH is adjusted to 4 by addition of 4 ml of acetic acid. The mixture is centrifuged so as to remove the tarry part and to recover the supernatant suspension, which is concentrated to dryness under reduced pressure (1 mmHg; 0.13 kPa) at 60° C. The product obtained (10 g) is suspended in 200 ml of distilled water, isolated by filtration, washed twice with 80 ml in total of distilled water and dried under reduced pressure (1 mmHg; 0.13 kPa) at 100° C. The product obtained (1.6 g) is suspended for 10 minutes in 20 ml of boiling ethanol and, after storing for 1 hour at 5° C., is then isolated by filtration, washed twice with 4 ml in total of chilled ethanol and dried under reduced pressure (15 mmHg; 2 kPa) at 20° C. The product obtained (1.4 g) is suspended for 10 minutes in 20 ml of boiling ethanol and, after storing for 1 hour at 5° C., is then isolated by filtration, washed twice with 4 ml in total of chilled ethanol and dried under reduced pressure (1 mmHg; 0.13 kPa) at 40° C. 1.28 g of 10-acetamido-10-methyl-5H,10H-imidazo[1,2-a]indeno[1,2-e]pyrazin-4-one are thus obtained, decomposing without melting above 260° C. (NMR spectrum: [200 MHz; $(CD_3)_2SO-d_6$; δ in ppm]: 1.61 and 1.79 (2s, 3H each: —C$\underline{H}_3$ at 10 and —NHCOC$\underline{H}_3$ at 10); 7.28 and 7.36 (2t, J=7.5 Hz, 1H each: —$\underline{H}$ 7 and —$\underline{H}$ 8); 7.43 and 7.80 (2d, J=7.5 Hz, 1H each: —$\underline{H}$ 6 and —$\underline{H}$ 9); 7.63 and 7.91 (2s, 1H each: —$\underline{H}$ of the imidazole); 8.63 (s, 1H: —N$\underline{H}$CO— at 10); 12.41 (s, 1H: —N$\underline{H}$CO— of the ring)).

EXAMPLE 31

A suspension of 1 g of 10-acetamido-10-methyl-5H,10H-imidazo[1,2-a]indeno[1,2-e]pyrazin-4-one in 50 ml of 2N hydrochloric acid is boiled for 1 hour 45 minutes and the solution obtained is concentrated to dryness under reduced pressure (1 mmHg; 0.13 kPa) at 70° C. The product obtained (1.15 g) is dissolved in 100 ml of methanol and, after addition of decolorizing charcoal, the solution is filtered. 300 ml of acetone are added and, after storing for 1 hour at 5° C., the solid formed is isolated by filtration, washed twice with 10 ml in total of chilled acetone and dried under reduced pressure (1 mmHg; 0.13 kPa) at 100° C. 0.39 g of 10-amino-10-methyl-5H,10H-imidazo[1,2-a]indeno[1,2-e]pyrazin-4-one hydrochloride is thus obtained, decomposing without melting above 260° C. (NMR spectrum: [200 MHz; $(CD_3)_2SO-d_6$; δ in ppm]: 1.97 (s, 3H: —C$\underline{H}_3$ at 10); 7.48 and 7.55 (2t, J=7.5 Hz, 1H each: —$\underline{H}$ 7 and —$\underline{H}$ 8); 7.70 and 8.75 (2 broad s, 1H each: —$\underline{H}$ of the imidazole); 7.95 and 8.08 (2d, J=7.5 Hz, 1H each: —$\underline{H}$ 6 and —$\underline{H}$ 9); 9.39 (mult., 3H: —N$\underline{H}_3^+$Cl⁻ at 10); 12.64 (mult., 1H: —N$\underline{H}$CO—)).

EXAMPLE 32

The process is performed as in Example 3 but starting with 1.1 g of 10-(4-imidazolylmethylene)-5H,10H-imidazo[1,2-a]indeno[1,2-e]pyrazin-4-one, 250 ml of dimethylformamide, 5 ml of acetic acid and 0.1 g of 10% palladium-on-charcoal. After evaporation of the solvents, the crude product is purified by chromatography on a column of silica (100 g partially deactivated with 3% water), eluting with a mixture of chloroform, methanol and 28% aqueous ammonia (24/6/1 by volume). A pale yellow solid is obtained which is triturated with 20 ml of water, filtered, washed with 20 ml of ethyl ether and dried at 80° C. under vacuum (2 mmHg; 0.26 kPa) to give 0.16 g of 10-(4-imidazolylmethyl)-5H,10H-imidazo[1,2-a]indeno[1,2-e]pyrazin-4-one in the form of an off-white solid melting above 260° C. (Analysis, % calculated C: 67.32, H: 4.32, N: 23.09, O: 5.27, % found C: 67.7, H: 4.2, N: 22.6).

10-(4-Imidazolylmethylene)-5H,10H-imidazo-[1,2-a]indeno[1,2-e]pyrazin-4-one may be prepared in the following way: the process is performed as in Example 3 but starting with 3 g of 5H,10H-imidazo-(1,2-a]indeno[1,2-e]pyrazin-4-one, 70 ml of dimethyl sulphoxide, 1.44 g of 4-imidazolecarboxaldehyde and 1.8 g of 80% sodium hydride. After treatment of the reaction mixture with 300 ml of ice-water and 4 ml of acetic acid, the suspension is filtered; the insoluble product is triturated with 50 ml of dimethyl sulphoxide, followed by addition of 100 ml of water. The precipitate obtained is treated successively with 50 ml of water, 50 ml of dichloromethane and 50 ml of methanol. After air-drying, 3 g of 10-(4-imidazolylmethylene)-5H,10H-imidazo[1,2-a]indeno[1,2-e] pyrazin-4-one are obtained in the form of a black solid which is used without further purification in the subsequent syntheses. MS s/z 302 (MH+).

4-Imidazolecarboxaldehyde may be prepared according to the process described by E. P. Papadopoulos et al., J. Org. Chem., 31, 615 (1966).

EXAMPLE 33

To a mixture, stirred at a temperature in the region of 20° C., of 0.96 g of 10-methyl-5H,10H-imidazo[1,2-a]indeno[1,2-e]pyrazin-4-one, 50 ml of dimethylformamide and 0.66 g of 80% sodium hydride is added, under cover of argon, 0.56 ml of trimethylchlorosilane. The stirring is continued for 30 minutes, followed by addition of 0.44 ml of 1-bromo-3-chloropropane, and the stirring is continued for 25 minutes. A catalytic amount of sodium iodide and 0.35 g of imidazole are then added. The stirring is continued for 1 hour 30 minutes, then at 50° C. for 18 hours. The reaction mixture is poured into 20 ml of water and 2 ml of acetic acid and the brown solution obtained is concentrated on a rotary evaporator, 20 ml of water are added and the solution is again evaporated. The evaporation residue is triturated three times with ethyl acetate (3×25 ml), filtered each time, and then treated with 25 ml of hot isopropanol and immediately filtered. The isopropanol filtrate is evaporated to give a foamy red solid which is purified by chromatography on a column of silica (50 g), eluting with a mixture of dichloromethane and methanol (95/5 by volume). After drying at 60° C. under vacuum, (1 mmHg; 0.26 kPa), 0.35 g of 10-[3-(imidazol-1-yl)propyl]-10-methyl-5H,10H-imidazo[1,2-a]indeno[1,2-e]pyrazin-4-one is obtained in the form of a white solid melting at about 210° C. (Analysis, % calculated C: 69.55, H: 5.54, N: 20.28, O: 4.63, % found C: 69.8, H: 5.9, N: 20.1).

10-Methyl-5H,10H-imidazo[1,2-a]indeno-[1,2-e]pyrazin-4-one may be obtained in the following way: a mixture of 1 g of 10-hydroxymethylene-5H,10H-imidazo[1,2-a]indeno[1,2-e]pyrazin-4-one, 80 ml of dimethylformamide and 20 ml of methanol is hydrogenated at a temperature in the region of 20° C. and at normal pressure for 4 hours in the presence of 10% palladium-on-charcoal. After filtration of the catalyst under an inert atmosphere, the solvents are evaporated off and the beige-coloured solid obtained (1.25 g) is purified by chromatography on a column of silica (100 g) with a mixture of dichloromethane and methanol (95/5 by volume). After drying at 90° C., 0.35 g of 10-methyl-5H,10H-imidazo[1,2-a]indeno[1,2-e]pyrazin-4-one is obtained in the form of a cream-coloured solid melting above 260° C. (Analysis, % calculated C: 70.87, H: 4.67, N: 17.71, O: 6.74, % found C: 70.5, H: 4.4, N: 17.4).

10-Hydroxymethylene-5H,10H-imidazo[1,2-a]-indeno[1,2-e]pyrazin-4-one may be obtained in the following way: a solution of 1.4 g of 10-dimethylaminomethylene-5H,10H-imidazo[1,2-a]indeno-[1,2-e]pyrazin-4-one in 35 ml of 5N hydrochloric acid is stirred for 30 minutes at a temperature in the region of 25° C. After addition of 60 ml of water and neutralization with 120 ml of saturated aqueous sodium hydrogen carbonate, the solid formed is isolated by filtration, washed twice with 60 ml in total of water and air-dried. The product obtained (1.1 g) is dissolved in 120 ml of dimethyl sulphoxide and, after addition of 120 ml of water, the solid formed is isolated by filtration, washed twice with 10 ml in total of distilled water and twice with 10 ml in total of acetone and then dried under reduced pressure (1 mmHg; 0.13 kPa) at 100° C. 1 g of 10-hydroxymethylene-5H,10H-imidazo[1,2-a]indeno[1,2-e]pyrazin-4-one is thus obtained as a 60/40 mixture of the Z and E forms, decomposing without melting at 290° C. [NMR spectrum: (200 MHz; DMSO-d$_6$; δ in ppm): a 60/40 mixture of isomers is observed: from 7.20 to 7.40 (mt, 2H: —H7 and —H8); 7.56 and 7.64–8.29 and 8.79 (4 broad s, twice 1H: —H of the imidazole); from 7.80 to 8.15 (mt, 2H: —H6 and —H9); 8.21 and 8.24 (2s, 1H in total: =CH—O—); 12.43 (mult., 1H: —NH—)].

10-Dimethylaminomethylene-5H,10H-imidazo-[1,2-a]indeno[1,2-e]pyrazin-4-one may be prepared in the following way: 6.3 g of t-butoxybis(dimethylamino)-methane are added dropwise over 5 minutes, at a temperature in the region of 25° C., to a suspension of 5.5 g of 5H,10H-imidazo[1,2-a]indeno[1,2-e]pyrazin-4-one in 100 ml of dimethylformamide. After stirring for 30 minutes at the same temperature, the mixture is poured into 500 ml of distilled water and extracted 5 times with 1.5 liters in total of chloroform. The organic extracts are combined, washed with 250 ml of distilled water, dried over anhydrous magnesium sulphate and concentrated to dryness under reduced pressure (15 mmHg; 2 kPa) at 60° C. The product obtained (4.5 g) is suspended in 25 ml of methanol, filtered off, washed twice with 20 ml in total of methanol and dried under reduced pressure (15 mmHg; 2 kPa) at 20° C. The product obtained (4.5 g) is dissolved in 45 ml of boiling dimethyl2formamide and, after cooling, the solution is stored for 4 hours at a temperature in the region of 5° C. The crystals are isolated by filtration, washed successively with 10 ml of dimethylformamide and 10 ml of acetone, and dried to dryness under reduced pressure (1 mmHg; 0.13 kPa) at 100° C. 4 g of 10-(E-dimethylaminomethylene-5H,10H-imidazo[1,2-a)indeno-[1,2-e]pyrazin-4-one are thus obtained, melting at 293° C. [NMR spectrum: (200 MHz; DMSO-d$_6$; δ in ppm): 3.35 [S 6H: —N(CH$_3$)$_2$1; 7.18 and 7.28 (2t, J=7.5 Hz, 2H: —H7 and —H8); 7.48 and 7.92 (2d, J=7.5 Hz, 1H each: —H6 and —H9); 7.63 and 8.50 (2 broad s, 1H each: —H of the imidazole); 8.09 (s, 1H: =CH—N); 12.30 (mult., 1H: —NH—)].

EXAMPLE 34

The process is performed as in Example 33 but starting with 0.48 g of 10-methyl-5H,10H-imidazo[1,2-a]indeno[1,2-e]pyrazin-4-one, 25 ml of dimethylformamide, 0.33 g of 80% sodium hydride, 0.30 ml of trimethylchlorosilane, 0.25 ml of 1-bromo-3-chlorobutane and 0.15 g of imidazole. After chromatography on a column of silica (20 g), eluting with a mixture of chloroform, methanol and 28% aqueous ammonia (90/7/3 by volume), 0.26 g of 10-[4-(imidazol-1-yl)butyl]-10-methyl-5H,10H-imidazo[1,2-a]indeno-[1,2-e]pyrazin-4-one is obtained in the form of a cream-coloured solid melting at about 160° C. (Analysis, % calculated C: 70.18, H: 5.89, N: 19.48, O: 4.45, % found C: 70.3, H: 6.0, N: 19.6).

EXAMPLE 35

To 7 g of 8-amino-10-acetamido-10-methyl-5H,10H-imidazo[1,2-a]indeno[1,2-e]pyrazin-4-one dissolved in 130 ml of dimethylformamide at a temperature in the region of 20° C. are added dropwise 4.7 ml of methyl isocyanate. The stirring is continued for 15 hours at the same temperature. The reaction medium is concentrated to dryness under reduced pressure (15 mmHg; 2 kPa) and the residue is then taken up in water and ethyl acetate. The insoluble product thus formed is filtered off, washed with water and with ethyl acetate, then taken up in 20 ml of 6N hydrochloric acid and refluxed for 2 hours. After cooling to a temperature in the region of 20° C., the precipitate obtained is filtered off and washed with acetone to give 0.6 g of 10-amino-10-methyl-8-(3-methylureido)-5H,10H-imidazo[1,2-a]indeno[1,2-e]-pyrazin-4-one dihydrochloride hydrate in the form of a pale yellow powder, the melting point of which is greater than 260° C. (Analysis, $C_{16}H_{16}N_6O_2.1.0\ H_2O.2.38\ HCl$, % calculated C: 59.25; H: 4.97; N: 25.91; % found C: 59.3; H: 4.7; N: 25.6).

8-Amino-10-acetamido-10-methyl-5H,10H-imidazo[1,2-a]indeno[1,2-e]pyrazin-4-one may be obtained according to the following procedure: 12 g of 8-nitro-10-acetamido-10-methyl-5H,10H-imidazo [1,2-a]indeno[1,2-e]pyrazin-4-one are hydrogenated at atmospheric pressure in 200 ml of dimethylformamide in the presence of 1.5 g of 10% palladium-on-charcoal at a temperature in the region of 20° C. After filtration of the catalyst on a bed of Celite and washing with dimethyl sulphoxide, the filtrate is concentrated to dryness under reduced pressure (15 mmHg; 2 kPa) and the residue is recrystallized from aqueous ethanol containing 25% of water to give 7.7 g of expected product in the form of a rust-coloured crystalline powder, the melting point of which is greater than 260° C.

8-Nitro-10-acetamido-10-methyl-5H,10H-imidazo[1,2-a]indeno[1,2-e]pyrazin-4-one may be prepared according to the following method: to 150 ml of concentrated sulphuric acid cooled to 5° C. are gradually added 13.6 g of 10-acetamido-10-methyl-5H,10H-imidazo[1,2-a]indeno[1,2-e]pyrazin-4-one followed, after stirring for 30 minutes at 10° C., by 4.67 g of potassium nitrate in a single portion. The reaction is continued for 90 minutes at the same temperature. The reaction medium is run onto 1 liter of ice-water and the precipitate formed is filtered off, washed with water and dried. 12 g of expected product are thus obtained in the form of a yellow solid, the melting point of which is greater than 260° C.

EXAMPLE 36

To 11 g of 8-amino-10-(carboxymethylene)-5H,10H-imidazo[1,2-a]indeno[1,2-e]pyrazin-4-one dihydrochloride dissolved in 110 ml of dimethylformamide and 110 ml of dioxane at a temperature in the region of 20° C. are added 12.42 g of potassium carbonate, followed by dropwise addition of 5.3 ml of methyl isocyanate. The stirring is continued for 30 hours at the same temperature. The reaction medium is then filtered. The solid recovered is dried under reduced pressure (15 mmHg; 2 kPa). The residue is taken up in 50 ml of water and the precipitate is filtered off. The solid is acidified with 2 ml of concentrated hydrochloric acid in 50 ml of water and then filtered and dried under reduced pressure (15 mmHg; 2 kPa). The insoluble product thus formed is taken up in 700 ml of dimethylformamide and brought to 50° C. in the presence of 1 g of animal black. The solution is filtered on Celite and the filtrate is concentrated on a rotary evaporator at 40° C. under reduced pressure (15 mmHg; 2 kPa). (1 mmHg; 0.13 kPa). The residue is taken up in 200 ml of ethyl ether and then filtered and dried for 8 hours at 50° C. under reduced pressure (1 mmHg; 0.13 kPa). 3.67 g of 10-(carboxymethylene)-8-(3-methylureido)-5H, 10H-imidazo(1,2-a]indeno[1,2-e]pyrazin-4-one are obtained in the form of an orange-coloured powder, the melting point of which is greater than 260° C. (Analysis, $C_{17}H_{13}N_5O_4.0.9\ DMF.0.9\ H_2O$, % calculated C: 58.12; H: 3.73; N: 19.93, % found C: 58.1; H: 3.4; N: 19.6).

8-Amino-10-(carboxymethylene)-5H,10H-imidazo-[1,2-a]indeno[1,2-e]pyrazin-4-one dihydrochloride may be obtained according to the following procedure: 35.5 g of 8-nitro-10-(carboxymethylene)-5H,10H-imidazo-[1,2-a] indeno[1,2-e]pyrazin-4-one are added to 74.5 g of stannous chloride dihydrate in 550 ml of concentrated hydrochloric acid, followed by heating at 40° C. for 4 hours. After cooling to 25° C., the mixture is filtered and then washed with 3 times 200 ml of distilled water and twice 100 ml of acetone. The solid is dried at 60° C. under reduced pressure (1 mmHg; 0.13 kPa). 37.45 g of 8-amino-10-(carboxymethylene)-5H,10H-imidazo[1,2-a]indeno[1,2-e] pyrazin-4-one dihydrochloride are obtained in the form of a yellow solid, the melting point of which is greater than 260° C.

8-Nitro-10-(carboxymethylene)-5H,10H-imidazo-[1,2-a] indeno[1,2-e]pyrazin-4-one may be prepared in the following way: to 450 ml of concentrated sulphuric acid cooled to 5° C. are gradually added 35.9 g of 10-(carboxymethylene)-5H,10H-imidazo[1,2-a]indeno[1,2-e]-pyrazin-4-one followed, after stirring for 30 minutes at 10° C., by 13 g of potassium nitrate in a single portion. The reaction is continued for 90 minutes at the same temperature. The reaction medium is run onto 1 liter of ice-water and the precipitate formed is filtered off, washed with water and dried. 35.5 g of expected product are thus obtained in the form of a yellow solid, the melting point of which is greater than 260° C.

EXAMPLE 37

To 2 g of 8-amino-10-acetamido-10-methyl-5H,10H-imidazo[1,2-a]indeno[1,2-e]pyrazin-4-one suspended in 15 ml of dimethylformamide, at a temperature in the region of 20° C., are added dropwise 1.8 ml of n-propyl isocyanate. After stirring for 30 minutes, the reaction medium becomes clear and an insoluble product forms after 2 hours of reaction. The reaction is continued for 15 hours at the same temperature. The precipitate formed is filtered off, then taken up in dimethyl sulphoxide and filtered off on a bed of silica. The solvent is evaporated off under reduced pressure and the brown crystallized solid is taken up in 20 ml of 6N hydrochloric acid and refluxed for 2 hours. After cooling to a temperature in the region of 20° C., the precipitate obtained is filtered off and washed with acetone to give 0.65 g of 10-amino-10-methyl-8-(3-n-propylureido)-5H,10H-imidazo[1,2-a]-indeno(1,2-e)pyrazin-4-one hydrochloride trihydrate in the form of a pale yellow powder decomposing without melting at about 220° C. (Analysis, $C_{18}H_{27}ClN_6O_5.0.78\ HCl$, % calculated C: 48.81; H: 6.14; Cl: 8.00; N: 18.97; % found C: 48.6; H: 6.1; Cl: 8.0; N: 19.2).

EXAMPLE 38

To 2 g of 10-acetamido-7-chloro-5H,10H-imidazo[1,2-a] indeno[1,2-e]pyrazin-4-one in 40 ml of anhydrous dimethyl sulphoxide, maintained at 20° C. under a nitrogen atmosphere, is added 0.61 g of 60% sodium hydride and the mixture is stirred for 90 minutes. 0.8 ml of benzyl chloride are then added dropwise and the stirring is continued for 24 hours. The reaction medium is then poured onto 50 ml of ice-water, then acidified using 1N hydrochloric acid (12 ml). The precipitate formed is filtered off, washed with water and then with acetone, and dried. The crude product thus obtained (1.8 g) is taken up in 20 ml of 6N hydrochloric acid and maintained at reflux for 2 hours. The insoluble product is filtered off, washed with water and recrystallized from 45 ml of a mixture of ethanol and water (½ by volume) to give 0.31 g of 10-amino-10-benzyl-7-chloro-5H,10H-imidazo-[1,2-a]indeno[1,2-e]pyrazin-4-one dihydrate in the form of a white powder melting at 241° C. (Analysis, $C_{20}H_{19}ClN_4O_3.0.82$ HCl, % calculated C: 60.23; H: 4.80; Cl: 8.89; N: 14.05; % found C: 60.2; H: 4.4; Cl: 8.9; N: 13.4).

10-Acetamido-7-chloro-5H,10H-imidazo[1,2-a]-indeno [1,2-e]pyrazin-4-one may be prepared in the following way: to 8.5 g of 10-hydroxyimino-7-chloro-5H-imidazo[1,2-a] indeno[1,2-e]pyrazin-4-one in 150 ml of acetic acid are gradually added 4.43 g of zinc powder. The reaction medium is then maintained at 90° C. for 1 hour. After cooling to a temperature in the region of 20° C., 3 ml of acetic anhydride are then added to the reaction medium and the reaction is continued for 72 hours at the same temperature. 200 ml of distilled water are then run into the medium and, after stirring for 2 hours at 20° C., the insoluble product is filtered off, washed with acetone and then with methanol, and dried under reduced pressure (1 mmHg; 0.13 kPa) at 45° C. 7.5 g of expected product are obtained in the form of a beige-coloured solid which is used without further purification in the subsequent syntheses.

7-Chloro-10-hydroxyimino-5H-imidazo[1,2-a]-indeno[1, 2-e]pyrazin-4-one may be obtained according to the following procedure: 0.97 g of 60% sodium hydride are added to a suspension of 2.5 g of 7-chloro-5H,10H-imidazo[1,2-a] indeno[1,2-e]pyrazin-4-one in 30 ml of anhydrous dimethyl sulphoxide. After stirring for 30 minutes at a temperature in the region of 20° C., a solution of 1.3 ml of isoamyl nitrite in 10 ml of dimethyl sulphoxide is added dropwise, and the mixture is then stirred for 3 hours at the same temperature. 20 ml of distilled water are added slowly and the mixture is then poured onto ice-water, acidified with acetic acid and centrifuged. After removal of the supernatant solution, the solid is taken up in 20 ml of acetone and the insoluble product is filtered off, washed with methanol and dried. The product obtained (1.3 g) is suspended in 30 ml of dimethyl sulphoxide and the insoluble product is filtered off, washed with water and dried. The filtrate is treated with 100 ml of water and the precipitate formed is filtered off, washed with water and dried. The two insoluble products thus isolated are combined, washed with water and dried under reduced pressure (1 mmHg; 0.13 kPa) at 50° C. 1.05 g of expected product are obtained in the form of a yellow powder, the melting point of which is greater than 260° C.

7-Chloro-5H,10H-imidazo[1,2-a]indeno[1,2-e]-pyrazin-4-one may be obtained according to the process described in Patent WO 94/07893.

EXAMPLE 39

10 g of 5H,10H-imidazo[1,2-a]indeno[1,2-e]-pyrazin-4-one and 27.1 g of 3-nitrobenzaldehyde are refluxed for 15 hours in the presence of 13.79 g of ammonium acetate in 600 ml of acetic acid. The precipitate formed is filtered off, washed with water and dried under reduced pressure (1 mmHg; 0.13 kPa) at 45° C. 10 g of 10-(3-nitrobenzylidene)-5H-imidazo-[1,2-a]indeno[1,2-e]pyrazin-4-one are obtained in the form of a yellowish powder, the melting point of which is greater than 260° C. (Analysis, $C_{20}H_{12}N_4O_3$; % calculated C: 67.42; H: 3.39; N: 15.57; O: 13.47; % found C: 67.4; H: 3.2; N: 15.6; O: 13.5).

EXAMPLE 40

3 g of 10-(3-nitrobenzylidene)-5H-imidazo-( 1,2-a] indeno[1,2-e]pyrazin-4-one are hydrogenated at atmospheric pressure and at 50° C. in the presence of 10% palladium-on-charcoal in 100 ml of dimethylformamide. After 20 hours of reaction, the reaction medium is filtered on Celite. The insoluble material is washed with 1 liter of dimethyl sulphoxide and the filtrate is concentrated to dryness under reduced pressure. After drying of the yellow powder thus obtained (5 mmHg; 0.65 kPa) at 65° C., 2.5 g of 10-(3-aminobenzyl)-5H,10H-imidazo[1,2-a]indeno[1,2-e]pyrazin-4-one are obtained, the melting point of which is greater than 260° C. (Analysis, $C_{20}H_{16}N_4O.0.52$ $H_2O.0.30$ DMSO; % calculated C: 73.16; H: 4.91; N: 17.06; % found C: 73.2; H: 5.1; N: 17.2).

EXAMPLE 41

To 0.5 g of 10-(3-nitrobenzylidene)-5H-imidazo[1,2-a] indeno[1,2-e]pyrazin-4-one suspended in 15 ml of absolute ethanol are added 1.57 g of tin chloride dihydrate. The reaction medium is refluxed for 6 hours and then left at a temperature in the region of 20° C. for 72 hours. The reaction medium is treated with 30 ml of saturated sodium carbonate solution and the insoluble material is filtered off, washed with water, dried and then taken up in 80 ml of dimethylformamide. The new insoluble material is filtered off and discarded. The filtrate is concentrated to dryness under reduced pressure and dried (5 mmHg; 0.65 kPa) at 55° C. 0.28 g of 10-(3-aminobenzylidene)-5H-imidazo-[1,2-a] indeno[1,2-e]pyrazin-4-one is thus obtained in the- form of an orange-coloured powder, the melting point of which is greater than 260° C. (Analysis, $C_{20}H_{14}N_4O.0.39$ $H_2O.0.48$ DMF; % calculated C: 73.61; H: 4.32; N: 17.17; % found C: 73.6; H: 3.9; N: 16.9).

EXAMPLE 42

A suspension of 1 g of 10-(3-aminobenzyl)-5H,10H-imidazo[1,2-a]indeno[1,2-e]pyrazin-4-one in 10 ml of acetic acid in the presence of 0.34 ml of acetic anhydride is heated at 80° C. for 2 hours. After cooling to a temperature in the region of 20° C., the reaction medium is filtered, washed with water and then with acetone, and dried to give 0.61 g of 10-(3-acetyl-aminobenzyl)-5H,10H-imidazo[1,2-a] indeno[1,2-e]pyrazin-4-one in the form of a yellow powder decomposing without melting at about 200° C. (Analysis, $C_{22}H_{18}N_4O_2.1.60$ $H_2O$; % calculated C: 71.33; H: 4.90; N: 15.13; % found C: 71.3; H: 4.7; N: 15.3).

EXAMPLE 43

0.5 g of 5H,10H-imidazo[1,2-a]indeno[1,2-e]-pyrazin-4-one and 1.47 g of 3-methoxycarbonyl-benzaldehyde are refluxed for 48 hours in the presence of 0.7 g of ammonium acetate in 30 ml of acetic anhydride. After cooling to a temperature in the region of 20° C., the precipitate formed is filtered off, washed with water and dried under reduced pressure (1 mmHg; 0.13 kPa) at 50° C. 0.53 g of 10-(3-methoxycarbonyl-benzylidene)-5H-imidazo[1,2-a]indeno [1,2-e]pyrazin-4-one acetate is obtained in the form of a yellow powder, the melting point of which is greater than 260° C. (Analysis, $C_{24}H_{19}N_3O_5.0.19$ $H_2O$; % calculated C: 67.13; H: 4.46; N: 9.79; O: 18.63; % found C: 66.9; H: 4.4; N: 9.9; O: 18.6).

EXAMPLE 44

To a suspension, maintained under nitrogen, of 1.8 g of (10 RS)-10-acetamido-5H,10H-imidazo[1,2-a]-indeno[1,2- e]pyrazin-4-one in 45 ml of dimethyl sulphoxide are added portionwise 960 mg of an 80% suspension of sodium hydride in oil. The mixture is stirred for 15 minutes at a temperature in the region of 20° C., followed by addition of a solution of 0.95 ml of (2-chloroethyl)benzene in 2 ml of dimethyl sulphoxide. After 15 hours at room temperature, a further 0.45 ml of (2-chloroethyl)benzene dissolved in 1 ml of dimethyl sulphoxide is added. The reaction medium is left for 6 hours at a temperature in the region of 20° C., and is then poured into a mixture of 150 g of ice, 260 ml of distilled water and 3.5 ml of acetic acid. 150 ml of ethyl acetate are added to the suspension obtained and the mixture is stirred, followed, after separation of the phases once settling has taken place, by removal of the ethyl acetate. The operation is repeated twice. The precipitate is filtered off on a sinter funnel. The solid is crystallized from 7 ml of dimethylformamide and is then recrystallized from 30 ml of methanol. 100 mg of (10 RS)-10-acetamido-10-phenethyl-5H,10H-imidazo[1,2-a]-indeno[1,2-e]pyrazin-4-one are thus obtained in the form of a grey solid melting above 260° C. (Analysis, % calculated C: 71.9, H: 5.2, N: 14.6, % found C: 71.9, H: 5.0, N: 14.6).

EXAMPLE 45

A suspension of 250 mg of (10 RS)-10-acetamido-10-phenethyl-5H,10H-imidazo[1,2-a]indeno-[1,2-e]pyrazin-4-one in 15 ml of 6N hydrochloric acid is refluxed for 3 hours. The reaction medium is filtered on a sinter funnel. The filtrate is evaporated and the solid residue obtained is crystallized from 2 ml of ethanol. After filtration and rinsing of the crystalline solid, 60 mg of (10 RS)-10-amino-10-phenethyl-5H,10H-imidazo[1,2-a]indeno[1,2-e]pyrazin-4-one are obtained in the form of a white solid melting above 260° C. [$^1$H NMR spectrum: (200 MHz, $(CD_3)_2SO$-$d_6$ with addition of a few drops of $CD_3COOD$-$d_4$, δ in ppm): from 1.90 to 2.30 (mt, 2H: $CH_2$); from 2.75 to 3.15 (mt, 2H: $ArCH_2$); from 6.70 to 7.10 (mt, 5H: H of the phenyl); from 7.50 to 7.70 (mt, 2H: H 7 and H 8); 7.68 and 8.67 (2 broad s, 1H each: H of the imidazole); 7.98 and 8.07 (2 broad d, J=8 Hz, 1H each: H 6 and H 9)].

EXAMPLE 46

The process is performed as in Example 44 but starting with 3 g of (10 RS)-10-acetamido-5H,10H-imidazo[1,2-a]indeno[1,2-e]pyrazin-4-one, 70 ml of dimethyl sulphoxide, 1.2 g of an 80% suspension of sodium hydride in oil and 2.6 ml of 1-bromo-3-phenylpropane. The reaction medium is poured into a mixture of 250 g of ice, 435 ml of distilled water and 6 ml of acetic acid. 200 ml of ethyl acetate are added to the suspension obtained and the mixture is stirred, followed, after separation of the phases once settling has taken place, by removal of the ethyl acetate. The operation is repeated once. The precipitate is filtered off on a sinter funnel. The solid is crystallized from 200 ml of methanol. 390 mg of (10 RS)-10-acetamido-10-(3-phenylpropyl)-5H,10H-imidazo[1,2-a]indeno[1,2-e)pyrazin-4-one are obtained in the form of a green solid melting above 260° C. (Analysis, % calculated C: 72.3, H: 5.6, N: 14.0; % found C: 72.2, H: 5.5, N: 14.2).

EXAMPLE 47

A suspension of 550 mg of (10 RS)-10-acetamido-10-(3-phenylpropyl)-5H,10H-imidazo[1,2-a]-indeno[1,2-e]pyrazin-4-one in 30 ml of 4N hydrochloric acid is refluxed for 2 hours. The reaction medium is cooled and filtered on a sinter funnel. The solid obtained is recrystallized from 40 ml of ethanol. 130 mg of (10 RS)-10-amino-10-(3-phenylpropyl)-5H,10H-imidazo[1,2-a]indeno[1,2-e]pyrazin-4-one hydrochloride are obtained in the form of a grey solid melting above 260° C. (Analysis, % calculated C: 67.3, H: 5.4, Cl: 9.0, N: 14.3, O: 4.1; % found C: 67.1, H: 5.3, Cl: 9.0, N: 14.1, O: 4.1).

EXAMPLE 48

The process is performed as in Example 44 but starting with 3 g of (10 RS)-10-acetamido-5H,10H-imidazo[1,2-a]indeno[1,2-e]pyrazin-4-one, 70 ml of dimethyl sulphoxide, 1.2 g of an 80% suspension of sodium hydride in oil and 2.7 g of 1-chloro-4-phenylbutane. The reaction medium is poured into a mixture of 250 g of ice, 435 ml of distilled water and 6 ml of acetic acid. 200 ml of ethyl acetate are added to the suspension obtained and the mixture is stirred, followed, after separation of the phases once settling has taken place, by removal of the ethyl acetate. The operation is repeated once. The precipitate is filtered off on a sinter funnel. The solid is crystallized from methanol. 80 mg of (10 RS)-10-acetamido-10-(4-phenylbutyl)-5H,10H-imidazo[1,2-a]indeno[1,2-e]pyrazin-4-one are thus obtained in the form of a green solid melting above 260° C. (Analysis, % calculated C: 72.8, H: 5.9, N: 13.6, O: 7.8, % found C: 72.8, H: 6.0, N: 14.1, O: 7.9).

EXAMPLE 49

A suspension of 200 mg of (10 RS)-10-acetamido-10-(4-phenylbutyl)-5H,10H-imidazo-[1,2-a]indeno[1,2-e]pyrazin-4-one in 15 ml of 6N hydrochloric acid is refluxed for 2 hours. The reaction medium is cooled and filtered on a sinter funnel. The solid obtained is crystallized from 5 ml of ethanol. 85 mg of (10RS)-10-amino-10-(4-phenylbutyl)-5H,10H-imidazo[1,2-a]indeno[1,2-e]pyrazin-4-one hydrochloride are thus obtained [$^1$H NMR spectrum: (300 MHz, $(CD_3)_2SO$-$d_6$; δ in ppm): 0.65 (mt, 2H: $CH_2$); 1.38 (mt, 2H: $CH_2$); 2.35 (mt, 2H: hetero-$CH_2$); from 2.50 to 2.80 (mt, 2H: $ArCH_2$); 6.95 (d, J=7.5 Hz, 2H: aromatic ortho H of the phenyl); from 7.00 to 7.20 (mt, 3H: aromatic meta and para H of the phenyl); 7.52 and 7.58 (2 t, J=8 Hz, 1H each: H 7 and H 8); 7.72 and 8.68 (2 broad s, 1H each: H of the imidazole); 7.92 and 8.02.(2 broad d, J=8 Hz), 1H each: H 6 and H 9); 9.48 (mult., 3H: $NH_2^+Cl^-$); 12.72 (broad s, 1H: NH 5)].

EXAMPLE 50

A solution of 0.52 g of ethyl 5-(10-methyl-4,5-dihydro-4-oxo-10H-imidazo[1,2-a]indeno[1,2-e]-pyrazin-10-yl)valerate in 3 ml of 1N sodium hydroxide is stirred overnight at a temperature in the region of 20° C. The mixture is then treated with 3 ml of 1N hydrochloric acid and the precipitate formed is filtered off. The solid obtained is washed with distilled water (2×10 ml) and with ethyl ether (3×10 ml), and dried at 60° C. under vacuum (1 mmHg; 0.13 kPa). 0.4 g of 5-(10-methyl-4,5-dihydro-4-oxo-10H-imidazo[1,2-a]indeno [1,2-e]pyrazin-10-yl)valeric acid is obtained in the form of an ochre solid melting above 260° C. (Analysis, % calculated C: 67.64, H: 5.68, N: 12.45, O: 14.23, % found C: 67.6, H: 5.8, N: 12.5).

Ethyl 5-(10-methyl-4,5-dihydro-4-oxo-10H-imidazo[1,2-a]indeno[1,2-e]pyrazin-10-yl)valerate may be prepared in the following way: 0.33 g of 80% sodium hydride is added portionwise, under a stream of argon, to a stirred solution of 0.48 g of 10-methyl-5H,10H-imidazo[1,2-a]indeno[1,2-e]pyrazin-4-one in 25 ml of dimethylformamide. The stirring is continued for 20 minutes, 0.3 ml of trimethylsilyl chloride is added and the mixture is left stirring for 15 minutes. 0.35 ml of ethyl 5-bromovalerate is then added in a single portion and the stirring is continued overnight. The reaction mixture is treated with 10 ml of water and 1 ml of acetic acid and concentrated on a rotary evaporator. The evaporation residue is triturated with 10 ml of distilled water and filtered. The solid obtained is washed with distilled water and then with petroleum ether (40°–65° C.), and dried at 60° C. under vacuum (1 mmHg; 0.13 kPa). 0.52 g of ethyl 5-(10-methyl-4,5-dihydro-4-oxo-10H-imidazo[1,2-a]indeno [1,2-e] pyrazin-10-yl)valerate is obtained in the form of an ochre solid (Rf=0.42, thin layer chromatography on silica gel, eluent: chloroform/methanol/28% aqueous ammonia (24/6/1 by volume); Rf of the starting material (10-methyl-5R,10H-imidazo[1,2-a]indeno[1,2-e]pyrazin-4-one=0.60).

10-Methyl-5H,10H-imidazo[1,2-a]indeno[1,2-e]-pyrazin-4-one may be prepared in the following way: A mixture of 1 g of 10-hydroxymethylene-5H,10H-imidazo-[1,2-a]indeno[1,2-e]pyrazin-4-one, 80 ml of dimethylformamide and 20 ml of methanol is hydrogenated at a temperature in the region of 20° C. and normal pressure for 4 hours, in the presence of 10% palladium-on-charcoal. After filtration of the catalyst under an inert atmosphere, the solvents are evaporated off and the beige-coloured solid obtained (1.25 g) is purified by chromatography on a column of silica (100 g) with a mixture of dichloromethane and methanol (95/5 by volume). After drying at 90° C., 0.35 g of 10-methyl-5H,10H-imidazo[1,2-a]indeno[1,2-e]pyrazin-4-one is obtained in the form of a cream-coloured solid melting above 260° C. (Analysis, % calculated C: 70.87, H: 4.67, N: 17.71, O: 6.74, % found C: 70.5, H: 4.4, N: 17.4).

EXAMPLE 51

0.66 g of 80% sodium hydride is added, under an argon atmosphere, to a stirred solution of 0.96 g of 10-methyl-5H,10H-imidazo[1,2-a]indeno[1,2-e]pyrazin-4-one in 50 ml of dimethylformamide. The stirring is continued for 15 minutes at a temperature in the region of 20° C., followed by addition of 0.56 ml of trimethylsilyl chloride and the mixture is left stirring for 30 minutes. 0.44 ml of 1-bromo-3-chloropropane is then added and the stirring is continued for 25 minutes. 7.2 ml of a 2.78N solution of dimethylamine in ethyl ether are then added and the final mixture is left to react for one week at a temperature in the region of 20° C. The reaction mixture is treated with 10 ml of water and 0.5 ml of acetic acid, then concentrated on a rotary evaporator. The evaporation residue is triturated with 60 ml of isopropanol and filtered. The filtrate is concentrated on a rotary evaporator and the crude product is first purified by chromatography on a column of silica (100 g), eluting under a pressure of 0.5 bar with a mixture of chloroform, methanol and 28% aqueous ammonia (48/6/1 by volume). The product obtained (0.7 g) is then purified by treatment with 0.07N hydrochloric acid (27 ml), washing of the aqueous phase with dichloromethane (2×20 ml), basifying of the aqueous phase using concentrated sodium hydrogen carbonate solution and extraction of the alkaline phase with dichloromethane (3×25 ml) and then with chloroform (50 ml). The organic phases are combined, dried over magnesium sulphate, filtered and evaporated on a rotary evaporator. The evaporation residue is triturated with 30 ml of isopropyl ether, filtered and the solid obtained is dried at 60° C. under vacuum (1 mmHg; 0.13 kPa). 0.28 g of 10-(3-dimethylaminopropyl)-10-methyl-5H,10H-imidazo[1,2-a]indeno[1,2-e]pyrazin-4-one is obtained in the form of a white solid melting at about 195° C. (Analysis, % calculated C: 70.78, H: 6.88, N: 17.38, O: 4.96, % found C: 70.5, H: 7.3, N: 16.8).

EXAMPLE 52

The process is performed as in Example 50 for the preparation of ethyl 5-(10-methyl-4,5-dihydro-4-oxo- 10H-imidazo[1,2-a]indeno[1,2-e]pyrazin-10-yl)-valerate but starting with 1.42 g of 10-methyl-5H,10H-imidazo[1,2-a]indeno[1,2-e]pyrazin-4-one, 75 ml of dimethylformamide, 1 g of sodium hydride, 0.84 ml of trimethylsilyl chloride and 0.76 ml of 4-bromo-butyronitrile. The product is first purified by crystallization from acetonitrile, then by heating of the crystals to reflux in an ethyl acetate/methanol mixture (9/1 by volume). After allowing to stand for 2 hours at a temperature in the region of 20° C., the suspension is filtered and the solid is washed with ethyl acetate and dried at 60° C. under vacuum (1 mmHg; 0.13 kPa). 0.83 g of 4-(10-methyl-4,5-dihydro-4-oxo-10H-imidazo[1,2-a]indeno[1,2-e]pyrazin-10-yl)-butyronitrile is obtained in the form of an off-white solid melting above 260° C. (Analysis, % calculated C: 71.04, H: 5.30, N: 18.41, O: 5.26, % found C: 70.7, H: 5.5, N: 18.6).

EXAMPLE 53

A mixture of 3 g of 4-(10-methyl-4,5-dihydro-4-oxo-10H-imidazo[1,2-a]indeno[1,2-e]pyrazin-10-yl)-butyronitrile, 8 ml of water and 43 ml of concentrated hydrochloric acid is heated at a temperature in the region of 80° C. for 44 hours. The reaction mixture is cooled to a temperature in the region of 20° C. and filtered. The solid is washed with distilled water and 0.1N sodium hydroxide (55 ml) is added. This mixture is stirred for 15 minutes and the aqueous phase is washed with dichloromethane (2×35 ml), 0.2 g of animal black is added and the mixture is filtered. The filtrate is acidified to pH 4 with acetic acid and, after stirring overnight at a temperature in the region of 20° C., the suspension is filtered. The solid obtained is washed with distilled water and then with isopropyl ether, and dried at 60° C. under vacuum (1 mmHg; 0.13 kPa). A portion (0.32 g) of the pale pink solid obtained is treated with 10 ml of 0.1N sodium hydroxide with the aid of ultrasound, then the solution is filtered and freeze-dried. 0.28 g of 4-(10-methyl-4,5-dihydro-4-oxo-10H-imidazo[1,2-a]indeno[1,2-e]pyrazin-10-yl)butyric acid is obtained in the form of the sodium salt, melting above 260° C. (Analysis, % calculated C: 62.61, H: 4.67, N: 12.17, Na: 6.66, O: 13.90, % found C: 62.8, H: 4.3, N: 12.2).

EXAMPLE 54

The process is performed as in Example 50 for the preparation of ethyl 5-(10-methyl-4,5-dihydro-4-oxo-10H-imidazo[1,2-a]indeno[1,2-e]pyrazin-10-yl)-valerate but starting with 0.48 g of 10-methyl-5H,10H-imidazo[1,2-a]indeno[1,2-e]pyrazin-4-one, 25 ml of dimethylformamide, 0.33 g of sodium hydride, 0.28 ml of trimethylsilyl chloride and 0.1 g of trioxane. 0.27 g of 10-hydroxymethyl-10-methyl-5H,10H-imidazo[1,2-a]indeno[1,2-e]pyrazin-4-one is obtained in the form of a pale yellow solid melting above 260° C. (Analysis, % calculated C: 67.41, H: 4.90, N: 15.72, O: 11.97, % found C: 67.4, H: 4.9, N: 15.7).

EXAMPLE 55

To a very fine suspension of 0.4 g of 4-(10-methyl-4,5-dihydro-4-oxo-10H-imidazo[1,2-a]indeno-[1,2-e]pyrazin-10-yl)butyric acid in 20 ml of chloroform is added, at a temperature in the region of 20° C., 0.13 g of oxalyl chloride followed by a solution of 0.5 ml of dimethylformamide in 5 ml of chloroform, and the stirring is continued for 3 hours.

2 ml of a 5.6N solution of ammonia in methanol are then added and the stirring is continued for 18 hours. The reaction mixture is concentrated on a rotary evaporator and the evaporation residue is stirred for 2 hours with 30 ml of distilled water. The solid is filtered off and purified by chromatography on a column of silica (25 g), eluting under a pressure of 0.5 bar with a mixture of dichloromethane and methanol (9/1 by volume). 0.045 g of 4-(10-methyl-4,5-dihydro-4-oxo-10H-imidazo[1,2-a]indeno[1,2-e]pyrazin-10-yl)butyramide is obtained in the form of a light-beige-coloured solid melting above 260° C. ($^1$H NMR spectrum: (300 MHz; $(CD_3)_2SO-d_6$; δ in ppm): 0.65 (mt, 2H: $CH_2$); 1.53 (s, 3H: $CH_3$); 1.80 (t, J=7.5 Hz, 2H: $CH_2CON$); 2.10 and 2.28 (2 mts, 1H each: hetero-$CH_2$); 6.58 and 7.10 (2 broad s, 1H each: $CONH_2$); 7.27 and 7.33 (2 t, J=7.5 Hz, 1H each: H 7 and H 8); 7.42 and 7.92 (2 broad s, 1H each: H of the imidazole); 7.50 and 7.68 (2 broad d, J=7.5 Hz, 1H each: H 6 and H 8)).

EXAMPLE 56

The process is performed as in Example 53 but starting with 0.84 g of (10-methyl-4,5-dihydro-4-oxo-10H-imidazo[1,2-a]indeno[1,2-e]pyrazin-10-yl)-acetonitrile, 7.6 ml of concentrated hydrochloric acid and 1.5 ml of distilled water. The reaction mixture is cooled to a temperature in the region of 20° C., basified with 7 ml of concentrated sodium hydroxide and filtered. Distilled water (qs 50 ml) is added and the filtrate is acidified to pH 4 with acetic acid. The precipitate formed is filtered off, washed with distilled water and then with ethyl ether (2×15 ml), and dried at 60° C. under vacuum (1 mmHg; 0.13 kPa). 0.14 g of (10-methyl-4,5-dihydro-4-oxo-10H-imidazo-[1,2-a]indeno[1,2-e]pyrazin-10-yl)acetic acid is obtained in the form of a beige-coloured solid ($^1$H NMR spectrum: (200 MHz; $(CD_3)_2SO-d_6$; δ in ppm): 1.62 (s, 3H: $CH_3$); 3.22 (limiting AB, J=15.5 Hz, 1H: $CH_2COO$); 7.35 (mt, 2H: H 7 and H 8); 7.60 and 8.28 (2 broad s, 1H each: H of the imidazole); 7.65 and 7.85 (2 broad d, J=7.5 Hz, 1H each: H 6 and H 8); from 11.80 to 12.80 (broad mult., 1H: NH 5)).

(10-Methyl-4,5-dihydro-4-oxo-10H-imidazo [1,2-a]indeno[1,2-e]pyrazin-10-yl)acetonitrile may be prepared in the following way: the process is performed as in Example 51 for the preparation of ethyl 5-(10-methyl-4,5-dihydro-4-oxo-10H-imidazo[1,2-a]indeno-[1,2-e]pyrazin-10-yl)valerate but starting with 4.74 g of 10-methyl-5H,10H-imidazo[1,2-a]indeno-[1,2-e]-pyrazin-4-one, 250 ml of dimethylformamide, 3.3 g of sodium hydride, 2.78 ml of trimethylsilyl chloride and 1.55 ml of bromoacetonitrile. The product obtained (5.3 g) is purified by chromatography on a column of silica (525 g), eluting under pressure with a mixture of dichloromethane and methanol (19/1 by volume). 0.8 g of (10-methyl-4,5-dihydro-4-oxo-10H-imidazo[1,2-a]-indeno[1,2-e]pyrazin-10-yl)acetonitrile is obtained in the form of a beige-coloured solid which is used without further purification in the subsequent syntheses (Rf=0.46, thin layer chromatography on silica gel, eluent: chloroform/methanol/28% aqueous ammonia (24/6/1 by volume).

EXAMPLE 57

The process is performed as in Example 50 for the preparation of ethyl 5-(10-methyl-4,5-dihydro-4-oxo-10H-imidazo[1,2-a]indeno[1,2-e]pyrazin-10-yl)-valerate but starting with 3.56 g of 10-methyl-5H,10H-imidazo[1,2-a]indeno[1,2-e]pyrazin-4-one, 200 ml of dimethylformamide, 2.5 g of sodium hydride, 2.1 ml of trimethylsilyl chloride and 1.4 ml of 3-bromo-propionitrile. A portion (2.77 g) of the product obtained is purified by chromatography on a column of silica (140 g), eluting under a pressure of 0.5 bar with a mixture of dichloromethane and methanol (9/1 by volume). 0.7 g of 3-(10-methyl-4,5-dihydro-4-oxo-10H-imidazo[1,2-a]indeno[1,2-e]pyrazin-10-yl)propionitrile is obtained in the form of a solid melting at about 240° C. (Analysis, % calculated C: 70.33, H: 4.86, N: 19.30, O: 5.51, % found C: 70.3, H 5.3, N: 19.7).

EXAMPLE 58

The process is performed as in Example 53 but starting with 0.5 g of (10-methyl-4,5-dihydro-4-oxo-10H-imidazo[1,2-a]indeno[1,2-e]pyrazin-10-yl)-propionitrile, 7.6 ml of concentrated hydrochloric acid and 1.5 ml of distilled water. The reaction mixture is cooled to a temperature in the region of 20° C., 40 ml of distilled water are added and the mixture is basified with concentrated sodium hydroxide. The brown solution obtained is filtered and acidified to pH=4 with acetic acid. The precipitate formed is filtered off, washed with distilled water (20 ml) and then with isopropyl ether (2×20 ml), and dried at 60° C. under vacuum (1 mmHg; 0.13 kPa). 12.9 ml of 0.1N sodium hydroxide and distilled water (qs 40 ml) are added to the solid obtained (0.4 g) which is then filtered and freeze-dried. 0.36 g of 3-(10-methyl-4,5-dihydro-4-oxo-10H-imidazo[1,2-a]indeno[1,2-e]pyrazin-10-yl)propionic acid is obtained in the form of the sodium salt, melting above 260° C. (Analysis, % calculated C: 61.63, H: 4.26, N: 12.68, Na: 6.94, O: 14.49, % found C: 61.4, H: 3.8, N: 12.5).

EXAMPLE 59

A stirred suspension of 0.6 g of (10-methyl-4,5-dihydro-4-oxo-10H-imidazo[1,2-a]indeno[1,2-e]-pyrazin- 10-yl) butyric acid in 20 ml of dioxane is cooled to a temperature in the region of 10° C., under an argon atmosphere, and 0.19 ml of oxalyl chloride is added. A solution of 0.5 ml of dimethylformamide in 5 ml of dioxane is then added dropwise. After the addition, the mixture is left stirring for 4 hours at a temperature in the region of 20° C. A further 0.38 ml of oxalyl chloride and 6 ml of dimethylformamide are added dropwise and stirring is continued for 1 hour. A solution of 0.38 g of sodium tetraborohydride in 10 ml of dimethylformamide is then added dropwise and the stirring is continued overnight. The reaction mixture is treated with 10 ml of methanol, acidified to pH 1 with 1N hydrochloric acid and concentrated on a rotary evaporator. The evaporation residue is purified by chromatography on a column of silica (100 g) eluting, under a pressure of 0.5 bar, first with a dichloromethane/methanol mixture (95/5 by volume) and then with a dichloromethane/methanol/28% aqueous ammonia mixture (90/10/0.5 by volume). 70 mg of 10-(4-hydroxybutyl)-10-methyl-5H,10H-imidazo[1,2-a]indeno-[1,2-e]pyrazin-4-one are obtained in the form of a white solid ($^1$H NMR spectrum [300 MHz; $(CD_3)_2SO-d_6$; δ in ppm]: 0.52 (mt, 2H: $CH_2$); 1.29 (quintet, J=7.5 Hz, 2H: $CH_2$); 1.57 (s, 3H: $CH_3$); 2.17 and 2.36 (2 mts, 1H each: hetero-$CH_2$); 3.14 (t, J=7.5 Hz, 1H: $CH_2O$); 4.19 (broad s, 1H: OH); 7.38 (mt, 2H: H 7 and H 8); 7.67 and 8.24 (2 broad s, 1H each: H of the imidazole); 7.60 and 7.87 (2 broad d, J=7.5 Hz, 1H each: H 6 and H9)).

EXAMPLE 60

0.4 g of 80% sodium hydride is added over 5 minutes to a stirred solution, under an argon atmosphere, of 0.6 g of 10-methyl-5H,10H-imidazo-[1,2-a]indeno[1,2-e]pyrazin-4-one in 30 ml of dimethylformamide. The stirring is continued for 10 minutes at a temperature in the region of 20° C., then 0.35 ml of trimethylchlorosilane is added and the stirring is continued for 10 minutes. 82 mg of sodium hydride are then added and the stirring is continued for 1 hour. 0.5 g of 2-chloromethyl-1-methylimidazole hydrochloride is then added and the stirring is continued for 2 hours. The reaction mixture is treated with 6 ml of acetic acid and 200 ml of water. The solution obtained is washed with ethyl acetate (2×200 ml) and the aqueous phase is concentrated on a rotary evaporator. The evaporation residue is triturated with 20 ml of isopropanol and filtered, and the filtrate is concentrated on a rotary evaporator. A pasty residue is obtained which is purified by chromatography on a column of silica (80 g), eluting with a dichloromethane/methanol mixture (85/15 by volume). 0.28 g of 10-methyl-10-[(l-methylimidazol-2-yl)methyl]-5H,10H-imidazo[1,2-a]indeno[1,2-e]pyrazin-4-one is obtained in the form of a cream-coloured solid melting above 260° C. (Analysis, % calculated C: 68.87, H: 5.17, N: 21.13, O: 4.83, % found C: 68.8, H: 5.2, N: 21.2).

2-Chloromethyl-1-methylimidazole hydrochloride may be prepared in the following way: to 2 g of 2-hydroxymethyl-1-methylimidazole are added 10 ml of thionyl chloride and the mixture is heated at a temperature in the region of 80° C. for 2 hours. The reaction mixture is concentrated on a rotary evaporator and the pasty residue is triturated with 50 ml of ethyl ether. The solid obtained is filtered rapidly and dried under vacuum (15 mmHg; 2 kPa) in the presence of potassium hydroxide. 2.3 g of 2-chloromethyl-1-methylimidazole hydrochloride are obtained in the form of a light yellow solid which is used as it is in the subsequent syntheses.

2-Hydroxymethyl-1-methylimidazole may be prepared according to the process described by P. Fournari et al., Bull. Soc. Chim. Fr., (6), 2438 (1968).

EXAMPLE 61

To a stirred suspension of 4 g of 5H,10H-imidazo[1,2-a]indeno[1,2-e]pyrazin-4-one and 2 g of 1-methyl-5-imidazolecarboxaldehyde in 40 ml of dimethyl sulphoxide, under an inert atmosphere, are added portionwise 1.35 g of 80% sodium hydride while maintaining the temperature of the reaction medium in the region of 20° C. The stirring is continued for 3 hours and the reaction mixture is treated with 40 ml of water and 6 ml of acetic acid. The precipitate formed is filtered off, washed with methanol and air-dried. A portion (2 g) of the red solid obtained is placed in fine suspension in 50 ml of methanol, and 2.5 ml of 4.5N hydrochloric acid in ethyl ether are added. The hydrochloride obtained is filtered off, washed with methanol and dried at 30° C. under vacuum (1 mmHg; 0.13 kPa). 1.3 g of 10-[(1-methylimidazol-5-yl)methylene]-5H,10H-imidazo[1,2-a]indeno[1,2-e]-pyrazin-4-one hydrochloride is obtained in the form of an orange-yellow-coloured solid melting above 260° C. (Analysis, % calculated C: 55.68, H: 3.89, Cl: 18.26, N: 18.04, O: 4.12, % found C: 55.7, H: 3.6, N: 18.0).

1-Methyl-5-imidazolecarboxaldehyde may be prepared according to the process described by R. Kirchlechner et al., Synthesis, 247, (1994).

EXAMPLE 62

A mixture of 3.2 g of 10-[(1-methylimidazol-5-yl)methylene]-5H,10H-imidazo[1,2-a]indeno[1,2-e]-pyrazin-4-one, 60 ml of 1N hydrochloric acid and 30 ml of water is hydrogenated, at a temperature in the region of 20° C. and at a pressure of 1.7 bar of hydrogen, for 6 hours in the presence of 10% palladium-on-charcoal. The catalyst is removed by filtration under an inert atmosphere and the filtrate is brought to pH=6 with concentrated sodium hydroxide. The white precipitate formed is filtered off, washed with distilled water and dried at 35° C. under vacuum (1 mmHg; 0.13 kPa). 2.1 g of 10-[(1-methylimidazol-5-yl)methyl]-5H,10H-imidazo[1,2-a] indeno[1,2-e]pyrazin-4-one are obtained in the form of a white solid melting above 260° C. (Analysis, % calculated C: 68.13, H: 4.76, N: 22.07, O: 5.04, % found C: 67.8, H: 4.9, N: 22.5).

EXAMPLE 63

The process is performed as in Example 62 but starting with 0.3 g of 8-[3-(3-fluorophenyl)ureido]-10-(carboxymethylene)-5H,10H-imidazo[1,2-a]indeno-[1,2-e]pyrazin-4-one hydrochloride, 15 ml of water and 1 ml of 1N sodium hydroxide. After removal of the catalyst, the filtrate is acidified with 2 ml of 1N hydrochloric acid and the precipitate formed is filtered off, washed with distilled water and dried under vacuum (1 mnHg; 0.13 kPa). 0.14 g of 8-[3-(3-fluorophenyl)ureido]-10-(carboxymethyl)-5H,10H-imidazo[1,2-a)indeno[1,2-e]pyrazin-4-one hydrochloride is obtained in the form of a light brown solid melting above 260° C. ($^1$H NMR spectrum (300 MHz; $(CD_3)_2SO-d_6$; δ in ppm]: 2.60 and 3.27 (2 dd, J=16.5 and 9 Hz and J=16.5 and 3.5 Hz respectively, 1H each: $CH_2$); 4.47 (dd, J=9 Hz and 3.5 Hz, 1H: CH 10); 6.80 (dt, J=8.5 and 2 Hz, 1H: aromatic H ortho to the F and para to the ureido); 7.13 (broad d, J=8.5 Hz, 1H: aromatic H para to the F and ortho to the ureido); 7.32 (dt, J=8.5 and 8 Hz, 1H: aromatic H meta to the F and meta to the ureido); 7.44 (dd, J=8.5 and 1.5 Hz, 1H: H 7); 7.53 (d mt, J=12 Hz, 1H: aromatic H ortho to the F and ortho to the ureido); 7.75 and 8.26 (2 broad s, 1H each: H of the imidazole); 7.79 (d, J=8.5 Hz, 1H: H 6), 7.87 (broad s, 1H: H 9); 9.18 and 9.23 (2 broad s, 1H each: NHCONH); 12.65 (s 1H: NH 5)).

8-[3-(3-Fluorophenyl)ureido]-10-(carboxymethylene)-5H,10H-imidazo[1,2-a]indeno-[1,2-e]pyrazin-4-one hydrochloride may be prepared in the following way: to a stirred suspension of 0.6 g of 8-amino-10-(carboxymethylene)-5H, 10H-imidazo[1,2-a]-indeno[1,2-e]pyrazin-4-one hydrochloride and 0.66 g of potassium carbonate in 10 ml of dimethylformamide is added 0.55 ml of 3-fluorophenyl isocyanate and the stirring is continued for 48 hours. 25 ml of ethyl ether are added to the reaction mixture and the precipitate formed is filtered off, triturated with 10 ml of distilled water and filtered off. The red-brown solid obtained is placed in fine suspension in 10 ml of distilled water, 1 ml of 1N hydrochloric acid is added and the product is filtered off, washed with distilled water and dried under vacuum (1 mmHg; 0.13 kPa). 0.3 g of 8-[3-(3-fluorophenyl)ureido]-10-(carboxymethylene)-5H,10H-imidazo[1,2-a]indeno[1,2-e]-pyrazin-4-one hydrochloride is obtained in the form of a light brown solid melting above 260° C., which product is used as it is in the subsequent syntheses.

8-Amino-10-(carboxymethylene)-5H,10H-imidazo-[1,2-a]indeno[1,2-e]pyrazin-4-one hydrochloride may be prepared in the following way: to a stirred mixture of 15.3 ml of concentrated hydrochloric acid and 2.08 g of stannous chloride dihydrate is added 1 g of 8-nitro-10-(carboxymethylene)-5H,10H-imidazo[1,2-a]indeno[1,2-e]-pyrazin-4-one and the mixture is heated at a temperature in the region of 45° C. for 4 hours. The reaction mixture is cooled to about 20° C. and filtered. The solid obtained is washed with distilled water and dried at 40° C. under vacuum (1 mmHg; 0.13 kPa). 0.69 g of 8-amino-10-(carboxymethylene)-5H,10H-imidazo[1,2-a]-indeno[1,2-e]pyrazin-4-one hydrochloride is obtained in the form of a yellow solid melting above 260° C., which product is used as it is in the subsequent syntheses.

8-Nitro-10-(carboxymethylene)-5H,10H-imidazo-[1,2-a]indeno[1,2-e]pyrazin-4-one may be prepared in the following way: a solution of 23.2 g of 10-(carboxymethylene)-5H,10H-imidazo[1,2-a]indeno-[1,2-e]pyrazin-4-one in 280 ml of concentrated sulphuric acid is stirred at a temperature in the region of 2° C., and 8.38 g of potassium nitrate are added portionwise over 15 minutes, while maintaining the temperature below 5C. The temperature of the reaction medium is allowed to return to about 20° C. and the stirring is continued for 4 hours. The reaction mixture is poured onto 1 liter of water and ice. The precipitate formed is filtered off, washed with distilled water and then with acetone, and dried at 60° C. under vacuum (5 mmHg). 24.5 g of 8-nitro-10-(carboxymethylene)- 5H,10H-imidazo[1,2-a]indeno[1,2-e)-pyrazin-4-one are obtained in the form of an orange-coloured solid melting above 260° C., which product is used as it is in the subsequent syntheses.

EXAMPLE 64

A mixture of 0.75 g of methyl [8-(3-methylureido)-4,5-dihydro-4-oxo-10H-imidazo[1,2-a]-indeno[1,2-e]pyrazin-10-yl]acetate and 4 ml of 1N sodium hydroxide is heated at a temperature in the region of 35° C. for 2 hours. The mixture is acidified with 1N hydrochloric acid and the precipitate formed is filtered off, washed with distilled water and dried at 60° C. under vacuum (1 mmHg; 0.13 kPa). 0.33 g of [8-(3-methylureido)-4,5-dihydro-4-oxo-10H-imidazo[1,2-a]-indeno[1,2-e]pyrazin-10-yl]acetic acid is obtained in the form of a yellow solid melting above 260° C. (Analysis, % calculated C: 57.79, H: 4.28, N: 19.82, O: 18.11, % found C: 57.8, H: 4.3, N: 19.8).

Methyl [8-(3-methylureido)-4,5-dihydro-4-oxo-10H-imidazo[1,2-a]indeno[1,2-e]pyrazin-10-yl]acetate may be prepared in the following way: to a stirred suspension of 7.72 g of methyl (8-amino-4,5-dihydro-4-oxo-10H-imidazo[1,2-a]indeno[1,2-e]pyrazin-10-yl)acetate and 2.76 g of potassium carbonate in 90 ml of dimethylformamide is added dropwise a solution of 1.95 ml of methyl isocyanate in 6 ml of dimethylformamide and the stirring is continued for 6 hours at a temperature in the region of 20° C. The reaction mixture is filtered and the filtrate is concentrated on a rotary evaporator. The evaporation residue is stirred for 48 hours in the presence of 200 ml of ethyl acetate and is filtered. The brown residue obtained is purified by chromatography on a column of silica (200 g), eluting with a chloroform/methanol/28% aqueous ammonia mixture (24/6/1 by volume). 0.3 g of methyl [8-(3-methylureido)-4,5-dihydro-4-oxo-10H-imidazo[1,2-a]indeno[1,2-e]pyrazin-10-yl]acetate is obtained in the form of an off-white solid melting above 260° C. (Rf=0.33, thin layer chromatography on silica gel, eluent: chloroform/methanol/28% aqueous ammonia (24/6/1 by volume).

Methyl 8-amino-4,5-dihydro-4-oxo-10H-imidazo[1,2-a]indeno[1,2-e]pyrazin-10-yl)acetate may be prepared in the following way: to a stirred suspension of 14 g of 8-nitro-10-(carboxymethylene)-5H,10H-imidazo[1,2-a]indeno[1,2-e]pyrazin-4-one in 230 ml of methanol, under an argon atmosphere, are added 185 ml of concentrated hydrochloric acid followed by 7.75 g of iron powder, and the stirring is continued for 2 hours at a temperature in the region of 20° C. A further 7.75 g of iron powder are added and the mixture is heated at a temperature in the region of 65° C. for 6 hours. The reaction mixture is filtered and the solid obtained is washed with methanol (2×100 ml) and dried under vacuum (1 mmHg; 0.13 kPa). 11.2 g of methyl 8-amino-4,5-dihydro-4-oxo-10H-imidazo[1,2-a]indeno-[1,2-e]pyrazin-10-yl)acetate is obtained in the form of a yellow solid melting above 260° C. (Rf=0.47, thin layer chromatography on silica gel, eluent: chloroform/methanol/28% aqueous ammonia (24/6/1 by volume).

EXAMPLE 65

A mixture of 1.4 g of enantiomer A which is methyl [8-(3-methylureido)-4,5-dihydro-4-oxo-10H-imidazo[1,2-a]indeno[1,2-e]pyrazin-10-yl]acetate, 13 ml of 8N hydrochloric acid and 65 ml of dioxane is heated at a temperature in the region of 40° C. for 33 hours. The reaction mixture is filtered and the solid is washed with ethyl ether and dried under vacuum (1 mmHg; 0.13 kPa). 0.9 g of (+)-[8-(3-methylureido)-4,5-dihydro-4-oxo-10H-imidazo[1,2-a]indeno[1,2-e]pyrazin-10-yl)acetic acid hydrochloride is obtained in the form of a yellow solid melting above 260° C. (Analysis, % calculated C: 52.38, H: 4.14, Cl: 9.10, N: 17.97, O: 16.42, % found C: 52.4, H: 3.7, N: 17.8; $[\alpha]^{20}_D$= +94.2°).

Enantiomer A, methyl [8-(3-methylureido)-4,5-dihydro-4-oxo-10H-imidazo[1,2-a]indeno[1,2-e]pyrazin-10-yl]acetate, may be prepared by chromatography under pressure of the racemic mixture on a column containing a stationary phase consisting of silica coated with cellulose tris(3,5-dimethylphenyl carbamate), eluting with a heptane/ethanol mixture (30/70 by volume) containing 0.1% of trifluoroacetic acid. Starting with 14×0.5 g of methyl (±)-[8-(3-methylureido)-4-oxo-5H,10H-imidazo[1,2-a]indeno[1,2-e]pyrazin-10-yl]acetate, 1.8 g of enantiomer A, which is methyl [8-(3-methylureido)-4,5-dihydro-4-oxo-10H-imidazo-[1,2-a]indeno[1,2-e]pyrazin-10-yl]acetate, and 1.9 g of enantiomer B, which is methyl [8-(3-methylureido)-4,5-dihydro-4-oxo-10H-imidazo[1,2-a]indeno[1,2-e]pyrazin-10-yl]acetate, are obtained. Enantiomers A and B were used without further purification in the subsequent syntheses.

EXAMPLE 66

The process is performed as in Example 65 but starting with 1.8 g of enantiomer B, methyl [8-(3-methylureido)-4,5-dihydro-4-oxo-10H-imidazo[1,2-a]indeno[1,2-e]pyrazin-10-yl]acetate. 1.1 g of (−)-[8-(3-methylureido)-4,5-dihydro-4-oxo-10H-imidazo[1,2-a]indeno[1,2-e]pyrazin-10-yl]acetic acid hydrochloride are obtained in the form of a yellow solid melting above 260° C. (Analysis, % calculated C: 52.38, H: 4.14, Cl: 9.10, N: 17.97, O: 16.42, % found C: 52.5, H: 4.1, N: 17.8, $[\alpha]^{20}_D$=−83.8°).

EXAMPLE 67

To a stirred mixture of 6.7 g of 5H,10H-imidazo[1,2-a]indeno[1,2-e]pyrazin-4-one, 140 ml of dimethyl sulphoxide and 4.15 g of glyoxylic acid monohydrate, under an argon atmosphere, are added portionwise 4.95 g of 80% sodium hydride while maintaining the temperature at about 20° C. The stirring is continued for 18 hours, and the reaction medium is acidified using acetic acid (11 ml) and is heated at a temperature in the region of 80° C. for 2 hours. The reaction mixture is filtered and the solid is washed with acetone (3×75 ml), with methanol (75 ml), again with acetone (2×75 ml) and dried under vacuum (1 mmHg; 0.13 kPa). The light-beige-coloured solid obtained (10.1 g) is dissolved in 500 ml of distilled water and the aqueous solution is washed with ethyl acetate (2×100 ml), then treated with 0.5 g of animal black and filtered. The filtrate is acidified with 45 ml of 1N hydrochloric acid and the precipitate formed is filtered off, washed with distilled water (50 ml) and with acetone (3×75 ml), and dried at 70° C. under vacuum (1 mmHg; 0.13 kPa). 5.7 g of (4,5-dihydro-4-oxo-10H-imidazo(1,2-a]indeno[1,2-e]pyrazin-10-yl) glycolic acid are obtained in the form of a pale yellow solid melting above 260° C. ($^1$H NMR spectrum (200 MHz, $(CD_3)_2SO$-$d_6$, δ in ppm): 4.60 (d, J=3 Hz, 1H: H 10); 5.09 (d, J=3 Hz, 1H: CHO); 5.60 (broad mult., 1H: OH); from 7.25 to 7.50 (mt, 2H: H 7 and H 8); 7.45 and 7.85 (2 broad d, J=7.5 Hz, 1H each: H 6 and H 8); 7.57 and 8.23 (2 broad s, 1H each: H of the imidazole); 12.35 (broad s, 1H: NH 5)).

EXAMPLE 68

To a solution of 1.3 g of 10-amino-10-methyl-5H,10H-imidazo[1,2-a]indeno[1,2-e]pyrazin-4-one in 25 ml of acetic acid is added 0.66 g of 2,5-dimethoxytetrahydrofuran. The mixture is stirred at boiling for 1 hour, cooled to 20° C. and concentrated to dryness under reduced pressure (15 mmHg; 2 kPa) at 60° C. The product obtained is suspended in 100 ml of distilled water and the insoluble product formed is isolated by filtration, washed successively 4 times with 40 ml in total of distilled water, 3 times with 30 ml in total of methanol and 3 times with 30 ml in total of acetone, and then dried under reduced pressure (1 mmHg; 0.13 kPa) at 100° C. 0.82 g of 10-methyl-10-(1-pyrrolyl)-5H,10H-imidazo[1,2-a]indeno[1,2-e]pyrazin-4-one is thus obtained, melting at 320° C. (decomposition) (Analysis, % calculated C: 71.51, H: 4.67, N: 18.53, O: 5.29, % found C: 71.7, H: 4.5, N: 18.3).

EXAMPLE 69

To a solution of 0.86 g of 10-amino-10-methyl-5H,10H-imidazo[1,2-a]indeno[1,2-e]pyrazin-4-one in 75 ml of acetic acid is added 0.6 g of phthalic anhydride and the mixture is stirred for 15 hours at a temperature in the region of 20° C. The insoluble product formed is isolated by filtration, washed with 5 ml of acetic acid, with distilled water until neutral and 3 times with 15 ml in total of acetone, and then dried under reduced pressure (1 mmHg; 0.13 kPa) at 60° C. 1.06 g of 2-[10-(10-methyl-4-oxo-4,5-dihydro-10H-imidazo[1,2-a]indeno[1,2-e]pyrazinyl)aminocarbonyl]-benzoic acid are thus obtained, decomposing without melting above 250° C. (Analysis, % calculated C: 66.00, H: 4.03, N: 13.99, O: 15.98, % found C: 66.0, H: 3.9, N: 13.8, O: 15.8).

EXAMPLE 70

To a solution of 0.86 g of 1-amino-10-methyl-5H,$_{10}$H-imidazo[1,2-a]indeno[1,2-e]pyrazin-4-one in 75 ml of acetic acid is added 0.54 g of 2,2-dimethylsuccinic anhydride and the mixture is stirred for 20 hours at a temperature in the region of 20° C. and then for 8 hours at 80° C. After cooling to a temperature in the region of 20° C., the insoluble product formed is isolated by filtration, washed twice with 10 ml in total of acetic acid and 3 times with 30 ml in total of acetone, and then dried under reduced pressure (1 mmHg; 0.13 kPa) at 80° C. 0.46 g of 3-[10-(10-methyl-4-oxo-4,5-dihydro-10H-imidazo[1,2-a]indeno-[1,2-e]pyrazinyl) aminocarbonyl]-2,2-dimethylpropionic acid is thus obtained, decomposing without melting above 250° C. (Analysis, % calculated C: 63.15, H: 5.30, N: 14.73, O: 16.82, % found C: 63.2, H: 4.5, N: 14.8, O: 17.4).

EXAMPLE 71

To a solution of 0.86 g of 10-amino-10-methyl-5H,10H-imidazo[1,2-a]indeno[1,2-e]pyrazin-4-one in 75 ml of acetic acid is added 0.59 g of 3,3-dimethylglutaric anhydride and the mixture is stirred for 16 hours at 80° C. After cooling to a temperature in the region of 20° C. and concentrating to dryness under reduced pressure (15 mmHg; 2 kPa), the product obtained is suspended in 50 ml of acetone. The insoluble product formed is isolated by filtration, washed 3 times with 15 ml in total of acetone and then dried under reduced pressure (1 mmHg; 0.13 kPa) at 60° C. 1 g of 4-[10-(10-methyl-4-oxo-4,5-dihydro-10H-imidazo[1,2-a]indeno-[1,2-e]pyrazinyl)aminocarbonyl]-3,3-dimethylbutyric acid is thus obtained, melting at 250° C. (decomposition) (Analysis, % calculated C: 63.95, H: 5.62, N: 14.20, O: 16.23, % found C: 63.9, H: 5.9, N: 14.4).

EXAMPLE 72

To a solution of 0.86 g of 10-amino-10-methyl-5H,10H-imidazo[1,2-a]indeno[1,2-e]pyrazin-4-one in 75 ml of acetic acid is added 0.59 g of 2,2-dimethylglutaric anhydride and the mixture is stirred for 16 hours at 80° C. After cooling to a temperature in the region of 20° C. and concentrating to dryness under reduced pressure (15 mmHg; 2 kPa), the product obtained is suspended in 80 ml of acetone. The insoluble product formed is isolated by filtration, washed 4 times with 20 ml in total of acetone and then air-dried. The product obtained (1 g) is dissolved at 50° C. in 30 ml of saturated aqueous sodium hydrogen carbonate solution and the solution, cooled to a temperature in the region of 20° C., is filtered and then acidified with acetic acid. The insoluble product formed is isolated by filtration, washed 4 times with 20 ml in total of distilled water and dried under reduced pressure (1 mmHg; 0.13 kPa) at 60° C. 0.8 g of 4-[10-(10-methyl-4-oxo-4,5-dihydro-10H-imidazo[1,2-a]indeno-[1,2-e]pyrazinyl)aminocarbonyl]-2,2-dimethylbutyric acid is thus obtained, decomposing without melting above 250° C. (Analysis, % calculated C: 63.95, H: 5.62, N: 14.20, O: 16.23, % found C: 63.9, H: 5.5, N: 14.4).

EXAMPLE 73

A suspension of 0.8 g of methyl 1-[10-(4-oxo-4,5-dihydro-10H-imidazo[1,2-a]indeno[1,2-e]pyrazinyl)]-pyrrole-2-carboxylate in a mixture of 4.4 ml of 1-propanol and 0.26 ml of aqueous 30% sodium hydroxide solution is stirred at boiling for 2 hours. After cooling to a temperature in the region of 20° C., addition of 20 ml of distilled water and acidification with 2N hydrochloric acid, the insoluble product formed is isolated by filtration, washed 4 times with 20 ml in total of distilled water and air-dried at a temperature in the region of 20° C. 0.8 g of 1-[10-(4-oxo-4,5-dihydro-10H-imidazo[1,2-a]indeno[1,2-e]pyrazinyl)]-pyrrole-2-carboxylic acid is thus obtained, melting at 265° C. (Analysis, % calculated C: 65.06, H: 3.64, N: 16.86, O: 14.44, % found C: 65.00, H: 3.3, N: 17.0).

EXAMPLE 74

To a solution of 0.31 g of 10-amino-10-methyl-8-(3-methylureido)-5H,10H-imidazo[1,2-a]-indeno[1,2-e]pyrazin-4-one in 20 ml of acetic acid is added 0.11 g of succinic anhydride and the mixture is stirred for 16 hours at a temperature in the region of 20° C. The insoluble product formed is isolated by filtration, washed successively with 2 ml of acetic acid, 5 times with 10 ml in total of distilled water and with 3 ml of acetone, and then dried under reduced pressure (1 mmHg; 0.13 kPa) at 60° C. 0.27 g of 3-{10-[10-methyl-8-(3-methylureido)-4-oxo-4,5-dihydro-10H-imidazo[1,2-a]indeno[1,2-e]pyrazinyl]aminocarbonyl}-propionic acid is thus obtained, decomposing without melting above 250° C. (Analysis, % calculated C: 56.60, H: 4.75, N: 19.80, O: 18.85, % found C: 56.3, H: 4.3, N: 20.0).

EXAMPLE 75

To a suspension, maintained under a nitrogen atmosphere and at a temperature in the region of 20° C., of 2.2 g of 5H,10H-imidazo[1,2-a]indeno[1,2-e]pyrazin-4-one in 45 ml of anhydrous dimethyl sulphoxide are added 1.34 g of 3-fluorobenzaldehyde and then, over 5 minutes, 0.72 g of 80% sodium hydride. The mixture is stirred for 15 hours at the same temperature, followed by slow addition of 45 ml of distilled water and 12 ml of acetic acid. The insoluble product formed is isolated by filtration, washed with distilled water and air-dried. The product obtained (2.6 g) is chromatographed on a column of neutral silica gel, eluting with a dichloromethane/methanol mixture (90/10 by volume). The fractions containing the expected product are concentrated to dryness and the product obtained (1.6 g) is dissolved in 100 ml of dimethylformamide at 100° C. 30 ml of distilled water are then added and the solution is cooled to a temperature in the region of 20° C. The insoluble product formed is isolated by filtration, washed 3 times with 15 ml in total of distilled water and air-dried. The product obtained (0.86 g) is stirred in suspension in 20 ml of boiling methanol and, after cooling, is isolated by filtration, washed with 5 ml of methanol and air-dried. The product obtained (0.56 g) is dissolved in a boiling mixture of 30 ml of acetic acid and 40 ml of dimethylformamide and, after cooling to a temperature in the region of 5° C., the insoluble product formed is isolated by filtration, washed twice with 10 ml in total of acetic acid and twice with 10 ml in total of isopropyl ether, and then dried under reduced pressure (1 mmHg; 0.13 kPa) at 60° C. 0.39 g of 10-(3-fluorobenzylidene)-5H,10H-imidazo[1,2-a]indeno-(1,2-e]pyrazin-4-one is thus obtained, melting at 360° C. (decomposition) (Analysis, % calculated C: 72.94, H: 3.67, F: 5.77, N: 12.76, O: 4.86, % found C: 73.1, H: 3.0, N: 12.5).

EXAMPLE 76

To a suspension of 2.2 g of 5H,10H-imidazo-[1,2-a]indeno[1,2-e]pyrazin-4-one in 45 ml of anhydrous dimethyl sulphoxide, maintained under a nitrogen atmosphere and at a temperature in the region of 20° C., are added 2 g of 3-bromobenzaldehyde followed, over 5 minutes, by 0.72 g of 80% sodium hydride. The mixture is stirred for 15 hours at the same temperature, followed by slow addition of 45 ml of distilled water and 12 ml of acetic acid. The insoluble product formed is isolated by filtration, washed with distilled water and air-dried. The product obtained (3.1 g) is chromatographed on neutral silica gel, eluting with a dichloromethane/methanol mixture (90/10 by volume). The fractions containing the expected product are concentrated to dryness and the product obtained (1.9 g) is dissolved in a boiling mixture of 40 ml of acetic acid and 50 ml of dimethylformamide and, after cooling and storing for 15 hours at a temperature in the region of 5° C., the insoluble product formed is isolated by filtration, washed twice with 10 ml in total of acetic acid and twice with 10 ml in total of isopropyl ether and then dried under reduced pressure (1 mmHg; 0.13 kPa) at 80° C. 0.65 g of 10-(3-bromo-benzylidene)-5H,10H-imidazo[1,2-a]indeno[1,2-e]pyrazin-4-one is thus obtained, melting at 340° C. (decomposition) (Analysis, % calculated C: 61.56, H: 3.10, Br: 20.48, N: 10.77, O: 4.10, % found C: 61.4, H: 3.2, N: 11.0).

EXAMPLE 77

To a solution of 1.23 g of 10-amino-5H,10H-imidazo-[1,2-a]indeno[1,2-e]pyrazin-4-one in 20 ml of acetic acid is added 0.6 g of succinic anhydride and the mixture is stirred for 3 hours at a temperature in the region of 20° C. The insoluble product formed is isolated by filtration, washed twice with 20 ml in total of acetic acid and with 10 ml of acetone, then dried under reduced pressure (1 mmHg; 0.13 kPa) at 100° C. 1.12 g of 3-[10-(4-oxo-4,5-dihydro-10H-imidazo[1,2-a]indeno[1,2-e]pyrazinyl)aminocarbonyl]-propionic acid are thus obtained, decomposing without melting above 250° C. (Analysis, % calculated C: 60.35, H: 4.17, N: 16.56, O: 18.92, % found C: 60.0, H: 4.0, N: 16.4).

EXAMPLE 78

To a suspension of 1.4 g of 10-acetamido-5H,10H-imidazo[1,2-a]indeno[1,2-e]pyrazin-4-one in 35 ml of anhydrous dimethyl sulphoxide, maintained at 20° C. under a nitrogen atmosphere, is added 0.36 g of 80% sodium hydride and the mixture is stirred for 20 minutes. A solution of 0.7 g of benzyl chloride in 1 ml of anhydrous dimethyl sulphoxide is then added dropwise over 5 minutes at the same temperature and, after stirring for 3 hours, the reaction mixture is poured into a mixture of 200 ml of distilled water, 80 g of ice and 6 ml of acetic acid. The insoluble material formed is removed by centrifugation and the supernatant solution is stored for 15 hours at a temperature in the region of 20° C. The insoluble product formed is isolated by filtration, washed twice with 10 ml in total of distilled water and with 5 ml of acetone, and then dried under reduced pressure (1 mmHg; 0.13 kPa) at 80° C. 0.52 g of 10-acetamido-10-benzyl-5H,10H-imidazo[1,2-a]indeno[1,2-e]pyrazin-4-one is thus obtained, melting at 325° C. (decomposition) (Analysis, % calculated C: 71.34, H: 4.90, N: 15.13, O: 8.64, % found C: 71.2, H: 4.5, N: 15.0).

EXAMPLE 79

0.46 g of 10-acetamido-10-ethyl-5H,10H-imidazo[1,2-a]indeno[1,2-e]pyrazin-4-one is dissolved in 25 ml of boiling 2N hydrochloric acid and the solution is stirred for 1 hours at boiling, cooled and concentrated to dryness under reduced pressure (15 mmHg; 2 kPa) at 60° C. The product obtained is suspended in 15 ml of ethanol and the insoluble product is isolated by filtration, washed twice with 10 ml in total of ethanol and dried under reduced pressure (1 mmHg; 0.13 kPa) at 100° C. 0.28 g of 10-amino-10-ethyl-5H,10H-imidazo[1,2-a]indeno[1,2-e]pyrazin-4-one sesquihydrochloride is thus obtained, decomposing without melting above 250° C. (Analysis, % calculated C: 56.13, H: 4.87, Cl: 16.57, N: 17.45, O: 4.98, % found C: 56.2, H: 4.5, Cl: 16.5, N: 17.2).

10-Acetamido-10-ethyl-5H,10H-imidazo-[1,2-a]indeno[1,2-e]pyrazin-4-one may be prepared in the following way: To a suspension of 1.4 g of 10-acetamido-5H,10H-imidazo[1,2-a]indeno[1,2-e]pyrazin-4-one in 35 ml of anhydrous dimethyl sulphoxide, maintained at 20° C. under a nitrogen atmosphere, is added 0.36 g of 80% sodium hydride and the mixture is stirred for 20 minutes. A solution of 0.86 g of ethyl iodide in 1 ml of anhydrous dimethyl sulphoxide is then added dropwise over 5 minutes at the same temperature and, after stirring for 1 hour, the reaction mixture is poured into a mixture of 220 ml of distilled water, 130 g of ice and 3 ml of acetic acid. The mixture is stirred for 15 hours at a temperature in the region of 20° C. and extracted 4 times with 600 ml in total of dichloromethane, and the aqueous phase is concentrated to dryness under reduced pressure (1 mmHg; 0.13 kPa) at 70° C. The product obtained (5.6 g) is suspended in 10 ml of distilled water and, after storing for 30 minutes at a temperature in the region of 5° C., the insoluble product is isolated by filtration, washed twice with 10 ml in total of distilled water and then dried under reduced pressure (1 mmHg; 0.13 kPa) at 80° C. 0.36 g of 10-acetamido-10-ethyl-5H,10H-imidazo-[1,2-a]indeno[1,2-e]pyrazin-4-one is thus obtained.

EXAMPLE 80

0.3 g of 10-acetamido-10-benzyl-5H,10H-imidazo[1,2-a]indeno[1,2-e]pyrazin-4-one is dissolved in 15 ml of boiling 2N hydrochloric acid and the solution is stirred for 1 hour at boiling, cooled and concentrated to dryness under reduced pressure (15 mmHg; 2 kPa) at 60° C. The product obtained is suspended in 3 ml of ethanol and the insoluble product is isolated by filtration, washed with 2 ml of ethanol and dried under reduced pressure (1 mmHg; 0.13 kPa) at 100° C. 0.18 g of 10-amino-10-benzyl-5H,10H-imidazo-[1,2-a]indeno[1,2-e]pyrazin-4-one sesquihydrochloride is thus obtained, decomposing without melting above 250° C. (Analysis, % calculated C: 62.71, H: 4.60, Cl: 13.88, N: 14.63, O: 4.18, % found C: 62.6, H: 4.6, Cl: 14.1, N: 14.5).

EXAMPLE 81

1.5 g of 10-acetamido-10-propyl-5H,10H-imidazo[1,2-a]indeno[1,2-e]pyrazin-4-one are dissolved in 80 ml of boiling 2N hydrochloric acid and the solution is stirred for 2 hours at boiling, cooled and concentrated to dryness under reduced pressure (15 mmHg; 2 kPa) at 60° C. The product obtained is suspended in 35 ml of ethanol and the insoluble product is isolated by filtration, washed twice with 20 ml in total of ethanol and dried under reduced pressure (1 mmHg; 0.13 kPa) at 100° C. 0.87 g of 10-amino-10-propyl-5H,10H-imidazo[1,2-a]indeno[1,2-e]pyrazin-4-one sesquihydrochloride is thus obtained, decomposing without melting above 250° C. (Analysis, % calculated C: 57.36, H: 5.27, Cl: 15.87, N: 16.72, O: 4.78, % found C: 56.9, H: 5.3, Cl: 16.4, N: 16.4).

10-Acetamido-10-propyl-5H,10H-imidazo[1,2-a]-indeno[1,2-e]pyrazin-4-one may be prepared in the following way: To a suspension of 2.4 g of 10-acetamido-5H,10H-imidazo[1,2-a]indeno[1,2-e]pyrazin-4-one in 85 ml of anhydrous dimethyl sulphoxide, maintained at 20° C. under a nitrogen atmosphere, is added 0.6 g of 80% sodium hydride and the mixture is stirred for 30 minutes. A solution of 1.7 g of propyl iodide in 2 ml of anhydrous dimethyl sulphoxide is then added dropwise over 5 minutes at the same temperature and, after stirring for 1 hour, the reaction mixture is poured into a mixture of 370 ml of distilled water, 220 g of ice and 5 ml of acetic acid. The mixture is stirred for 15 hours at a temperature in the region of 20° C. and extracted three times with 600 ml in total of ethyl acetate, and the aqueous phase is concentrated to dryness under reduced pressure (15 mmHg; 2 kPa) at 60° C. The product obtained (8.1 g) is suspended in 30 ml of distilled water and, after stirring for 30 minutes at a temperature in the region of 20° C., the insoluble product is isolated by filtration, washed twice with 30 ml in total of distilled water and then dried under reduced pressure (2 mmHg; 0.26 kPa) at 80° C. 1.5 g of 10-acetamido-10-propyl-5H,10H-imidazo-[1,2-a]indeno[1,2-e]pyrazin-4-one are thus obtained.

EXAMPLE 82

To a solution of 0.5 g of 10-amino-10-methyl-5H,10H-imidazo[1,2-a]indeno[1,2-e]pyrazin-4-one in 20 ml of acetic acid is added 0.24 g of succinic anhydride and the mixture is stirred for 20 hours at a temperature in the region of 20° C. A further 0.06 g of succinic anhydride is added and the mixture is stirred for a further 20 hours at a temperature in the region of 20° C. The insoluble product formed is isolated by filtration and the filtrate is concentrated to dryness under reduced pressure (15 mmHg; 2 kPa) at 60° C. The product obtained is stirred in suspension in 15 ml of ethanol for 30 minutes and the insoluble product formed is isolated by filtration, washed twice with 10 ml in total of ethanol and then dried under reduced pressure (1 mmHg; 0.13 kPa) at 100° C. 0.45 g of 3-[10-(10-methyl-4-oxo-4,5-dihydro-10H-imidazo-[1,2-a]indeno[1,2-e]pyrazinyl)aminocarbonyl]propionic acid is thus obtained, decomposing without melting above 250° C. (Analysis, % calculated C: 61.36, H: 4.58, N: 15.90, O: 18.16, % found C: 61.8, H: 5.2, N: 15.5).

EXAMPLE 83

To a solution of 1 g of 10-amino-10-methyl-5H,10H-imidazo[1,2-a]indeno[1,2-e]pyrazin-4-one in 15 ml of anhydrous dimethylformamide is added dropwise, over 2 minutes at 20° C., a solution of 1.05 g of di-tert-butyl dicarbonate in 5 ml of anhydrous dimethylformamide. The mixture is stirred for 3 hours at a temperature in the region of 20° C. and for 20 hours at 60° C., and then concentrated to dryness under reduced pressure (5 mmHg; 0.65 kPa) at 60° C. The product obtained (1.3 g) is stirred in suspension in 15 ml of ethanol for 30 minutes and the insoluble product formed is isolated by filtration, washed with 5 ml of ethanol and then dried under reduced pressure (1 mmHg; 0.13 kPa) at 50° C. 0.72 g of tert-butyl N-[10-(10-methyl-4-oxo-4,5-dihydro-10H-imidazo[1,2-a]indeno-[1,2-e]pyrazinyl)]carbamate is thus obtained, decomposing without melting above 250° C. (Analysis, % calculated C: 64.76, H: 5.72, N: 15.90, O: 13.62, % found C: 64.4, H: 5.4, N: 15.9).

EXAMPLE 84

To a solution of 0.5 g of 10-amino-10-methyl-5H,10H-imidazo[1,2-a]indeno[1,2-e]pyrazin-4-one in 20 ml of acetic acid is added 0.35 g of glutaric anhydride and the mixture is stirred for 20 hours at a temperature in the region of 20° C. and then concentrated to dryness under reduced pressure (15 mmHg; 2 kPa) at 50° C. The product obtained (1.64 g) is stirred in suspension in 15 ml of ethyl acetate for 1 hour and the insoluble product formed is isolated by filtration, washed with 10 ml of ethyl acetate and then air-dried. The product obtained (0.55 g) is stirred in suspension in 10 ml of boiling distilled water for 5 minutes, and at a temperature in the region of 20° C. for 30 minutes. The insoluble product is isolated by filtration, washed with 5 ml of distilled water and with 5 ml of ethanol, and then air-dried. The product obtained (0.34 g) is chromatographed on neutral silica gel, eluting with a chloroform/methanol/28% aqueous ammonia mixture (65/30/5 by volume). The fractions containing the expected product are concentrated to dryness and the product obtained (0.27 g) is stirred in suspension in 5 ml of isopropyl ether. The insoluble product is isolated by filtration, washed with 5 ml of isopropyl ether and dried under reduced pressure (1 mmHg; 0.13 kPa) at 100° C. 0.21 g of 4-[10-(10-methyl-4-oxo-4,5-dihydro-10H-imidazo[1,2-a]indeno[1,2-e]pyrazinyl)-aminocarbonyl]butyric acid partially salified (25%) in the form of the ammonium salt is thus obtained, melting at 196° C. (Analysis, % calculated C: 61.57, H: 5.10, N: 16.06, O: 17.27, % found C: 61.5, H: 5.1, N: 16.1).

EXAMPLE 85

1.18 g of 10-acetamido-10-isopropyl-5H,10H-imidazo[1,2-a]indeno[1,2-e]pyrazin-4-one are dissolved in 25 ml of boiling 2N hydrochloric acid and the solution is stirred for 1 hours at boiling, cooled and concentrated to dryness under reduced pressure (15 mmHg; 2 kPa) at 60° C. The product obtained is dissolved in 20 ml of ethanol and, after addition of decolorizing charcoal, the solution is filtered. The filter is washed with 20 ml of ethanol and the filtrate and washing are then combined, 200 ml of acetone are added and the solution is stored for 45 minutes at a temperature in the region of 5° C. The insoluble product formed is isolated by filtration, washed with 10 ml of acetone and dried under reduced pressure (1 mmHg; 0.13 kPa) at 60° C. The product obtained (0.6 g) is stirred in suspension in 20 ml of boiling isopropyl ether for 15 minutes and, after cooling to a temperature in the region of 20° C., the insoluble product is isolated by filtration, washed twice with 20 ml in total of isopropyl ether and dried under reduced pressure (1 mmHg; 0.13 kPa) at 60° C. 0.46 g of 10-amino-10-isopropyl-5H,10H-imidazo[1,2-a]indeno-[1,2-e]pyrazin-4-one hydrochloride is thus obtained, decomposing without melting above 250° C. (Analysis, % calculated C: 58.97, H: 5.34, Cl: 13.60, N: 17.19, O: 4.91, % found C: 59.0, H: 5.4, Cl: 13.6, N: 16.8, O: 4.9).

10-Acetamido-10-isopropyl-5H,10H-imidazo-[1,2-a]indeno[1,2-e]pyrazin-4-one may be prepared in the following way: To a suspension of 2.4 g of 10-acetamido-5H,10H-imidazo[1,2-a]indeno[1,2-e]pyrazin-4-one in 85 ml of anhydrous dimethyl sulphoxide, maintained at 20° C. under a nitrogen atmosphere, is added 0.6 g of 80% sodium hydride and the mixture is stirred for 30 minutes. A solution of 1.7 g of isopropyl iodide in 2 ml of anhydrous dimethyl sulphoxide is then added dropwise over 5 minutes at the same temperature and, after stirring for 1 hour, the reaction mixture is poured into a mixture of 370 ml of distilled water, 220 g of ice and 5 ml of acetic acid. The mixture is stirred for 15 hours at a temperature in the region of 20° C. and extracted 3 times with 600 ml in total of ethyl acetate, and the aqueous phase is concentrated to dryness under reduced pressure (15 mmHg; 2 kPa) at 60° C. The product obtained (7.9 g) is suspended in 30 ml of distilled water and, after stirring for 30 minutes at a temperature in the region of 20° C., the insoluble product is isolated by filtration, washed twice with 30 ml in total of distilled water and twice with 20 ml in total of isopropanol and then dried under reduced pressure (2 mmHg; 0.26 kPa) at 100° C. 0.9 g of 10-acetamido-10-isopropyl-5H,10H-imidazo[1,2-a]indeno[1,2-e]pyrazin-4-one is thus obtained.

EXAMPLE 86

1.3 g of 10-acetamido-10-butyl-5H,10H-imidazo[1,2-a]indeno[1,2-e]pyrazin-4-one are dissolved in 25 ml of boiling 2N hydrochloric acid and the solution is stirred for 1 hours 30 minutes at boiling, cooled and concentrated to dryness under reduced pressure (15 mmHg; 2 kPa) at 60° C. The product obtained is dissolved in 30 ml of methanol and, after addition of decolorizing charcoal, the solution is filtered. The filter is washed with 10 ml of methanol, and the filtrate and washing are combined, 400 ml of acetone are added and the solution is stored for 1 hour at a temperature in the region of 20° C. The insoluble product formed is isolated by filtration, washed twice with 100 ml in total of acetone and dried under reduced pressure (1 mmHg; 0.13 kPa) at 20° C. 0.83 g of 10-amino-10-butyl-5H,10H-imidazo[1,2-a]indeno[1,2-e]-pyrazin-4-one hydrochloride (1.8 mol of acid per mole of base) is thus obtained, decomposing without melting above 250° C. (Analysis, % calculated C: 57.01, H: 5.56, Cl: 17.32, N: 15.64, O: 4.47, % found C: 56.9, H: 5.4, Cl: 17.5, N: 15.7).

10-Acetamido-10-butyl-5H,10H-imidazo[1,2-a]-indeno[1,2-e]pyrazin-4-one may be prepared in the following way: To a suspension of 2.4 g of 10-acetamido-5H,10H-imidazo[1,2-a]indeno[1,2-e]pyrazin-4-one in 85 ml of anhydrous dimethyl sulphoxide, maintained at 20° C. under a nitrogen atmosphere, is added 0.6 g of 80% sodium hydride and the mixture is stirred for 30 minutes. A solution of 1.8 g of butyl iodide in 2 ml of anhydrous dimethyl sulphoxide is then added dropwise over 5 minutes at the same temperature and, after stirring for 2 hours, the reaction mixture is poured into a mixture of 370 ml of distilled water, 220 g of ice and 5 ml of acetic acid. The mixture is stirred for 15 hours at a temperature in the region of 20° C. and then extracted 3 times with 600 ml in total of ethyl acetate, and the aqueous phase is concentrated to dryness under reduced pressure (15 mmHg; 2 kPa) at 60° C. The product obtained (7.9 g) is suspended in 30 ml of distilled water and, after stirring for 30 minutes at a temperature in the region of 20° C., the insoluble product is isolated by filtration, washed twice with 20 ml in total of distilled water and then dried under reduced pressure (2 mmHg; 0.26 kPa) at 100° C. 1.3 g of 10-acetamido-10-butyl-5H,10H-imidazo-[1,2-a]indeno[1,2-e]pyrazin-4-one are thus obtained.

EXAMPLE 87

0.71 g of tert-butyl N-benzyl-N-[10-(10-methyl-4-oxo-4,5-dihydro-10H-imidazo[1,2-a]indeno-[1,2-e]pyrazinyl)] carbamate is dissolved in 10 ml of trifluoroacetic acid and the solution is stored for 1 hour at a temperature in the region of 20° C. and then concentrated to dryness under reduced pressure (15 mmHg; 2 kPa) at 60° C. 50 ml of distilled water and 10 ml of saturated aqueous sodium hydrogen carbonate solution are then added. After stirring for 1 hour at a temperature in the region of 20° C., the insoluble product formed is isolated by filtration, washed twice with 50 ml in total of distilled water and air-dried; a first batch of 0.33 g is thus obtained. The filtrate and the aqueous washings are combined and extracted 3 times with 150 ml in total of dichloromethane. The extracts are combined, washed with 25 ml of distilled water, dried over anhydrous magnesium sulphate and concentrated to dryness under reduced pressure (15 mmHg; 2 kPa) at 40° C.; a second batch of 0.085 g is thus obtained. The two batchs are combined and dissolved in 40 ml of dichloromethane, and the solution is washed twice with 30 ml in total of distilled water, dried over anhydrous magnesium sulphate and concentrated to dryness under reduced pressure (15 mmHg; 2 kPa) at 30° C. The product obtained (0.3 g) is suspended in 10 ml of isopropyl ether and the insoluble product is isolated by filtration, washed twice with 10 ml in total of isopropyl ether and then dried under reduced pressure (1 mmHg; 0.13 kPa) at 60° C. 0.25 g of 10-benzylamino-10-methyl-5H,10H-imidazo[1,2-a]indeno[1,2-e]pyrazin-4-one is thus obtained, melting at 136° C. (decomposition) (Analysis, % calculated C: 73.67, H: 5.30, N: 16.36, O: 4.67, % found C: 74.0, H: 5.5, N: 15.9).

tert-Butyl N-benzyl-N-[10-(10-methyl-4-oxo-4,5-dihydro-10H-imidazo[1,2-a]indeno[1,2-e]pyrazinyl)]-carbamate may be prepared in the following way: To a suspension of 1.8 g of tert-butyl N-[10-(10-methyl-4-oxo-4,5-dihydro-10H-imidazo[1,2-a]indeno[1,2-e]-pyrazinyl)] carbamate in 35 ml of anhydrous dimethylformamide, maintained at 20° C. under a nitrogen atmosphere, is added 0.6 g of 80% sodium hydride and the mixture is stirred for 30 minutes. A solution of 0.7 g of benzyl chloride in 1.5 ml of anhydrous dimethylformamide is then added dropwise over 5 minutes at the same temperature, the mixture is stirred for 3 hours, 0.1 g of benzyl chloride is added and the reaction mixture is stirred for 30 minutes and poured into a mixture of 160 ml of distilled water, 100 g of ice and 2.5 ml of acetic acid. The insoluble product formed is isolated by filtration, washed twice with 50 ml in total of distilled water and then air-dried. The product obtained (1.1 g) is chromatographed on neutral silica gel, eluting first with ethyl acetate and then with an ethyl acetate/methanol mixture (95/5 by volume). The fractions containing the expected product are concentrated to dryness. 0.71 g of tert-butyl N-benzyl-N-[10-(10-methyl-4-oxo-4,5-dihydro-10H-imidazo[1,2-a]indeno[1,2-e]pyrazinyl)]carbamate is thus obtained.

EXAMPLE 88

1.96 g of tert-butyl N-methyl-N-[10-(10-methyl-4-oxo-4,5-dihydro-10H-imidazo[1,2-a]indeno-[1,2-e]pyrazinyl)] carbamate are dissolved in 25 ml of trifluoroacetic acid and the solution is stored for 1 hour 30 minutes at a temperature in the region of 20° C. and then concentrated to dryness under reduced pressure (15 mmHg; 2 kPa) at 60° C. 3.85 g (out of the 4.5 g obtained in total) are dissolved in 370 ml of methanol and, after addition of decolorizing charcoal, the solution is filtered. 50 ml of 1.3N hydrochloric methanol are then added to the filtrate, followed by concentration of the solution to dryness under reduced pressure (15 mmHg; 2 kPa) at 40° C. The product obtained (1.9 g) is suspended in 20 ml of methanol and the insoluble product is isolated by filtration, washed twice with 20 ml in total of methanol and then dried under reduced pressure (1 mmHg; 0.13 kPa) at 60° C. 0.89 g of 10-methyl-10-methylamino-5H,10H-imidazo-[1,2-a]indeno[1,2-e]pyrazin-4-one dihydrochloride is thus obtained, decomposing without melting above 250° C. (Analysis, % calculated C: 53.11, H: 4.75, Cl: 20.90, N: 16.52, O: 4.72, % found C: 53.3, H: 4.7, Cl: 20.7, N: 16.4, O: 4.6).

tert-Butyl N-methyl-N-[10-(10-methyl-4-oxo-4,5-dihydro-10H-imidazo[1,2-a]indeno[1,2-e]pyrazinyl)] carbamate may be prepared in the following way: To a suspension of 6.3 g of tert-butyl N-[10-(10-methyl-4-oxo-4,5-dihydro-10H-imidazo[1,2-a]indeno[1,2-e]-pyrazinyl)] carbamate in 125 ml of anhydrous dimethylformamide, maintained at 20° C. under a nitrogen atmosphere, are added 2.2 g of 80% sodium hydride and the mixture is stirred for 30 minutes. A solution of 2.8 g of methyl iodide in 6 ml of anhydrous dimethylformamide is then added dropwise over 5 minutes at the same temperature, and the reaction mixture is stirred for 2 hours and poured into a mixture of 580 ml of distilled water, 360 g of ice and 10 ml of acetic acid. The solution obtained is extracted 4 times with 3 liters in total of ethyl acetate and the organic extracts are then combined, washed with 750 ml of distilled water, dried over anhydrous magnesium sulphate and concentrated to dryness under reduced pressure (5 mmHg; 2 kPa) at 40° C. The product obtained (4.2 g) is suspended in 10 ml of acetone and the insoluble product is isolated by filtration, washed twice with 10 ml in total of acetone and air-dried. 2 g of tert-butyl N-methyl-N-[10-(10-methyl-4-oxo-4,5-dihydro-10H-imidazo[1,2-a]indeno[1,2-e]pyrazinyl)]-carbamate are thus obtained.

EXAMPLE 89

To 0.9 g of 7-chloro-5H,10H-imidazo[1,2-a]-indeno[1,2-e]pyrazin-4-one dissolved in 15 ml of anhydrous dimethyl sulphoxide at a temperature in the region of 20° C. is added 0.48 g of glyoxylic acid monohydrate, followed by portionwise addition of 0.77 g of 60% sodium hydride. The reaction is continued for 18 hours at the same temperature. The reaction medium is then acidified using acetic acid (9 ml) and then heated at 80° C. for 4 hours. After cooling to 20° C., 100 ml of distilled water are added and the brown precipitate formed is filtered off, washed with water and dried. The solid is taken up in acetone, filtered off and washed several times with acetone and with methanol. After drying under reduced pressure (1 mmHg; 0.13 kPa) at 45° C., 0.72 g of the sodium salt of 10-carboxymethylene-7-chloro-5H-imidazo[1,2-a]indeno-[1,2-e]pyrazin-4-one is obtained in the form of a green solid, the melting point of which is greater than 260° C. (Analysis, $C_{15}H_7ClN_3NaO_3$; % calculated C: 53.67; H: 2.10; Cl: 10.56; N: 12.52; Na: 6.85; % found C: 53.3, H: 2.5; Cl: 10.6; N: 12.5; Na: 5.4).

7-Chloro-5H,10H-imidazo[1,2-a]indeno[1,2-e]-pyrazin-4-one may be prepared in the following way: 1 g of 1-[2-(6-chloro-1-oxoindanyl)]imidazole-2-carboxamide is dissolved in 50 ml of boiling methanol and, after addition of 0.1 g of decolorizing charcoal, the solution is filtered. The filter is washed with 25 ml of boiling methanol, then the filtrate and the washing are combined, 15 ml of aqueous 12N hydrochloric acid solution are added and the mixture is stored for 3 hours at 5° C. The crystals are isolated by filtration, washed twice with 20 ml in total of chilled methanol and dried under reduced pressure (1 mmHg; 0.13 kPa) at 60° C. 0.4 g of 7-chloro-5H,10H-imidazo-[1,2-a]indeno(1,2-e]pyrazin-4-one hydrochloride is thus obtained, decomposing without melting above 300° C. [NMR spectrum: (300 MHz; DMSO-$d_6$; δ in ppm): 4.12 (s, 2H: —C$\underline{H}_2$— at 10); 7.44 (dd, J=8 and 1 Hz 1H: —$\underline{H}$8); 7.66 (d, J=8 Hz, 1H: —$\underline{H}$9); 7.95 and 8.25 (2 broad s, 1H each: —$\underline{H}$ of the imidazole); 8.05 (d, J=1 Hz, 1H: —$\underline{H}$6); 12.97 (mult., 1H: —CON$\underline{H}$—)].

1-[2-(6-Chloro-1-oxoindanyl)]imidazole-2-carboxamide may be prepared in the following way: 1.2 g of ethyl 1-[2-(6-chloro-1-oxoindanyl)]imidazole-2-carboxylate are dissolved in 45 ml of 2.5N ammoniacal methanol solution and the solution is stored for 20 hours at a temperature in the region of 20° C. and then concentrated to dryness under reduced pressure (15 mmHg; 2 kPa) at 35° C. The product obtained is suspended in 50 ml of isopropyl ether, filtered off, washed twice with 20 ml in total of isopropyl ether and then dried under reduced pressure (15 mmHg; 2 kPa) at a temperature in the region of 20° C. 1 g of 1-[2-(6-chloro-1-oxoindanyl)]imidazole-2-carboxamide is thus obtained in the form of a solid melting at 190° C.

Ethyl 1-[2-(5-fluoro-1-oxoindanyl)]imidazole-2-carboxylate may be prepared in the following way: a solution of 2.5 g of ethyl imidazole-2-carboxylate in 70 ml of anhydrous dimethylformamide is added dropwise, over 20 minutes at a temperature between 20° C. and 25° C., to a suspension of 0.7 g of 80% sodium hydride in 10 ml of anhydrous dimethylformamide, maintained under a nitrogen atmosphere. After stirring for 15 minutes, a solution of 5.4 g of 2-bromo-6-chloro-1-indanone in 20 ml of anhydrous dimethylformamide is added dropwise over 10 minutes at the same temperature. The mixture is stirred for 1 hour 30 minutes and is then extracted with chloroform. After chromatography on silica gel with a dichloromethane/ethyl acetate mixture (70/30 by volume) 1 g of ethyl 1-[2-(6-chloro-1-oxoindanyl)]-imidazole-2-carboxylate is obtained, melting at 180° C.

2-Bromo-6-chloro-1-indanone may be prepared as described in German Patent 2,640,358.

EXAMPLE 90

0.4 g of 10-amino-10-methyl-8-(3-methyl-ureido)-5H, 10H-imidazo[1,2-a]indeno[1,2-e]pyrazin-4-one hydrochloride dissolved in 25 ml of methanol containing triethylamine is chromatographed on a 23 cm column 6 cm in diameter packed with 400 g of silica coated with cellulose tris(3,5-dimethylphenylcarbamate) (Chiralcel OD type). The elution is carried out using a heptane/ethanol mixture (20/80 by volume) containing 0.05% triethylamine. The flow rate is 35 ml per minute and UV detection is performed at 254 nm. This operation is repeated 15 times in order to produce the two enantiomers of 10-amino-10-methyl-8-(3-methylureido)-5H,10H-imidazo[1,2-a]indeno[1,2-e] pyrazin-4-one after concentration to dryness under reduced pressure of the fractions obtained: 1.79 g of laevorotatory enantiomer ($[\alpha]^{20}_D = -90.3°\pm1.2°$) are thus isolated first, in the form of a white powder decomposing without melting at about 200° C. (Analysis, $C_{16}H_{16}N_6O_2.0.21\ H_2O.1.0$ EtOH % calculated C: 59.25; H: 4.97; N: 25.91, % found C: 59.5; H: 4.9; N: 25.7); 1.47 g of the dextrorotatory enantiomer ($[\alpha]^{20}_D = 89.00°\pm10°$) are then isolated in the form of a pale yellow powder decomposing without melting at about 200° C. (Analysis, $C_{16}H_{16}N_6O_2.0.21\ H_2O.1.0$ EtOH % calculated C: 59.25; H: 4.97; N: 25.91; % found C: 59.6; H: 5.0; N: 26.1). The purity of the two enantiomers is checked by chromatography under the same conditions (column: 25 cm/4.6 mm; Chiralcel OD type phase; eluent: EtOH/ heptane: 80/20; flow rate: 1 ml/min; UV detection at 254 nm): the purity is greater than 98% for the first enantiomer and greater than 90% for the second.

EXAMPLE 91

The process is performed as in Example 9 but starting with 1.6 g of 5H,10H-imidazo[1,2-a]indeno-[1,2-e]pyrazin-4-one, 29 ml of dimethyl sulphoxide, 1.2 g of 1,3-dimethyl-1H-pyrazole-4-carboxaldehyde and 0.43 g of 80% sodium hydride. After hydrolysis of the reaction mixture and filtration, the green solid obtained (2.2 g) is crystallized from 50 ml of dimethylformamide. The crystals are filtered off, washed with acetone and dried at 60° C. under vacuum (1 mmHg; 0.13 kPa). 1.5 g of 10-(1,3-dimethyl-1H-pyrazole-4-methylene)-5H,10H-imidazo(1,2-a]indeno[1,2-e]pyrazin-4-one are obtained in the form of a greenish solid melting above 260° C. (Analysis, % calculated C: 69.29, H: 4.59, N: 21.26, O: 4.86, % found C: 69.3, H: 4.5, N: 21.2).

1,3-Dimethyl-1H-pyrazole-4-carboxaldehyde may be prepared in the following way: to a solution, cooled to a temperature in the region of −65° C., of 1.8 ml of oxalyl chloride in 44 ml of dichloromethane are added dropwise, with stirring, 3 ml of dimethyl sulphoxide followed by a solution of 2.3 g of 1,3-dimethyl-1H-pyrazole-4-methanol in 18 ml of dichloromethane, while maintaining the cooling bath at −70° C. during the addition and for 15 minutes after the end of the addition. 12.7 ml of triethylamine are then added over 10 minutes and the reaction medium is allowed to return to a temperature in the region of 20° C. Stirring is thus continued for 22 hours, and the reaction mixture is then treated with 100 ml of distilled water. The organic phase is washed successively with saturated sodium chloride solution (30 ml), 1% hydrochloric acid solution (44 ml), 5% sodium carbonate solution (60 ml) and distilled water (30 ml). After drying over magnesium sulphate, the organic solution is evaporated on a rotary evaporator. 1.3 g of 1,3-dimethyl-1H-pyrazole-4-carboxaldehyde are obtained in the form of a dark yellow oil which is used without further purification in the subsequent syntheses (Rf=0.86, thin layer chromatography on silica gel, solvent: chloroform/methanol/28% aqueous ammonia (24/6/1 by volume)).

1,3-Dimethyl-1H-pyrazole-4-methanol may be prepared in the following way: to a suspension, cooled to a temperature in the region of −15° C., of 3.4 g of lithium aluminium hydride in 65 ml of ethyl ether is added, over 20 minutes and under a stream of argon, a solution of 9.7 g of ethyl 1,3-dimethyl-1H-pyrazole-4-carboxylate in 130 ml of ethyl ether. The reaction medium is then allowed to return to a temperature in the region of 25° C. and the stirring is continued for 2 hours 30 minutes. The reaction mixture is treated with 60 ml of ethyl acetate and then filtered. The solid obtained is added, portionwise and with stirring, to 84 ml of 10% sulphuric acid. The mixture is filtered and 23 ml of concentrated sodium hydroxide are added to the filtrate. Three extractions with ethyl acetate (3×200 ml) are then carried out and the organic phases are combined and evaporated on a rotary evaporator. 5.1 g of 1,3-dimethyl-1H-pyrazole-4-methanol are obtained in the form of a colourless oil which is used without further purification in the subsequent syntheses (Rf=0.17, thin layer chromatography on silica gel, solvent: dichloromethane/methanol (95/5 by volume)).

Ethyl 1,3-dimethyl-1H-pyrazole-4-carboxylate may be prepared according to the process described by G. Menozzi et al., J. Het. Chem., 24, 1669 (1987).

EXAMPLE 92

A mixture of 3.7 g of 5-oxazolecarboxaldehyde, 2.8 g of 5H,10H-imidazo1,2-a]indeno[1,2-e]-pyrazin-4-one and 0.62 g of ammonium acetate in 40 ml of acetic anhydride is refluxed for 48 hours. The reaction mixture is poured into 70 ml of distilled water and the precipitate is filtered off and air-dried. The crude product obtained (2 g) is purified by chromatography on a column of silica (200 g), eluting with a mixture of chloroform/methanol/28% aqueous ammonia (24/6/1 by volume). The product thus purified (0.67 g) is triturated with 15 ml of dimethylformamide, filtered off, washed with methanol and dried at 60° C. under vacuum (1 mmHg; 0.13 kPa). 0.3 g of 10-(5-oxazolyl-methylene)-5H,10H-imidazo-[1,2-a]indeno(1,2-e]pyrazin-4-one is obtained in the form of an orange-red coloured solid melting above 260° C. (Analysis, % calculated C: 67.55, H: 3.33, N: 18.53, O: 10.59, % found C: 67.5, H: 3.0, N: 18.5).

5-Oxazolecarboxaldehyde may be prepared in the following way: a mixture of 4.3 g of 5-diethoxymethyloxazole, 50 ml of tetrahydrofuran and 1.7 ml of 0.1N hydrochloric acid is stirred at a temperature in the region of 20° C. for 18 hours. The reaction mixture is concentrated on a rotary evaporator, ethyl ether is added to the evaporation residue and the mixture is evaporated once again. 3.7 g of 5-oxazolecarboxaldehyde are obtained in the form of a light red oil which is used immediately in the subsequent syntheses.

5-Diethoxymethyloxazole may be prepared according to the process described by A. S. Kende et al., J. Am. Chem. Soc., 112, 4070 (1990).

EXAMPLE 93

The process is performed as in Example 92 but starting with 0.45 g of 5-thiazolecarboxaldehyde, 0.45 g of 5H,10H-imidazo[1,2-a]indeno[1,2-e]pyrazin-4-one, 0.2 g of ammonium acetate and 4 ml of acetic anhydride. 0.35 g of 10-(5-thiazolylmethylene)-5H,10H-imidazo[1,2-a]indeno [1,2-e]pyrazin-4-one is obtained in the form of a dark red solid melting above 260° C. (Analysis, % calculated C: 64.14, H: 3.17, N: 17.60, O: 5.03, S: 10.07, % found C: 64.2, N: 17.2, S: 9.7).

5-Thiazolecarboxaldehyde may be prepared according to the process described in German Patent 1,182,234.

EXAMPLE 94

The process is performed as in Example 91 but starting with 0.43 g of 5H,10H-imidazo[1,2-a]indeno-[1,2-e]pyrazin-4-one, 8 ml of dimethyl sulphoxide, 0.32 g of 1,5-dimethyl-1H-pyrazole-4-carboxaldehyde and 0.14 g of 80% sodium hydride. 0.25 g of 10-(1,5-dimethyl-1H-pyrazole-4-methylene)-5H,10H-imidazo-[1,2-a]indeno[1,2-e]pyrazin-4-one are obtained in the form of a greenish-yellow solid melting above 260° C. (Analysis, % calculated C: 69.29, H: 4.59, N: 21.26, O: 4.86, % found C: 69.3, H: 4.6, N: 21.2).

1,5-Dimethyl-1H-pyrazole-4-carboxaldehyde may be prepared as in Example 91 for the preparation of 1,3-dimethyl-1H-pyrazole-4-carboxaldehyde but starting with 0.7 ml of oxalyl chloride, 1.2 ml of dimethyl sulphoxide, 0.9 g of 1,5-dimethyl-1H-pyrazole-4-methanol, 5 ml of triethylamine and 28 ml of dichloromethane. 0.32 g of 1,5-dimethyl-1H-pyrazole-4-carboxaldehyde is obtained in the form of a light yellow oil which is used without further purification in the subsequent syntheses (Rf=0.49, thin layer chromatography on silica gel, solvent: dichloromethane/methanol (95/5 by volume)).

1,5-Dimethyl-1H-pyrazole-4-methanol may be prepared as in Example 91 for the preparation of 1,3-dimethyl-1H-pyrazole-4-methanol but starting with 1.7 g of lithium aluminium hydride, 4.8 g of ethyl 1,5-dimethyl-1H-pyrazole-4-carboxylate and 100 ml of ethyl ether. 0.7 g of 1,5-dimethyl-1H-pyrazole-4-methanol is obtained in the form of a colourless oil which crystallizes (m.p.=83° C.).

Ethyl 1,5-dimethyl-1H-pyrazole-4-carboxylate may be prepared according to the process described by G. Menozzi et al., J.Het.Chem., 24, 1669 (1987).

The medicaments according to the invention consist of a compound of formula (I) or a salt of such a compound, in the pure state or in the form of a composition in which it is combined with any other pharmaceutically compatible product, which may be inert or physiologically active. The medicaments according to the invention may be employed via the oral, parenteral, rectal or topical route.

As solid compositions for oral administration, tablets, pills, powders (gelatin capsules or wafer capsules) or granules may be used. In these compositions, the active principle according to the invention is mixed with one or more inert diluents, such as starch, cellulose, sucrose, lactose or silica, under a stream of argon. These compositions may also contain substances other than diluents, for example one or more lubricating agents such as magnesium stearate or talc, a dye, a coating agent (dragees) or a varnish.

As liquid compositions for oral administration, pharmaceutically acceptable solutions, suspensions, emulsions, syrups and elixirs containing inert diluents such as water, ethanol, glycerol, vegetable oils or paraffin oil, may be used. These compositions may contain substances other than diluents, for example wetting, sweetening, thickening, flavouring or stabilizing products.

The sterile compositions for parenteral administration may preferably be aqueous or non-aqueous solutions, suspensions or emulsions. Water, propylene glycol, a polyethylene glycol, vegetable oils, in particular olive oil, injectable organic esters, for example ethyl oleate, or other suitable organic solvents may be employed as solvent or vehicle. These compositions may also contain adjuvants, in particular wetting, tonicity, emulsifying, dispersing and stabilizing agents. The sterilization may be effected in several ways, for example by aseptic filtration, by incorporating sterilizing agents into the composition, by irradiation or by heating. They may also be prepared in the form of sterile solid compositions which may be dissolved at the time of use in sterile water or any other injectable sterile medium.

The compositions for rectal administration are suppositories or rectal capsules which contain, besides the active product, excipients such as cocoa butter, semi-synthetic glycerides or polyethylene glycols.

The compositions for topical administration may be, for example, creams, lotions, eye drops, mouth washes, nasal drops or aerosols.

In human therapy, the compounds according to the invention are particularly useful for the treatment and/or prevention of conditions which require the administration of an AMPA-receptor antagonist or of an NMDA-receptor antagonist. These compounds are especially useful for treating or preventing all ischaemias and in particular cerebral ischaemia, the effects due to anoxia, the development of neurodegenerative diseases, Huntington's chorea, Alzheimer's disease, amyotrophic lateral sclerosis, olivopontocerebellar atrophy and Parkinson's disease, with regard to epilepsy-causing and/or convulsive symptoms, for the treatment of cerebral and spinal trauma, trauma associated with degeneration of the inner ear or of the retina, of anxiety, depression, schizophrenia, Tourette's syndrome, hepatic encephalopathy, as analgesics, as anti-inflammatory agents, as anti-anorectic agents, as anti-migraine agents and as anti-emetic agents and for the treatment of poisoning by neurotoxins or other substances which are agonists of the NMDA receptor, as well as neurological disorders associated with viral diseases such as AIDS, rabies, measles and tetanus. These compounds are also useful for the prevention of the withdrawal symptoms associated with drugs and alcohol, and for inhibiting the addiction to and dependency on opiates, and for the treatment of deficiencies associated with mitochondrial anomalies such as mitochondrial myopathy, Leber's syndrome, Wernicke's encephalopathy, Rett's syndrome, homocysteinaemia, hyperprolinaemia, hydroxybutyric aminoaciduria, saturnine encephalopathy (chronic lead poisoning), and sulphite oxidase deficiency.

The doses depend upon the effect sought, the duration of the treatment and the administration route used; they are generally between 10 mg and 100 mg per day via the oral route for an adult, with unit doses ranging from 5 mg to 50 mg of active substance.

Generally speaking, the doctor will determine the appropriate dosage depending on the age, weight and all the other factors which are specific to the subject to be treated.

The examples which follow illustrate compositions according to the invention:

EXAMPLE A

Gelatin capsules containing 50 mg of active product and having the following composition are prepared according to the usual technique:

| | |
|---|---|
| Compound of formula (I) | 50 mg |
| Cellulose | 18 mg |
| Lactose | 55 mg |
| Colloidal silica | 1 mg |
| Sodium carboxymethyl starch | 10 mg |
| Talc | 10 mg |
| Magnesium stearate | 1 mg |

EXAMPLE B

Tablets containing 50 mg of active product and having the following composition are prepared according to the usual technique:

| | |
|---|---|
| Compound of formula (I) | 50 mg |
| Lactose | 104 mg |
| Cellulose | 40 mg |
| Polyvidone | 10 mg |
| Sodium carboxymethyl starch | 22 mg |
| Talc | 10 mg |
| Magnesium stearate | 2 mg |
| Colloidal silica | 2 mg |
| Mixture of hydroxymethyl cellulose, glycerol and titanium oxide (72/3.5/24.5) q.s. 1 finished film-coated tablet weighing 245 mg | |

EXAMPLE C

An injectable solution containing 10 mg of active product and having the following composition is prepared:

| | |
|---|---|
| Compound of formula (I) | 10 mg |
| Benzoic acid | 80 mg |
| Benzyl alcohol | 0.06 ml |
| Sodium benzoate | 80 mg |
| 95% ethanol | 0.4 ml |
| Sodium hydroxide | 24 mg |
| Propylene glycol | 1.6 ml |
| Water | q.s. 4 ml |

We claim:

1. A pharmaceutical composition comprising a pharmaceutically effective amount of at least one compound of formula (I):

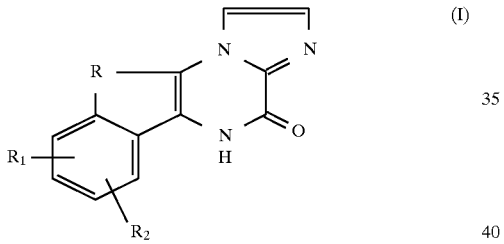

in which

R represents a radical C=$R_3$, C($R_4$)$R_5$ or CH—$R_6$, $R_1$ and $R_2$, which may be identical or different, represent hydrogen or halogen atoms or alkyl, alkoxy, amino, —N=CH—N(alk)alk', nitro, cyano, phenyl, imidazolyl, $SO_3H$, hydroxyl, polyfluoroalkoxy, —$COOR_7$, —NH—CO—$NR_8R_9$, —N(alk)—CO—$NR_8R_9$, —N(alk-Ar)—CO—$NR_8R_9$, —NH—CS—$NR_8R_9$, —N(alk)—CS—$NR_8R_9$, —NH—CO—$R_{18}$, —NH—CS—$R_{19}$, —NH—C(=$NR_{20}$)—$NR_7R_9$, —N(alk)—C(=$NR_{20}$)—$NR_7R_9$, —NH—$SO_2$—$NR_7R_9$, —N(alk)—$SO_2$—$NR_7R_9$, —CO—$NR_7R_9$, —NH—$SO_2$—$CF_3$, —NH—$SO_2$-alk, —$NR_9R_{11}$, —S(O)$_m$-alk-Ar or —$SO_2$—$NR_7R_9$ radicals, 2-oxo-1-imidazolidinyl radicals in which position –3 is optionally substituted with an alkyl radical, or 2-oxoperhydro-1-pyrimidinyl radicals in which position –3 is optionally substituted with an alkyl radical, $R_3$ represents a radical NO-alk, CHR$_{10}$, NR$_7$, C(COOR$_7$)R$_{16}$ or C(CONR$_7R_{15}$)R$_{16}$, $R_4$ represents an alkyl, -alk-Het or -alk-Het" radical or a phenylalkyl radical in which the phenyl ring is optionally substituted with one or more substituents selected from halogen atoms and alkyl, alkoxy, nitro, amino, hydroxyl, cyano, -alk-$NH_2$, —$COOR_7$ and -alk-$COOR_7$ radicals, $R_5$ represents a radical —$NR_{12}R_{13}$, —NH—CHO, —NH—$COOR_{17}$, —NH—$SO_2R_{19}$, —$COOR_7$, -alk-$COOR_7$, -alk-$CONR_7R_{15}$, -alk-$NR_7R_{15}$, -alk-OH, -alk-CN or -alk-Het", a phenylalkyl radical in which the phenyl ring is substituted with one or more substituents selected from halogen atoms and alkyl, alkoxy, nitro, amino, hydroxyl, cyano, -alk-$NH_2$, —$COOR_7$ and -alk-$COOR_7$ radicals, a radical —NH—CO—Ar in which Ar is optionally substituted with one or more substituents selected from halogen atoms and alkyl, alkoxy, nitro, amino, hydroxyl, cyano, -alk-$NH_2$, —$COOR_7$ and -alk-$COOR_7$ radicals, a radical —NH—CO—Het, —NH—CO—Het", —NH—CO-alk-Het, —NH—CO-alk-Het", —NH—CO-alk-$COOR_7$ or —NH—CO-alk-$NR_7R_{15}$, a radical —NH—CO-alk-Ar in which Ar is optionally substituted with one or more substituents selected from halogen atoms and alkyl, alkoxy, nitro, amino, hydroxyl, cyano, -alk-$NH_2$, —$COOR_7$ and -alk-$COOR_7$ radicals, a radical —NH—CO—C(Ar)(CF$_3$)OCH$_3$, a 1-pyrrolyl radical which is optionally substituted with a radical —$COOR_7$, a radical —NH—CO—NH-alk-Ar in which Ar is optionally substituted with one or more substituents selected from halogen atoms and alkyl, alkoxy, nitro, amino, hydroxyl, cyano, -alk-$NH_2$, —$COOR_7$ and -alk-$COOR_7$ radicals, a radical —NH—CO—NH—Het, —NH—CO—NH—Het", —NH—CO—NH-alk-Het or —NH—CO—NH-alk-Het", a radical —NH—CO—NH—Ar in which Ar is optionally substituted with one or more substituents selected from halogen atoms and alkyl, alkoxy, nitro, amino, hydroxyl, cyano, -alk-$NH_2$, —$COOR_7$ and -alk-$COOR_7$ radicals, or a radical —NH—COalk, —NH-Cocycloalkyl, —NH—CO—NH-alk or —NH—CO—$NH_2$, $R_6$ represents a radical —NH—CHO, —COOalk, -alk-$COOR_7$ or -alk-CO—$NR_7R_{15}$, a phenylalkyl radical in which the phenyl ring is substituted with one or more substituents selected from halogen atoms and alkyl, alkoxy, nitro, amino, acetylamino, hydroxyl, cyano, -alk-$NH_2$, —$COOR_7$ and -alk-$COOR_7$ radicals, a radical —$R_{14}$—$COOR_7$, —CO—$COOR_7$ or —NH—$COOR_{17}$, a radical —NH—CO—Ar in which Ar is substituted with one or more substituents selected from halogen atoms and alkyl, alkoxy, nitro, amino, hydroxyl, cyano, -alk-$NH_2$, —$COOR_7$ and -alk-$COOR_7$ radicals, a radical —NH—CO—Het, —NH—CO-alk-Het, —NH—CO-Het", —NH—CO-alk-Het", —NH—CO-alk(2–6C)—$COOR_7$, —NH—CO-alk (2–6C)—$NH_2$, —NH—CO-alk-N(alk)$_2$ or —NH—CO-alk-NHalk, a radical —NH—CO-alk-Ar in which Ar is optionally substituted with one or more substituents selected from halogen atoms and alkyl, alkoxy, nitro, amino, hydroxyl, cyano, -alk-$NH_2$, —$COOR_7$ and -alk-$COOR_7$ radicals, a radical —NH—CO—C(Ar)(CF$_3$)OCH$_3$ or -alk-Het", a 1-pyrrolyl radical which is optionally substituted with a radical —$COOR_7$, a radical —NH—CO—NH-alk-Ar in which Ar is optionally substituted with one or more substituents selected from halogen atoms and alkyl, alkoxy, nitro, amino, hydroxyl, cyano, -alk-$NH_2$, —$COOR_7$ and -alk-$COOR_7$ radicals, a radical —NH—CO—NH-alk-Het, —NH—CO—NH-alk-Het" or —NH—CO—NH-Het", or a radical —NH—CO—NH—Ar in which Ar is substituted with one or more substituents selected from halogen atoms and alkyl, alkoxy, nitro, amino, hydroxyl, cyano, -alk-$NH_2$, —$COOR_7$ and -alk-$COOR_7$ radicals, $R_7$ represents a hydrogen atom or an alkyl radical, $R_8$ represents a hydrogen atom or an alkyl, -alk-COOR$_7$, -alk-Het", -alk-Het or -alk-NR$_9$R$_7$ radical, a phenylalkyl radical in which the phenyl ring is optionally substituted with one or more substituents selected from halogen atoms and alkyl, alkoxy, nitro, amino, hydroxyl, -alk-NH$_2$, COOR$_7$, cyano and -alk-COOR$_7$ radicals, a phenyl radical which is optionally substituted with one or more substituents selected from halogen atoms and alkyl, alkoxy, nitro, amino, hydroxyl, -alk-NH$_2$, —COOR$_7$, cyano and -alk-COOR$_7$ radicals, or a radical -Het or -Het", $R_9$ represents a hydrogen atom or an alkyl radical, $R_{10}$ represents a radical -alk-COOR$_7$, -Het" or -alk-Het", a phenyl radical which is substituted with one or more substituents selected from halogen atoms and alkyl, alkoxy, nitro, amino, hydroxyl, -alk-NH$_2$, —COOR$_7$, cyano and -alk-COOR$_7$ radicals or a phenylalkyl radical in which the phenyl ring is substituted with one or more substituents selected from halogen atoms and alkyl, alkoxy, nitro, amino, hydroxyl, -alk-NH$_2$, —COOR$_7$, cyano and -alk-COOR$_7$ radicals, $R_{11}$ represents an alkyl, —Het, —Het" or alkoxycarbonyl radical, $R_{12}$ represents a hydrogen atom or an alkyl, -alk-COOR$_7$, -alk-NR$_7$R$_{15}$, -alk-Het or -alk-Het" radical or a phenylalkyl radical in which the phenyl ring is optionally substituted with one or more substituents selected from halogen atoms and alkyl, alkoxy, nitro, amino, hydroxyl, -alk-NH$_2$, carboxyl, alkoxycarbonyl, cyano and -alk-COOR$_7$ radicals, $R_{13}$ represents a hydrogen atom or an alkyl radical, $R_{14}$ represents a —CHOH— or —CHOH-alk(1–5C)— chain, $R_{15}$ represents a hydrogen atom or an alkyl radical, $R_{16}$ represents a hydrogen atom or an alkyl radical, $R_{17}$ represents an an alkyl or phenylalkyl radical, $R_{18}$ represents a hydrogen atom or an alkyl radical having 1 to 9 carbon atoms in a straight or branched chain, an alkoxy, -alk-COOR$_7$, -alk-Het", -alk-Het or -alk-NR$_9$R$_7$ radical, a phenylalkyl radical in which the phenyl ring is optionally substituted with one or more substituents selected from halogen atoms and alkyl, alkoxy, nitro, amino, hydroxyl, -alk-NH$_2$, —COOR$_7$, cyano and -alk-COOR$_7$ radicals, a phenyl radical which is optionally substituted with one or more substituents selected from halogen atoms and alkyl, alkoxy, nitro, amino, hydroxyl, -alk-NH$_2$, COOR$_7$, cyano and -alk-COOR$_7$ radicals, or a radical Het or -Het", $R_{19}$ represents an alkyl or phenyl radical, $R_{20}$ represents a hydrogen atom or an alkyl radical, alk represents an alkyl or alkylene radical, alk' represents an alkyl radical, Ar represents a phenyl radical, m is equal to 0, 1 or 2, Het represents a saturated or unsaturated mono- or polycyclic heterocycle containing 4 to 9 carbon atoms and one or more hetero atoms, said hetero atoms being O, S or N, Het" represents a saturated or unsaturated mono- or polycyclic heterocycle containing 1 to 3 carbon atoms and one or more hetero atoms, said hetero atoms being O, S or N, which is optionally substituted with one or more alkyl, phenyl or phenylalkyl radicals or a saturated or unsaturated mono- or polycyclic heterocycle containing 4 to 9 carbon atoms and one or more hetero atoms, said hetero atoms being O, S or N, which is substituted with one or more alkyl, phenyl or phenylalkyl radicals, with the proviso that when $R_1$ and $R_2$ represent hydrogen atoms and R represents a radical CHR$_6$, $R_6$ represents a radical -alk-Het" in which alk represents an alkyl (1C) radical, Het" is other than a 2-imidazolyl radical, with the proviso that the alkyl, alkoxy and alkylene radicals and portions of radicals contain 1 to 6 carbon atoms in a straight or branched chain and the cycloalkyl radicals contain 3 to 6 carbon atoms, as well as an isomer of a compound of formula (I) for which $R_3$ represents a radical NO-alk, C(COOR$_7$)R$_{16}$, C(CONR$_7$R$_{15}$)R$_{16}$ or CHR$_{10}$, a tautomeric form of a compound of formula (I) for which R represents a radical CH—R$_6$, $R_6$ represents a isoradical —CO—COOR$_7$, an enantiomer or a diastereoisomer of a compound of formula (I) for which R represents a radical C(R$_4$)R$_5$ or CH—R$_6$, or a salt of any of said compounds, together with a pharmaceutically acceptable carrier.

2. A pharmaceutical composition comprising a compound of formula (I) according to claim 1, wherein Het is a pyrrolyl, pyridyl, pyrimidinyl, morpholinyl, pyrazinyl, pyrrolidinyl, piperazinyl, piperidyl, thienyl or furyl ring and Het" is a pyrrolyl ring substituted with one or more alkyl, phenyl or phenylalkyl radicals, a pyridyl ring substituted with one or more alkyl, phenyl or phenylalkyl radicals, a pyrimidinyl ring substituted with one or more alkyl, phenyl or phenylalkyl radicals, an imidazolyl ring optionally substituted with one or more alkyl, phenyl or phenylalkyl radicals, a thiazolyl ring optionally substituted with one or more alkyl, phenyl or phenylalkyl radicals, a thiazolinyl ring optionally substituted with one or more alkyl, phenyl or phenylalkyl radicals, a pyrazinyl ring optionally substituted with one or more alkyl, phenyl or phenylalkyl radicals, a tetrazolyl ring optionally substituted with one or more alkyl, phenyl or phenylalkyl radicals, a triazolyl ring optionally substituted with one or more alkyl, phenyl or phenylalkyl radicals, an oxazolyl ring optionally substituted with one or more alkyl, phenyl or phenylalkyl radicals, a pyrrolidinyl ring substituted with one or more alkyl, phenyl or phenylalkyl radicals, an azetidinyl ring optionally substituted with one or more alkyl, phenyl or phenylalkyl radicals, a piperazinyl ring substituted with one or more alkyl, phenyl or phenylalkyl radicals, a piperidyl ring substituted with one or more alkyl, phenyl or phenylalkyl radicals, a thienyl ring substituted with one or more alkyl, phenyl or phenylalkyl radicals, an oxazolinyl ring optionally substituted with one or more alkyl, phenyl or phenylalkyl radicals, a furyl ring optionally substituted with one or more alkyl, phenyl or phenylalkyl radicals, or an imidazolinyl ring optionally substituted with one or more alkyl, phenyl or phenylalkyl radicals.

3. A pharmaceutical composition comprising a compound of formula (I) according to claim 1, wherein said polyfluoroalkoxy radicals are trifluoromethoxy radicals.

4. A pharmaceutical composition comprising a compound of formula (I) according to claim 1, wherein R represents a radical C=R$_3$ in which R$_3$ represents a radical NO-alk, CHR$_{10}$ or NR$_7$, R$_1$ represents a hydrogen or halogen atom or a radical NH—CO—NR$_8$R$_9$ and R$_2$ represents a hydrogen atom.

5. A pharmaceutical composition comprising a compound of formula (I) according to claim 1, wherein R represents a radical C(R$_4$)R$_5$, R$_4$ represents an alkyl radical or a phenylalkyl radical in which the phenyl ring is optionally substituted with one or more substituents selected from halogen atoms and alkyl, alkoxy, nitro, amino, hydroxyl, cyano, -alk-NH$_2$, —COOR$_7$ and -alk-COOR$_7$ radicals, R$_5$ represents a radical —NR$_{12}$R$_{13}$, —NH—COOR$_{17}$, -alk-COOR$_7$, -alk-CONR$_7$R$_{15}$, -alk-NR$_7$R$_{15}$, -alk-OH, -alk-CN or -alk-Het", a phenylalkyl radical in which the phenyl ring is substituted with one or more substituents selected from halogen atoms and alkyl, alkoxy, nitro, amino, hydroxyl, cyano, -alk-NH$_2$, —COOR$_7$ and -alk-COOR$_7$ radicals, a radical —NH—CO—Ar in which Ar is optionally substituted with one or more substituents selected from halogen atoms and alkyl, alkoxy, nitro, amino, hydroxyl, cyano, -alk-NH$_2$, —COOR$_7$ and -alk-COOR$_7$ radicals, a radical —NH—CO-alk-COOR$_7$, a 1-pyrrolyl radical which is optionally substituted with a radical —COOR$_7$ or a radical —NH—COalk.

6. A pharmaceutical composition containing a compound of formula (I) according to claim 1, wherein R represents a radical CH—R$_6$ in which R$_6$ represents —NH—CHO, —COOalk, -alk-COOR$_7$, phenylalkyl in which the phenyl ring is substituted with one or more substituents selected from halogen atoms and alkyl, alkoxy, nitro, amino, acetylamino, hydroxyl, cyano, -alk-NH$_2$, —COOR$_7$ and -alk-COOR$_7$ radicals, —R$_{14}$—COOR$_7$, —NH—COOR$_{17}$, —NH—CO—Het, —NH—CO-Het", —NH—CO-alk (2–6C)—COOR$_7$, —NH—CO-alk-N(alk)$_2$, —NH—CO-alk-Ar in which Ar is optionally substituted with one or more substituents selected from halogen atoms and alkyl, alkoxy, nitro, amino, hydroxyl, cyano, -alk-NH$_2$, —COOR$_7$ and -alk-COOR$_7$ radicals, —NH—CO—C(Ar)(CF$_3$)OCH$_3$, -alk-Het" or 1-pyrrolyl which is optionally substituted with a radical –COOR$_7$.

7. A pharmaceutical composition comprising a compound of formula (I) according to claim 1, wherein the substituent R$_1$ is in position –7 or –8.

8. A pharmaceutical composition comprising a pharmaceutically effective amount of at least one compound of formula (I) selected from:

ethyl 5H,10H-imidazo[1,2-a]indeno[1,2-e]pyrazin-4-one-10-carboxylate, 10-imino-5H,10H-imidazo[1,2-a]indeno[1,2-e]pyrazin-4-one, 10-(2-carboxybenzyl)-5H,10H-imidazo[1,2-a]indeno-[1,2-e]pyrazin-4-one, 10-(4-carboxybenzyl)-5H,10H-imidazo[1,2-a]indeno-[1,2-e]pyrazin-4-one, 10-(3-carboxybenzylidene)-5H,10H-imidazo[1,2-a]-indeno[1,2-e]pyrazin-4-one, 10-(3-carboxybenzyl)-5H,10H-imidazo[1,2-a]indeno-[1,2-e]pyrazin-4-one, 10-(4-acetylaminobenzyl)-5H,10H-imidazo[1,2-a]indeno-[1,2-e]pyrazin-4-one, 10-(4-aminobenzyl)-5H,10H-imidazo[1,2-a]indeno-[1,2-e]pyrazin-4-one, 10-[(1-methylimidazol-2-yl)methylene]-5H,10H-imidazo-[1,2-a]indeno[1,2-e]pyrazin-4-one, 10-[(1-methylimidazol-2-yl)methyl]-5H,10H-imidazo-[1,2-a]indeno[1,2-e]pyrazin-4-one, 10-(tert-butoxycarbonylmethyl)-5H,10H-imidazo-[1,2-a]indeno[1,2-e]pyrazin-4-one, 10-(carboxymethyl)-5H,10H-imidazo[1,2-a]indeno-[1,2-e]pyrazin-4-one, 10-(carboxymethylene)-5H,10H-imidazo[1,2-a]indeno-[1,2-e]pyrazin-4-one, 5-(4-hydroxyimidazo[1,2-a]indeno[1,2-e]pyrazin-10-ylidene)pentanoic acid, 10-(1-carboxy-1-hydroxymethyl)-8-(3-methylureido)-5H,10H-imidazo[1,2-a]indeno [1,2-e]pyrazin-4-one, 10-nicotinoylamino-5H,10H-imidazo[1,2-a]indeno-[1,2-e]pyrazin-4-one, methyl 3-[10-(4,5-dihydro-4-oxo-10H-imidazo[1,2-a]-indeno [1,2-e]pyrazinyl)aminocarbonyl]propionate, 10-(3-diethylaminopropionamido)-5H,10H-imidazo-[1,2-a]indeno[1,2-e]pyrazin-4-one, 10-formamido-5H,10H-imidazo[1,2-a]indeno[1,2-e]-pyrazin-4-one, (10R)-10[(R)-α-methoxy-α-trifluoromethylphenyl-acetamido]-5H,10H-imidazo[1,2-a]indeno[1,2-e]pyrazin-4-one, (10S)-10[(R)-α-methoxy-α-trifluoromethylphenyl-acetamido]-5H,10H-imidazo[1,2-a]indeno[1,2-e]pyrazin-4-one, 10-(4-phenylbutyramido)-5H,10H-imidazo[1,2-a]-indeno [1,2-e]pyrazin-4-one, 10-phenyiacetamido-5H,10H-imidazo[1,2-a]indeno-[1,2-e]pyrazin-4-one, tert-butyl N-[10-(4,5-dihydro4-oxo-10H-imidazo-[1,2-a]indeno [1,2-e]pyrazinyl)]carbamate, 10-(1-pyrrolyl)-5H,10H-imidazo[1,2-a]indeno-[1,2-e]pyrazin-4-one, methyl 1-[10-(4,5-dihydro4-oxo-10H-imidazo-[1,2-a]indeno[1,2-e]pyrazinyl)]pyrrole-2-carboxylate, 10-methoxyimino-5H,10H-imidazo[1,2-a]indeno-[1,2-e]pyrazin-4-one, 10-acetamido-10-methyl-5H,10H-imidazo[1,2-a]-indeno [1,2-e]pyrazin-4-one, 10-amino-10-methyl-5H,10H-imidazo[1,2-a]-indeno[1,2-e]pyrazin-4-one, 10-(4-imidazolylmethyl)-5H,10H-imidazo[1,2-a]-indeno [1,2-e]pyrazin-4-one, 10-[3-(imidazol-1-yl)propyl]-10-methyl-5H,10H-imidazo[1,2-a]indeno[1,2-e]pyrazin-4-one, 10-[4-(imidazol-1-yl)butyl]-10-methyl-5H,10H-imidazo [1,2-a]indeno[1,2-e]pyrazin-4-one, 10-amino-10-methyl-8-(3-methylureido)-5H,10H-imidazo[1,2-a]indeno[1,2-e]pyrazin-4-one, 10-(carboxymethylene)-8-(3-methylureido)-5H,10H-imidazo[1,2-a]indeno [1,2-e]pyrazin-4-one, 10-amino-10-methyl-8-(3-n-propylureido)-5H,10H-imidazo[1,2-a]indeno[1,2-e]pyrazin-4-one, 10-amino-10-benzyl-7-chloro-5H,10H-imidazo-[1,2-a]indeno[1,2-e]pyrazin-4-one, 10-(3-aminobenzyl)-5H,10H-imidazo[1,2-a]-indeno[1,2-e]pyrazin-4-one, 10-(3-aminobenzylidene)-5H-imidazo[1,2-a]indeno-[1,2-e]pyrazin-4-one, 10-(3-acetylaminobenzyl)-5H,10H-imidazo[1,2-a]-indeno[1,2-e]pyrazin-4-one, 10-(3-methoxycarbonylbenzylidene)-5H-imidazo-[1,2-a]indeno[1,2-e]pyrazin-4-one, 10-amino-10-phenethyl-5H,10H-imidazo[1,2-a]indeno-[1,2-e]pyrazin-4-one, 10-amino-10-(3-phenylpropyl)-5H,10H-imidazo-[1,2-a]-indeno[1,2-e]pyrazin-4-one, 10-acetamido-10-(4-phenylbutyl)-5H,10H-imidazo-[1,2-a]indeno[1,2-e]pyrazin-4-one, 5-(10-methyl-4,5-dihydro4-oxo-10H-imidazo-[1,2-a]indeno[1,2-e]pyrazin-10-yl)valeric acid, 10-(3-dimethylaminopropyl)-10-methyl-5H,10H-imidazo[1,2-a]indeno[1,2-e]pyrazin-4-one, 4-(10-methyl-4,5-dihydro4-oxo-10H-imidazo-[1,2-a]indeno[1,2-e]pyrazin-10-yl)butyronitrile, 4-(10-methyl-4,5-dihydro4-oxo-10H-imidazo-[1,2-a]indeno[1,2-e]pyrazin-10-yl)butyric acid, 10-hydroxymethyl-10-methyl-5H,10H-imidazo-[1,2-a]indeno[1,2-e]pyrazin-4-one, 4-(10-methyl-4,5-dihydro4-oxo-10H-imidazo-[1,2-a]indeno[1,2-e]pyrazin-10-yl)butyramide, (10-methyl4,5-dihydro4-oxo-10H-imidazo[1,2-a]-indeno[1,2-e]pyrazin-10-yl)acetic acid, 3-(10-methyl-4,5-dihydro4-oxo-10H-imidazo-[1,2-a]indeno[1,2-e]pyrazin-10-yl)propionitrile, 3-(10-methyl-4,5-dihydro4-oxo-10H-imidazo-[1,2-a]indeno[1,2-e]pyrazin-10-yl)propionic acid, 10-(4-hydroxybutyl)-10-methyl-5H,10H-imidazo-[1,2-a]indeno[1,2-e]pyrazin-4-one, 10-methyl-10-[(1-methylimidazol-2-yl)methyl]-5H,10H-imidazo[1,2-a]indeno [1,2-e]pyrazin-4-one, 10-[(1-methylimidazol-5-yl)methylene]-5H,10H-imidazo-[1,2-a]indeno[1,2-e]pyrazin-4-one, 10-[(1-methylimidazol-5-yl)methyl]-5H,10H-imidazo-[1,2-a]indeno[1,2-e]pyrazin-4-one, 8-[3-(3-fluorophenyl)ureido]-10-(carboxymethyl)-5H,10H-imidazo[1,2-a]indeno [1,2-e]pyrazin-4-one,

[8-(3-methylureido)-4,5-dihydro4-oxo-10H-imidazo-[1,2-a]indeno[1,2-e]pyrazin-10-yl]acetic acid, (+)-[8-(3-methylureido)-4,5-dihydro-4-oxo-10H-imidazo[1,2-a]indeno[1,2-e]pyrazin-10-yl]acetic acid, (−)-[8-(3-methylureido)-4,5-dihydro4-oxo-10H-imidazo[1,2-a]indeno[1,2-e]pyrazin-10-yl]acetic acid, (4,5-dihydro4-oxo-10H-imidazo[1,2-a]indeno[1,2-e]-pyrazin-10-yl)glycolic acid, 10-methyl-10-(1-pyrrolyl)-5H,10H-imidazo[1,2-a]-indeno[1,2-e]pyrazin-4-one, 3-[10-(10-methyl4-oxo4,5-dihydro-10H-imidazo-[1,2-a]-indeno [1,2-e]pyrazinyl)aminocarbonyl]-2,2-dimethylpropionic acid, 4-[10-(10-methyl4-oxo4,5-dihydro-10H-imidazo-[1,2-a] indeno [1,2-e]pyrazinyl)aminocarbonyl]-3,3-dimethylbutyric acid, 1-[10-(4-oxo-4,5-dihydro-10H-imidazo-[1,2-a]indeno[1,2-e]pyrazinyl)]pyrrole-2-carboxylic acid, 3-[10-(4-oxo4,5-dihydro-10H-imidazo[1,2-a]indeno-[1,2-e]pyrazinyl) aminocarbonyl]propionic acid, 10-amino-10-ethyl-5H,10H-imidazo[1,2-a]indeno-[1,2-e]pyrazin-4-one, 10-amino-10-benzyl-5H,10H-imidazo[1,2-a]indeno-[1,2-e]pyrazin-4-one, 10-amino-10-propyl-5H,10H-imidazo[1,2-a]indeno-[1,2-e]pyrazin-4-one, 3-[10-(10-methyl-4-oxo-4,5-dihydro-10H-imidazo-[1,2-a]indeno [1,2-e]pyrazinyl)aminocarbonyl]propionic acid, tert-butyl N-[10-(10-methyl4-oxo4,5-dihydro-10H-imidazo[1,2-a]indeno [1,2-e]pyrazinyl)]carbamate, 4-[10-(10-methyl4-oxo4,5-dihydro-10H-imidazo-[1,2-a] indeno [1,2-e]pyrazinyl)aminocarbonyl]butyric acid, 10-amino-10-isopropyl-5H,10H-imidazo[1,2-a]indeno-[1,2-e]pyrazin-4-one, 10-amino-10-butyl-5H,10H-imidazo[1,2-a]indeno-[1,2-e]pyrazin-4-one, 10-methyl-10-methylamino-5H,10H-imidazo[1,2-a]-indeno[1,2-e]pyrazin-4-one, 10-carboxymethylene-7-chloro-5H-imidazo[1,2-a]-indeno[1,2-e]pyrazin-4-one, 10-amino-10-methyl-8-(3-methylureido)-5H,10H-imidazo[1,2-a]indeno[1,2-e]pyrazin-4-one and its enantiomers, or 10-(1,3-dimethyl-1H-pyrazole4-methylene)-5H,10H-imidazo[1,2-a]indeno[1,2-e]pyrazin-4-one, or a salt of one of said compounds together with a pharmaceutically acceptable carrier.

9. A compound of formula (I):

in which

R represents a radical C=$R_3$, C($R_4$)$R_5$ or CH—$R_6$, $R_1$ and $R_2$, which may be identical or different, represent hydrogen or halogen atoms or alkyl, alkoxy, amino, —N=CH—N(alk)alk', nitro, cyano, phenyl, imidazolyl, $SO_3H$, hydroxyl, polyfluoroalkoxy, —$COOR_7$, —NH—CO—$NR_8R_9$, —N(alk)-CO-$NR_8R_9$, —N(alk-Ar)—CO—$NR_8R_9$, —NH—CS—$NR_8R_9$, —N(alk)—CS—$NR_8R_9$, —NH—CO—$R_{18}$, —NH—CS—$R_{19}$, —NH—C(=$NR_{20}$)—$NR_7R_9$, —N(alk)—C(=$NR_{20}$)—$NR_7R_9$, —NH—$SO_2$—$NR_7R_9$, —N(alk)—$SO_2$—$NR_7R_9$, —CO—$NR_7R_9$, —NH—$SO_2$—$CF_3$, —NH—$SO_2$-alk, —$NR_9R_{11}$, —S(O)$_m$-alk-Ar or —$SO_2$—$NR_7R_9$ radicals, 2-oxo-1-imidazolidinyl radicals in which position −3 is optionally substituted with an alkyl radical, or 2-oxoperhydro-1-pyrimidinyl radicals in which position −3 is optionally substituted with an alkyl radical, $R_3$ represents a radical NO-alk, $CHR_{10}$, $NR_7$, C(COO$R_7$)$R_{16}$ or C(CON$R_7R_{15}$)$R_{16}$, $R_4$ represents an alkyl, -alk-Het or -alk-Het" radical or a phenylalkyl radical in which the phenyl ring is optionally substituted with one or more substituents selected from halogen atoms and alkyl, alkoxy, nitro, amino, hydroxyl, cyano, -alk-$NH_2$, —COO$R_7$ and -alk-COO$R_7$ radicals, $R_5$ represents a radical —$NR_{12}R_{13}$, —NH—CHO, —NH—COO$R_{17}$, —NH—$SO_2R_{19}$, —COO$R_7$, -alk-COO$R_7$, -alk-CON$R_7R_{15}$, -alk-$NR_7R_{15}$, -alk-OH, -alk-CN or -alk-Het", a phenylalkyl radical in which the phenyl ring is substituted with one or more substituents selected from halogen atoms and alkyl, alkoxy, nitro, amino, hydroxyl, cyano, -alk-$NH_2$, —COO$R_7$ and -alk-COO$R_7$ radicals, a radical —NH—CO—Ar in which Ar is optionally substituted with one or more substituents selected from halogen atoms and alkyl, alkoxy, nitro, amino, hydroxyl, cyano, -alk-$NH_2$, —COO$R_7$ and -alk-COO$R_7$ radicals, a radical —NH—CO—Het, —NH—CO—Het", —NH—CO-alk-Het, —NH—CO-alk-Het", —NH—CO-alk-COO$R_7$ or —NH—CO-alk-$NR_7R_{15}$, a radical —NH—CO-alk-Ar in which Ar is optionally substituted with one or more substituents selected from halogen atoms and alkyl, alkoxy, nitro, amino, hydroxyl, cyano, -alk-$NH_2$, —$COOR_7$ and -alk-$COOR_7$ radicals, a radical —NH—CO—C(Ar)($CF_3$)$OCH_3$, a 1-pyrrolyl radical which is optionally substituted with a radical —$COOR_7$, a radical —NH—CO—NH-alk-Ar in which Ar is optionally substituted with one or more substituents selected from halogen atoms and alkyl, alkoxy, nitro, amino, hydroxyl, cyano, -alk-$NH_2$, —$COOR_7$ and -alk-$COOR_7$ radicals, a radical —NH—CO—NH—Het, —NH—CO—NH-Het", —NH—CO—NH-alk-Het or —NH—CO—NH-alk-Het", a radical —NH—CO—NH—Ar in which Ar is optionally substituted with one or more substituents selected from halogen atoms and alkyl, alkoxy, nitro, amino, hydroxyl, cyano, -alk-$NH_2$, —$COOR_7$ and -alk-$COOR_7$ radicals, or a radical —NH—COalk, —NH—COcycloalkyl, —NH—CO—NH-alk or —NH—CO—$NH_2$, $R_6$ represents a radical —NH—CHO, —COOalk, -alk-$COOR_7$ or -alk-CO-$NR_7R_{15}$, a phenylalkyl radical in which the phenyl ring is substituted with one or more substituents selected from halogen atoms and alkyl, alkoxy, nitro, amino, acetylamino, hydroxyl, cyano, -alk-$NH_2$, —$COOR_7$ and -alk-$COOR_7$ radicals, a radical —$R_{14}$—$COOR_7$, —CO—$COOR_7$ or —NH—$COOR_{17}$, a radical —NH—CO—Ar in which Ar is substituted with one or more substituents selected from halogen atoms and alkyl, alkoxy, nitro, amino, hydroxyl, cyano, -alk-$NH_2$, —$COOR_7$ and -alk-$COOR_7$ radicals, a radical —NH—CO-Het, —NH—CO-alk-Het, —NH—CO-Het", —NH—CO-alk-Het", —NH—CO-alk(2–6C)-$COOR_7$, —NH—CO-alk(2–6C)-$NH_2$, —NH—CO-alk-N(alk)$_2$ or —NH—CO-alk-NHalk, a radical —NH—CO-alk-Ar in which Ar is optionally substituted with one or more substituents selected from halogen atoms and alkyl, alkoxy, nitro, amino, hydroxyl, cyano, -alk-$NH_2$, —$COOR_7$ and -alk-$COOR_7$ radicals, a radical —NH—CO—C(Ar)($CF_3$)$OCH_3$ or -alk-Het", a 1-pyrrolyl radical which is optionally substituted with a radical —$COOR_7$, a radical —NH—CO—NH-alk-Ar in which Ar is optionally substituted with one or more substituents selected from halogen atoms and alkyl, alkoxy, nitro, amino, hydroxyl, cyano, -alk-$NH_2$, —$COOR_7$ and -alk-$COOR_7$ radicals, a radical —NH—CO—NH-alk-Het, —NH—CO—NH-alk-Het" or —NH—CO—NH-Het", or a radical —NH—CO—NH—Ar in which Ar is substituted with one or more substituents selected from halogen atoms and alkyl, alkoxy, nitro, amino, hydroxyl, cyano, -alk-$NH_2$, —$COOR_7$ and -alk-$COOR_7$ radicals, $R_7$ represents a hydrogen atom or an alkyl radical, $R_8$ represents a hydrogen atom or an alkyl, -alk-$COOR_7$, -alk-Het", -alk-Het or -alk-$NR_9R_7$ radical, a phenylalkyl radical in which the phenyl ring is optionally substituted with one or more substituents selected from halogen atoms and alkyl, alkoxy, nitro, amino, hydroxyl, -alk-$NH_2$, $COOR_7$, cyano and -alk-$COOR_7$ radicals, a phenyl radical which is optionally substituted with one or more substituents selected from halogen atoms and alkyl, alkoxy, nitro, amino, hydroxyl, -alk-$NH_2$, —$COOR_7$, cyano and -alk-$COOR_7$ radicals, or a radical -Het or -Het", $R_9$ represents a hydrogen atom or an alkyl radical, $R_{10}$ represents a radical -alk-$COOR_7$, —Het" or -alk-Het", a phenyl radical which is substituted with one or more substituents selected from halogen atoms and alkyl, alkoxy, nitro, amino, hydroxyl, -alk-$NH_2$, —$COOR_7$, cyano and -alk-$COOR_7$ radicals or a phenylalkyl radical in which the phenyl ring is substituted with one or more substituents selected from halogen atoms and alkyl, alkoxy, nitro, amino, hydroxyl, -alk-$NH_2$, —$COOR_7$, cyano and -alk-$COOR_7$ radicals, $R_{11}$ represents an alkyl, -Het, -Het" or alkoxycarbonyl radical, $R_{12}$ represents a hydrogen atom or an alkyl, -alk-$COOR_7$, -alk-$NR_7R_{15}$, -alk-Het or -alk-Het" radical or a phenylalkyl radical in which the phenyl ring is optionally substituted with one or more substituents selected from halogen atoms and alkyl, alkoxy, nitro, amino, hydroxyl, -alk-$NH_2$, carboxyl, alkoxycarbonyl, cyano and -alk-$COOR_7$ radicals, $R_{13}$ represents a hydrogen atom or an alkyl radical, $R_{14}$ represents a —CHOH— or —CHOH-alk(1–5C)— chain, $R_{15}$ represents a hydrogen atom or an alkyl radical, $R_{16}$ represents a hydrogen atom or an alkyl radical, $R_{17}$ represents an an alkyl or phenylalkyl radical, $R_{18}$ represents a hydrogen atom or an alkyl radical having 1 to 9 carbon atoms in a straight or branched chain, an alkoxy, -alk-$COOR_7$, -alk-Het", -alk-Het or -alk-$NR_9R_7$ radical, a phenylalkyl radical in which the phenyl ring is optionally substituted with one or more substituents selected from halogen atoms and alkyl, alkoxy, nitro, amino, hydroxyl, -alk-$NH_2$, —$COOR_7$, cyano and -alk-$COOR_7$ radicals, a phenyl radical which is optionally substituted with one or more substituents selected from halogen atoms and alkyl, alkoxy, nitro, amino, hydroxyl, -alk-$NH_2$, $COOR_7$, cyano and -alk-$COOR_7$ radicals, or a radical Het or -Het", $R_{19}$ represents an alkyl or phenyl radical, $R_{20}$ represents a hydrogen atom or an alkyl radical, alk represents an alkyl or alkylene radical, alk' represents an alkyl radical, Ar represents a phenyl radical, m is equal to 0, 1 or2, Het represents a saturated or unsaturated mono- or polycyclic heterocycle containing 4 to 9 carbon atoms and one or more hetero atoms, said hetero atoms being O, S or N, Het" represents a saturated or unsaturated mono- or polycyclic heterocycle containing 1 to 3 carbon atoms and one or more hetero atoms, said hetero atoms being O, S, or N, which is optionally substituted with one or more alkyl, phenyl or phenylalkyl radicals or a saturated or unsaturated mono- or polycyclic heterocycle containing 4 to 9 carbon atoms and one or more hetero atoms, said hetero atoms being O, S or N, which is substituted with one or more alkyl, phenyl or phenylalkyl radicals, with the exception of the compounds for which (a) $R_1$ and $R_2$ represent hydrogen atoms, R represents a radical $CHR_6$, $R_6$ represents a radical -alk-Het" in which alk represents an alkyl (1C) radical and Het" represents a 2-imidazolyl radical, (b) $R_1$ and $R_2$ represent hydrogen atoms, R represents a radical $CHR_6$ in which $R_6$ represents a radical —NHCHO or -alk-$COOR_7$ in which $R_7$ represents a hydrogen atom or a tert-butyl radical, (c) $R_1$ and $R_2$ represent hydrogen atoms, R represents a radical C=$R_3$ in which $R_3$ represents a radical CHR$_{10}$ and R$_{10}$ represents a 2-imidazolyl radical, and (d) R$_1$ represents a hydrogen atom, R$_2$ represents a chlorine atom in position −7, R represents a radical CHR$_6$ and R6 represents a radical —NHCHO, with the proviso that the alkyl, alkoxy and alkylene radicals and portions of radicals contain 1 to 6 carbon atoms in a straight or branched chain and the cycloalkyl radicals contain 3 to 6 carbon atoms, as well as an isomer of a compound of formula (I) for which R$_3$ represents a radical NO-alk, C(COOR$_7$)R$_{16}$, C(CONR$_7$R$_{15}$)R$_{16}$ or CHR$_{10}$, a tautomeric form of a compound of formula (I) for which R represents a radical CH—R$_6$, R$_6$ represents a radical —CO—COOR$_7$, an enantiomer or diastereoisomer of a compound of formula (1) for which R represents a radical C(R$_4$)R$_5$ or CH—R$_6$,or a salt of any of said compounds.

10. A compound of formula (I) according to claim 9, wherein Het is a pyrrolyl, pyridyl, pyrimidinyl, morpholinyl, pyrazinyl, pyrrolidinyl, piperazinyl, piperidyl, thienyl or furyl ring and Het" is a pyrrolyl ring substituted with one or more alkyl, phenyl or phenylalkyl radicals, a pyridyl ring substituted with one or more alkyl, phenyl or phenylalkyl radicals, a pyrimidinyl ring substituted with one or more alkyl, phenyl or phenylalkyl radicals, an imidazolyl ring optionally substituted with one or more alkyl, phenyl or phenylalkyl radicals, a thiazolyl ring optionally substituted with one or more alkyl, phenyl or phenylalkyl radicals, a thiazolinyl ring optionally substituted with one or more alkyl, phenyl or phenylalkyl radicals, a pyrazinyl ring optionally substituted with one or more alkyl, phenyl or phenylalkyl radicals, a tetrazolyl ring optionally substituted with one or more alkyl, phenyl or phenylalkyl radicals, a triazolyl ring optionally substituted with one or more alkyl, phenyl or phenylalkyl radicals, an oxazolyl ring optionally substituted with one or more alkyl, phenyl or phenylalkyl radicals, a pyrrolidinyl ring substituted with one or more alkyl, phenyl or phenylalkyl radicals, an azetidinyl ring optionally substituted with one or more alkyl, phenyl or phenylalkyl radicals, a piperazinyl ring substituted with one or more alkyl, phenyl or phenylalkyl radicals, a piperidyl ring substituted with one or more alkyl, phenyl or phenylalkyl radicals, a thienyl ring substituted with one or more alkyl, phenyl or phenylalkyl radicals, an oxazolinyl ring optionally substituted with one or more alkyl, phenyl or phenylalkyl radicals, a furyl ring optionally substituted with one or more alkyl, phenyl or phenylalkyl radicals, or an imidazolinyl ring optionally substituted with one or more alkyl, phenyl or phenylalkyl radicals.

11. A compound of formula (I) according to claim 9, wherein said polyfluoroalkoxy radicals are trifluoromethoxy radicals.

12. A compound of formula (I) according to claim 9, wherein R represents a radical C=R$_3$ in which R$_3$ represents a radical NO-alk, CHR$_{10}$ or NR$_7$, R$_1$ represents a hydrogen or halogen atom or a radical NH—CO—NR$_8$R$_9$ and R$_2$ represents a hydrogen atom.

13. A compound of formula (I) according to claim 9, wherein R represents a radical C(R$_4$)R$_5$, R$_4$ represents an alkyl radical or a phenylalkyl radical in which the phenyl ring is optionally substituted with one or more substituents selected from halogen atoms and alkyl, alkoxy, nitro, amino, hydroxyl, cyano, -alk-NH$_2$, —COOR$_7$ and -alk-COOR$_7$ radicals, R$_5$ represents a radical —NR$_{12}$R$_{13}$, —NH—COOR$_{17}$, -alk-COOR$_7$, -alk-CONR$_7$R$_{15}$, -alk-NR$_7$R$_{15}$, -alk-OH, -alk-CN or -alk-Het", a phenylalkyl radical in which the phenyl ring is substituted with one or more substituents selected from halogen atoms and alkyl, alkoxy, nitro, amino, hydroxyl, cyano, -alk-NH$_2$, —COOR$_7$ and -alk-COOR$_7$ radicals, a radical —NH—CO—Ar in which Ar is optionally substituted with one or more substituents selected from halogen atoms and alkyl, alkoxy, nitro, amino, hydroxyl, cyano, -alk-NH$_2$, —COOR$_7$ and -alk-COOR$_7$ radicals, a radical —NH—CO-alk-COOR$_7$, a 1-pyrrolyl radical which is optionally substituted with a radical —COOR$_7$ or a radical —NH—COalk.

14. A compound of formula (I) according to claim 9, wherein R represents a radical CH—R$_6$ in which R$_6$ represents —NH—CHO, —COOalk, -alk-COOR$_7$, phenylalkyl in which the phenyl ring is substituted with one or more substituents selected from halogen atoms and alkyl, alkoxy, nitro, amino, acetylamino, hydroxyl, cyano, -alk-NH$_2$, —COOR$_7$ and -alk-COOR$_7$ radicals, —R$_{14}$—COOR$_7$, —NH—COOR$_{17}$, —NH—CO-Het, —NH—CO-Het", —NH—CO-alk(2–6C)—COOR$_7$, —NH—CO-alk-N(alk)$_2$, —NH—CO-alk-Ar in which Ar is optionally substituted with one or more substituents selected from halogen atoms and alkyl, alkoxy, nitro, amino, hydroxyl, cyano, -alk-NH$_2$, —COOR$_7$ and -alk-COOR$_7$ radicals, —NH—CO—C(Ar)(CF$_3$)OCH$_3$, -alk-Het" or 1-pyrrolyl which is optionally substituted with a radical —COOR$_7$.

15. A compound of formula (I) according to claim 9, wherein the substituent R$_1$ is in position −7 or −8.

16. A compound selected from:

ethyl 5H,10H-imidazo[1,2-a]indeno[1,2-e]pyrazin-4-one-10-carboxylate, 10-imino-5H,10H-imidazo[1,2-a]indeno[1,2-e]pyrazin-4-one, 10-(2-carboxybenzyl)-5H,10H-imidazo[1,2-a]indeno-[1,2-e]pyrazin-4-one, 10-(4-carboxybenzyl)-5H,10H-imidazo[1,2-a]indeno-[1,2-e]pyrazin-4-one, 10-(3-carboxybenzylidene)-5H,10H-imidazo[1,2-a]-indeno[1,2-e]pyrazin-4-one, 10-(3-carboxybenzyl)-5H,10H-imidazo[1,2-a]indeno-[1,2-e]pyrazin-4-one, 10-(4-acetylaminobenzyl)-5H,10H-imidazo[1,2-a]indeno-[1,2-e]pyrazin-4-one, 10-(4-aminobenzyl)-5H,10H-imidazo[1,2-a]indeno-[1,2-e]pyrazin-4-one, 10-[(1 -methylimidazol-2-yl)methylene]-5H,10H-imidazo-[1,2-a]indeno[1,2-e]pyrazin-4-one, 10-[(l-methylimidazol-2-yl)methyl]-5H,10H-imidazo-[1,2-a]indeno[1,2-e]pyrazin-4-one, 10-(tert-butoxycarbonylmethyl)-5H,10H-imidazo-[1,2-a]indeno[1,2-e]pyrazin-4-one, 10-(carboxymethyl)-5H,10H-imidazo[1,2-a]indeno-[1,2-e]pyrazin-4-one, 10-(carboxymethylene)-5H,10H-imidazo[1,2-a]indeno-[1,2-e]pyrazin-4-one, 5-(4-hydroxyimidazo[1,2-a]indeno[1,2-e]pyrazin-10-ylidene)pentanoic acid, 10-(1-carboxy-1-hydroxymethyl)-8-(3-methylureido)-5H,10H-imidazo[1,2-a]indeno[1,2-e]pyrazin-4-one, 10-nicotinoylamino-5H,10H-imidazo[1,2-a]indeno-[1,2-e]pyrazin-4-one, methyl 3-[10-(4,5-dihydro4-oxo-10H-imidazo-[1,2-a]-indeno[1,2-e]pyrazinyl) aminocarbonyl]propionate, 10-(3-diethylaminopropionamido)-5H,10H-imidazo-[1,2-a]indeno[1,2-e]pyrazin-4-one, 10-formamido-5H,10H-imidazo[1,2-a]indeno[1,2-e]-pyrazin-4-one, (10R)-10[(R)-α-methoxy-α-trifluoromethylphenyl-
acetamido]-5H,10H-imidazo [1,2-a]indeno[1,2-e]
pyrazin-4-one, (10S)-10[(R)-α-methoxy-α-trifluoromethylphenyl-
acetamido]-5H,10H-imidazo [1,2-a]indeno[1,2-e]
pyrazin-4-one, 10-(4-phenylbutyramido)-5H,10H-imidazo[1,2-a]-indeno
[1,2-e]pyrazin-4-one, 10-phenylacetamido-5H,10H-imidazo[1,2-a]indeno-[1,2-
e]pyrazin-4-one, tert-butyl N-[10-(4,5-dihydro4-oxo-10H-imidazo-[1,2-a]
indeno[1,2-e]pyrazinyl)]carbamate, 10-(1-pyrrolyl)-5H,10H-imidazo[1,2-a]indeno-[1,2-e]
pyrazin-4-one, methyl 1-[10-(4,5-dihydro4-oxo-10H-imidazo-[1,2-a]
indeno[1,2-e]pyrazinyl)]pyrrole-2-carboxylate, 10-methoxyimino-5H,10H-imidazo[1,2-a]indeno-[1,2-e]
pyrazin-4-one, 10-acetamido-10-methyl-5H,10H-imidazo[1,2-a]-indeno
[1,2-e]pyrazin-4-one, 10-amino-10-methyl-5H,10H-imidazo[1,2-a]-indeno[1,
2-e]pyrazin-4-one, 10-(4-imidazolylmethyl)-5H,10H-imidazo[1,2-a]-indeno
[1,2-e]pyrazin-4-one, 10-[3-(imidazol-1-yl)propyl]-10-methyl-5H,10H-
imidazo[1,2-a]indeno[1,2-e]pyrazin-4-one, 10-[4-(imidazol-1-yl)butyl]-10-methyl-5H,10H-imidazo
[1,2-a]indeno[1,2-e]pyrazin-4-one, 10-amino-10-methyl-8-(3-methylureido)-5H,10H-
imidazo[1,2-a]indeno[1,2-e]pyrazin-4-one, 10-(carboxymethylene)-8-(3-methylureido)-5H,10H-
imidazo[1,2-a]indeno [1,2-e]pyrazin-4-one, 10-amino-10-methyl-8-(3-n-propylureido)-5H,10H-
imidazo[1,2-a]indeno[1,2-e]pyrazin-4-one, 10-amino-10-benzyl-7-chloro-5H,10H-imidazo-[1,2-a]
indeno[1,2-e]pyrazin-4-one, 10-(3-aminobenzyl)-5H,10H-imidazo[1,2-a]-indeno[1,2-
e]pyrazin-4-one, 10-(3-aminobenzylidene)-5H-imidazo[1,2-a]indeno-[1,2-
e]pyrazin-4-one, 10-(3-acetylaminobenzyl)-5H,10H-imidazo-[1,2-a]-
indeno[1,2-e]pyrazin-4-one, 10-(3-methoxycarbonylbenzylidene)-5H-imidazo-[1,2-a]
indeno[1,2-e]pyrazin-4-one, 10-amino-10-phenethyl-5H,10H-imidazo[1,2-a]indeno-
[1,2-e]pyrazin-4-one, 10-amino-10-(3-phenylpropyl)-5H,10H-imidazo[1,2-a]-
indeno[1,2-e]pyrazin-4-one, 10-acetamido-10-(4-phenylbutyl)-5H,10H-imidazo-[1,2-
a]indeno[1,2-e]pyrazin-4-one, 5-(10-methyl4,5-dihydro4-oxo-10H-imidazo-[1,2-a]
indeno[1,2-e]pyrazin-10-yl)valeric acid, 10-(3-dimethylaminopropyl)-10-methyl-5H,10H-
imidazo[1,2-a]indeno[1,2-e]pyrazin-4-one, 4-(10-methyl4,5-dihydro4-oxo-10H-imidazo-[1,2-a]
indeno[1,2-e]pyrazin-10-yl)butyronitrile, 4-(10-methyl4,5-dihydro4-oxo-10H-imidazo-[1,2-a]
indeno[1,2-e]pyrazin-10-yl)butyric acid, 10-hydroxymethyl-10-methyl-5H,10H-imidazo-[1,2-a]
indeno[1,2-e]pyrazin-4-one, 4-(10-methyl-4,5-dihydro4-oxo-10H-imidazo-[1,2-a]
indeno[1,2-e]pyrazin-10-yl)butyramide, (10-methyl4,5-dihydro4-oxo-10H-imidazo[1,2-a]-indeno
[1,2-e]pyrazin-10-yl)acetic acid, 3-(10-methyl4,5-dihydro-4-oxo-10H-imidazo-[1,2-a]
indeno[1,2-e]pyrazin-10-yl)propionitrile, 3-(10-methyl-4,5-dihydro4-oxo-10H-imidazo-[1,2-a]
indeno[1,2-e]pyrazin-10-yl)propionic acid, 10-(4-hydroxybutyl)-10-methyl-5H,10H-imidazo-[1,2-a]
indeno[1,2-e]pyrazin-4-one, 10-methyl-10-[(1 -methylimidazol-2-yl)methyl]-5H,10H-
imidazo[1,2-a]indeno [1,2-e]pyrazin-4-one, 10-[(1-methylimidazol-5-yl)methylene]-5H,10H-
imidazo-[1,2-a]indeno[1,2-e]pyrazin-4-one, 10-[(1-methylimidazol-5-yl)methyl]-5H,10H-imidazo-[1,
2-a]indeno[1,2-e]pyrazin-4-one, 8-[3-(3-fluorophenyl)ureido]-10-(carboxymethyl)-5H,
10H-imidazo[1,2-a]indeno [1,2-e]pyrazin-4-one,

[8-(3-methylureido)-4,5-dihydro-4-oxo-10H-imidazo-[1,
2-a]indeno[1,2-e]pyrazin-10-yl]acetic acid, (+)-[8-(3-methylureido)-4,5-dihydro4-oxo-10H-imidazo
[1,2-a]indeno[1,2-e]pyrazin-10-yl]acetic acid, (−)-[8-(3-methylureido)-4,5-dihydro4-oxo-10H-imidazo-
[1,2-a]indeno[1,2-e]pyrazin-10-yl]acetic acid, (4,5-dihydro4-oxo-10H-imidazo[1,2-a]indeno[1,2-e]-
pyrazin-10-yl)glycolic acid, 10-methyl-10-(1-pyrrolyl)-5H,10H-imidazo[1,2-a]-
indeno[1,2-e]pyrazin-4-one, 3-[10-(10-methyl4-oxo4,5-dihydro-10H-imidazo-[1,2-a]-
indeno[1,2-e]pyrazinyl)aminocarbonyl]-2,2-
dimethylpropionic acid, 4-[10-(10-methyl4-oxo4,5-dihydro-10H-imidazo-[1,2-a]
indeno[1,2-e]pyrazinyl)aminocarbonyl]-3,
3-dimethylbutyric acid, 1-[10-(4-oxo4,5-dihydro-10H-imidazo[1,2-a]-indeno[1,
2-e]pyrazinyl)]pyrrole-2-carboxylic acid, 3-[10-(4-oxo-4,5-dihydro-10H-imidazo[1,2-a]-indeno[1,
2-e]pyrazinyl) aminocarbonyl]propionic acid, 10-amino-10-ethyl-5H,10H-imidazo[1,2-a]indeno-[1,2-
e]pyrazin-4-one, 10-amino-10-benzyl-5H,10H-imidazo[1,2-a]indeno-[1,2-
e]pyrazin-4-one, 10-amino-10-propyl-5H,10H-imidazo[1,2-a]indeno-[1,2-
e]pyrazin-4-one, 3-[10-(10-methyl4-oxo4,5-dihydro-10H-imidazo-[1,2-a]
indeno[1,2-e]pyrazinyl) aminocarbonyl]propionic acid, tert-butyl N-[10-(10-methyl4-oxo-4,5-dihydro-10H-
imidazo[1,2-a]indeno [1,2-e]pyrazinyl)]carbamate, 4-[10-(10-methyl4-oxo-4,5-dihydro-10H-imidazo-[1,2-a]
indeno[1,2-e]pyrazinyl) aminocarbonyl]butyric acid, 10-amino-10-isopropyl-5H,10H-imidazo[1,2-a]indeno-
[1,2-e]pyrazin-4-one, 10-amino-10-butyl-5H,10H-imidazo[1,2-a]indeno-[1,2-
e]pyrazin-4-one, 10-methyl-10-methylamino-5H,10H-imidazo[1,2-a]-
indeno[1,2-e]pyrazin-4-one, 10-carboxymethylene-7-chloro-5H-imidazo[1,2-a]-
indeno[1,2-e]pyrazin-4-one, 10-amino-10-methyl-8-(3-methylureido)-5H,10H-
imidazo[1,2-a]indeno[1,2-e]pyrazin-4-one and its
enantiomers, or 10-(1,3-dimethyl-1H-pyrazole4-methylene)-5H,10H-
imidazo[1,2-a]indeno[1,2-e]pyrazin-4-one, or a salt of
any said compounds.

* * * * *

UNITED STATES PATENT AND TRADEMARK OFFICE
CERTIFICATE OF CORRECTION

PATENT NO. : 5,807,859
DATED : September 15, 1998
INVENTOR(S) : Jean-Claude Aloup et al.

It is certified that error appears in the above-identified patent and that said Letters Patent is hereby corrected as shown below:

Claim 1, Column 80, Line 33, "Cocycloalkyl" should read --COcycloalkyl--;

Claim 8, Column 84, Line 22, "pheniacetamido" should read --phenylacetamido--;

Claim 8, Column 84, Line 25, "dihydro4" should read --dihydro-4--;

Claim 8, Column 84, Line 29, "dihydro4" should read --dihydro-4--;

Claim 8, Column 85, Line 1, "dihydro4" should read --dihydro-4--;

Claim 8, Column 85, Line 5, "dihydro4" should read --dihydro-4--;

Claim 8, Column 85, Line 7, "dihydro4" should read --dihydro-4--;

Claim 8, Column 85, Line 11, "dihydro4" should read --dihydro-4--;

Claim 8, Column 85, Line 13, "methyl4,5-dihydro4" should read --methyl-4,5-dihydro-4--;

Claim 8, Column 85, Line 16, "dihydro4" should read --dihydro-4--;

Claim 8, Column 85, Line 31, "dihydro4" should read --dihydro-4--;

Claim 8, Column 85, Line 35, "dihydro4" should read --dihydro-4--;

UNITED STATES PATENT AND TRADEMARK OFFICE
CERTIFICATE OF CORRECTION

PATENT NO. : 5,807,859
DATED : September 15, 1998
INVENTOR(S) : Jean-Claude Aloup et al.

It is certified that error appears in the above-identified patent and that said Letters Patent is hereby corrected as shown below:

Claim 8, Column 85, Line 42, "methyl4" should read --methyl-4-- and "oxo4,5" should read --oxo-4,5--;

Claim 8, Column 85, Line 45, "methyl4" should read --methyl-4-- and "oxo4,5" should read --oxo-4,5--;

Claim 8, Column 85, Line 63, "methyl4" should read --methyl-4-- and "oxo4,5" should read --oxo-4,5--;

Claim 8, Column 85, Line 50, "oxo4,5" should read --oxo-4,5--;

Claim 8, Column 85, Line 61, "oxo4,5" should read --oxo-4,5--;

Claim 16, Column 90, Line 62, "dihydro4" should read --dihydro-4--;

Claim 16, Column 91, Line 11, "dihydro4" should read --dihydro-4--;

Claim 16, Column 91, Line 16, "dihydro4" should read --dihydro-4--;

Claim 16, Column 91, Line 64, "dihydro4" should read --dihydro-4--;

Claim 16, Column 92, Line 19, "dihydro4" should read --dihydro-4--;

Claim 16, Column 92, Line 23, "dihydro4" should read --dihydro-4--;

Claim 16, Column 91, Line 32, "$_{10}$H-" should read --10H- --;

UNITED STATES PATENT AND TRADEMARK OFFICE
CERTIFICATE OF CORRECTION

PATENT NO. : 5,807,859
DATED : September 15, 1998
INVENTOR(S) : Jean-Claude Aloup et al.

It is certified that error appears in the above-identified patent and that said Letters Patent is hereby corrected as shown below:

Claim 16, Column 91, Line 53, "methyl4,5" should read --methyl-4,5--;

Claim 16, Column 91, Line 57, "methyl4,5" should read --methyl-4,5--;

Claim 16, Column 91, Line 59, "methyl4,5" should read --methyl-4,5--;

Claim 16, Column 91, Line 66, "methyl4,5" should read --methyl-4,5--;

Claim 16, Column 92, Line 1, "methyl4,5" should read --methyl-4,5--;

Claim 16, Column 92, Line 27, "methylr-oxo4,5" should read --methyl-4-oxo-4,5 --;

Claim 16, Column 92, Line 31, "methylr-oxo4,5" should read --methyl-4-oxo-4,5 --;

Claim 16, Column 92, Line 45, "methylr-oxo4,5" should read --methyl-4-oxo-4,5 --;

UNITED STATES PATENT AND TRADEMARK OFFICE
CERTIFICATE OF CORRECTION

PATENT NO. : 5,807,859
DATED : September 15, 1998
INVENTOR(S) : Jean-Claude Aloup et al.

It is certified that error appears in the above-identified patent and that said Letters Patent is hereby corrected as shown below:

Claim 16, Column 92, Line 49, "methyl4" should read --methyl-4 --.

Signed and Sealed this

Twenty-first Day of March, 2000

Attest:

Attesting Officer

Q. TODD DICKINSON

Commissioner of Patents and Trademarks